United States Patent
Röder et al.

(10) Patent No.: US 9,653,272 B2
(45) Date of Patent: May 16, 2017

(54) MASS-SPECTRAL METHOD FOR SELECTION, AND DE-SELECTION, OF CANCER PATIENTS FOR TREATMENT WITH IMMUNE RESPONSE GENERATING THERAPIES

(71) Applicants: Biodesix, Inc., Boulder, CO (US); Globelmmune Inc., Louisville, CO (US)

(72) Inventors: Joanna Röder, Steamboat Springs, CO (US); Heinrich Röder, Steamboat Springs, CO (US)

(73) Assignees: BIODESIX, INC., Boulder, CO (US); GLOBEIMMUNE, INC., Louisville, CO (US)

(*) Notice: Subject to any disclaimer, the term of this patent is extended or adjusted under 35 U.S.C. 154(b) by 701 days.

(21) Appl. No.: 13/835,909

(22) Filed: Mar. 15, 2013

(65) Prior Publication Data

US 2013/0344111 A1 Dec. 26, 2013

Related U.S. Application Data

(60) Provisional application No. 61/664,329, filed on Jun. 26, 2012, provisional application No. 61/664,308, filed on Jun. 26, 2012.

(51) Int. Cl.

| | |
|---|---|
| G01N 33/48 | (2006.01) |
| G01N 33/50 | (2006.01) |
| H01J 49/00 | (2006.01) |
| A61K 39/00 | (2006.01) |
| G06F 19/00 | (2011.01) |
| G01N 33/574 | (2006.01) |
| G01N 33/68 | (2006.01) |
| G06F 19/18 | (2011.01) |
| G06F 19/24 | (2011.01) |

(52) U.S. Cl.
CPC .......... *H01J 49/0036* (2013.01); *A61K 39/00* (2013.01); *A61K 39/0011* (2013.01); *G01N 33/57438* (2013.01); *G01N 33/6851* (2013.01); *G06F 19/18* (2013.01); *G06F 19/24* (2013.01); *G06F 19/3437* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,775,622 A | 10/1988 | Hitzeman | |
| 5,234,830 A | 8/1993 | Oshima | |
| 5,310,654 A | 5/1994 | Isberg | |
| 5,413,914 A | 5/1995 | Franzusoff | |
| 5,830,463 A | 11/1998 | Duke | |
| 5,858,378 A | 1/1999 | Bostwick | |
| 5,919,651 A | 7/1999 | Hitzeman | |
| 7,083,787 B2 | 8/2006 | Duke | |
| 7,439,042 B2 | 10/2008 | Duke | |
| 7,465,454 B2 | 12/2008 | Franzusoff | |
| 7,563,447 B2 | 7/2009 | Franzusoff | |
| 7,736,642 B2 | 6/2010 | Duke | |
| 7,736,905 B2 | 6/2010 | Röder | |
| 7,858,389 B2 | 12/2010 | Röder | |
| 7,858,390 B2 | 12/2010 | Röder | |
| 7,867,775 B2 | 1/2011 | Röder | |
| 7,879,620 B2 | 2/2011 | Röder | |
| 7,906,342 B2 | 3/2011 | Röder | |
| 8,024,282 B2 | 9/2011 | Tsypin | |

(Continued)

FOREIGN PATENT DOCUMENTS

| | | |
|---|---|---|
| EP | 0414404 | 2/1991 |
| FR | 2486400 | 1/1982 |
| JP | 61219387 A | 9/1986 |
| WO | 02/076499 A2 | 10/2002 |
| WO | 2004/058157 A2 | 7/2004 |
| WO | 2007/007467 A1 | 1/2007 |
| WO | 2007/133835 | 11/2007 |
| WO | 2010/065626 | 6/2010 |
| WO | 2011/115914 | 9/2011 |
| WO | 2012/019127 | 2/2012 |
| WO | 2012/083302 | 6/2012 |
| WO | 2012/109404 | 8/2012 |
| WO | 2012/125998 | 9/2012 |
| WO | 2012/174220 | 12/2012 |
| WO | 2013/025972 | 2/2013 |

OTHER PUBLICATIONS

Chung et al. Detection of tumor epidermal growth factor receptor pathway dependence by serum mass spectrometry in cancer patients. Cancer Epidemiol Biomarkers Prev, vol. 19, Jan. 19, 2010, pp. OF1 to OF8.*

(Continued)

*Primary Examiner* — Russell S Negin
(74) *Attorney, Agent, or Firm* — McDeonnell Boehnen Hulbert & Berghoff LLP

(57) ABSTRACT

A method and system for predicting in advance of treatment whether a cancer patient is likely, or not likely, to obtain benefit from administration of a yeast-based immune response generating therapy, which may be yeast-based immunotherapy for mutated Ras-based cancer, alone or in combination with another anti-cancer therapy. The method uses mass spectrometry of a blood-derived patient sample and a computer configured as a classifier using a training set of class-labeled spectra from other cancer patients that either benefitted or did not benefit from an immune response generating therapy alone or in combination with another anti-cancer therapy. Also disclosed are methods of treatment of a cancer patient, comprising administering a yeast-based immune response generating therapy, which may be yeast-based immunotherapy for mutated Ras-based cancer, to a patient selected by a test in accordance with predictive mass spectral methods disclosed herein, in which the class label for the spectra indicates the patient is likely to benefit from the yeast-based immunotherapy.

72 Claims, 38 Drawing Sheets

(56) References Cited

U.S. PATENT DOCUMENTS

| | | | |
|---|---|---|---|
| 8,067,559 B2 | 11/2011 | Franzusoff | |
| 8,097,469 B2 * | 1/2012 | Roder et al. | 436/173 |
| 8,135,136 B2 | 3/2012 | Van Loon | |
| 2002/0044948 A1 | 4/2002 | Khleif | |
| 2003/0035810 A1 | 2/2003 | Caplan | |
| 2007/0172503 A1 | 7/2007 | Selitrennikoff | |
| 2007/0224208 A1 | 9/2007 | Guo | |
| 2007/0231921 A1 * | 10/2007 | Roder et al. | 436/173 |
| 2007/0287719 A1 * | 12/2007 | Boyden et al. | 514/265.1 |
| 2008/0003239 A1 | 1/2008 | Duke | |
| 2009/0098154 A1 | 4/2009 | Franzusoff | |
| 2010/0034840 A1 | 2/2010 | Apelian | |
| 2010/0111912 A1 | 5/2010 | Apelian | |
| 2010/0189749 A1 | 7/2010 | Franzusoff | |
| 2010/0291612 A1 * | 11/2010 | Luider | G01N 33/57407 435/29 |
| 2011/0208433 A1 | 8/2011 | Grigorieva | |
| 2011/0256098 A1 | 10/2011 | Apelian | |
| 2011/0269139 A1 | 11/2011 | Gao | |
| 2012/0093792 A1 | 4/2012 | Masuyama | |
| 2012/0107347 A1 | 5/2012 | Hodge | |
| 2012/0193525 A1 | 8/2012 | Röder | |
| 2012/0321664 A1 | 12/2012 | Bellgrau | |

OTHER PUBLICATIONS

Bizzini et al., "Use of live *Saccharomyces cerevisiae* cells as a biological response modifier in experimental infections", FEMS Microbiology Immunology, 64:155-168 (1990).

Brake et al., "alpha-Factor-directed synthesis and secretion of mature foreign proteins in *Saccharomyces cerevisiae*", Proceedings of the National Academy of Sciences USA, 81:4642-4646 (1984).

Eto et al., "Immunization with recombinant *Escherichia coli* expressing retinal S-antigen-induced experimental autoimmune uveitis (EAU) in Lewis rats", Cellular Immunology, 147(1):203-214 (1993).

Franzusoff et al., "Yeasts Encoding Tumour Antigens in Cancer Immunotherapy", Expert Opinion in Biological Therapy, 5(4):565-575 (2005).

Franzusoff et al., "Bochemical and Genetic Definition of the Cellular Protease Requirement for HIV-1 gp160 Processing", The Journal of Biological Chemistry, 270(7):3154-3159 (1995).

Fujita et al., "Studies in the development of Japanese encephalitis vaccine: expression of virus envelope glycoprotein V3 (E) gene in yeast", Bulletin of the World Health Organization, 65(3):303-308 (1987).

Klepfer et al., "Characterization of rabies glycoprotein expressed in yeast", Archives of Virology, 128:269-286 (1993).

Moore et al., "Novel yeast-based vaccine 1-40, against HIV-SF2 gp160 promotes a cytotoxic 43-62 cell response", FASEB Journal (online), vol. 10, No. 6, 1996, p. A1473, ZP002186594, Joint Meeting of the American Society of Biochemistry and Molecular Biology, The American Society of Investigative Pathology and the American Association of Immunologists; New Orleans, LA, USA; Jun. 2-6, 1996.

Schreuder et al., "Yeast expressing hepatitis B virus surface antigen determinants on its surface: implications for a possible oral vaccine", Vaccine, 14(5):383-388 (1996).

Sinai et al., "Enhancement of Resistance to Infectious Diseases by Oral Administration of Brewer's Yeast", Infection and Immunity, 9(5):781-787 (1974).

Valenzuela et al., "Antigen engineering in yeast: Synthesis and assembly of hybrid hepatitis B surface antigen-Herpes simplex 1gD particles", Bio/Technology, 3:323-326 (1985).

Lu et al., "Mutation-Selective Tumor Remission with Ras-Targeted, Whole Yeast-Based Immunotherapy", Cancer Research, 64:5084-5088 (2004).

Stubbs et al., "Whole recombinant yeast vaccine activates dendritic cells and elicits protective cell-mediation immunity", Nature Medicine, 7(5):625-629 (2001).

Bernstein et al., "Recombinant *Saccharomyces cerevisiae* (yeast-CEA) as a potent activator of murine dendritic cells", Vaccine, 26:509-521 (2008).

Richter et al., "Updates in adjuvant therapy in pancreatic cancer: gemcitabine and beyond", JOP, J Pancreas, 11 (2):144-147 (2010).

* cited by examiner

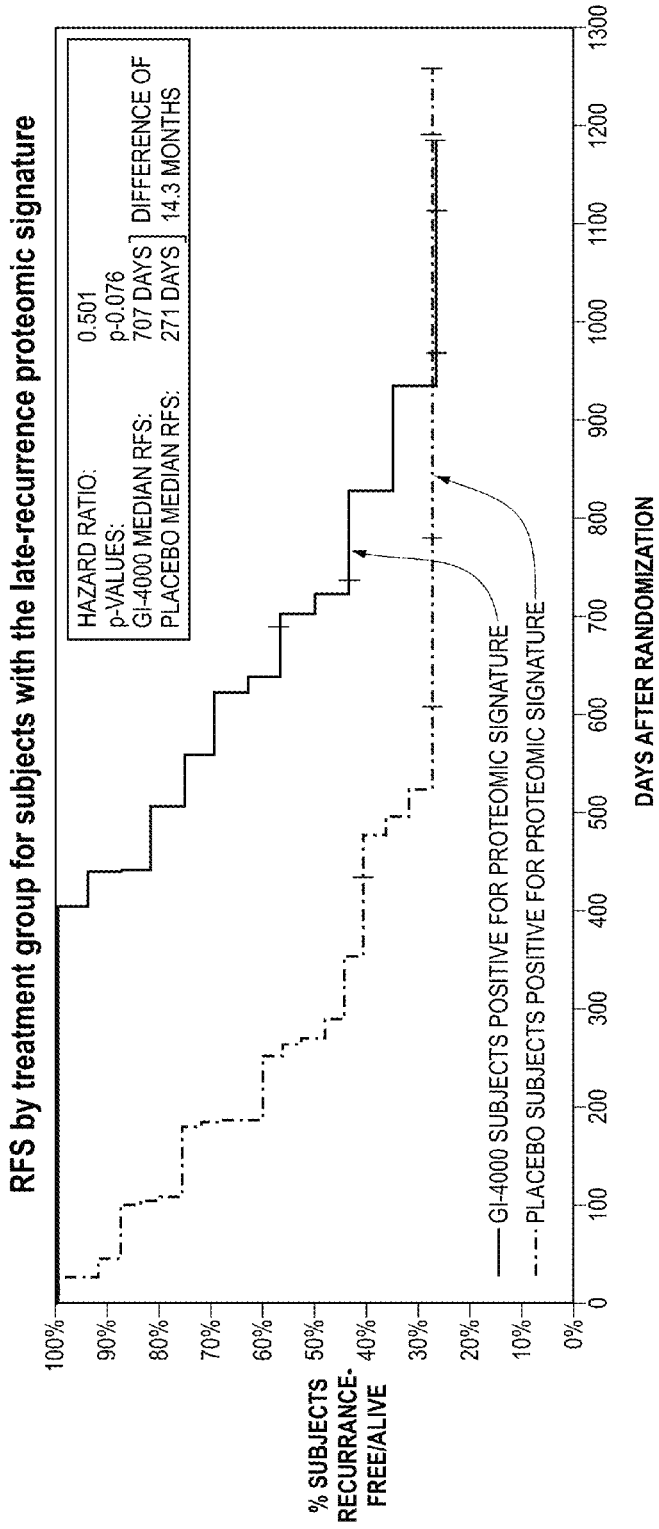

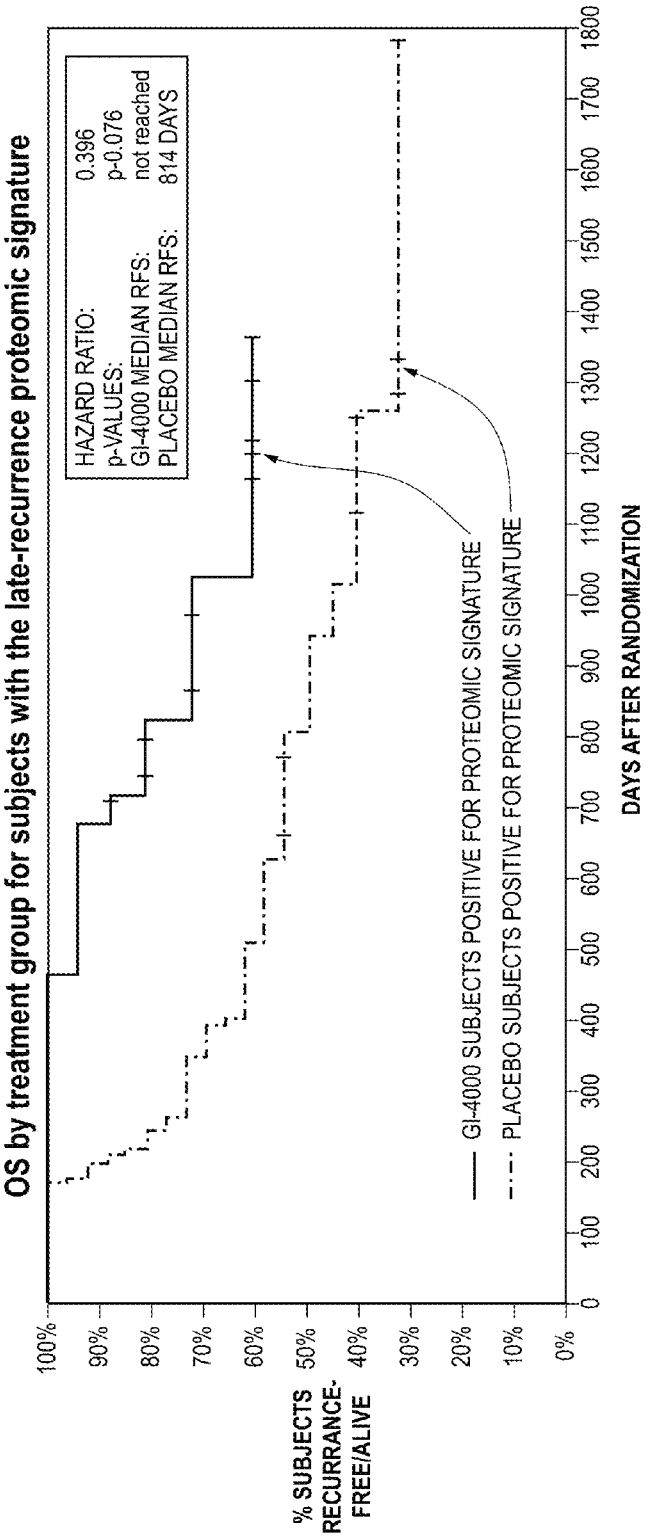

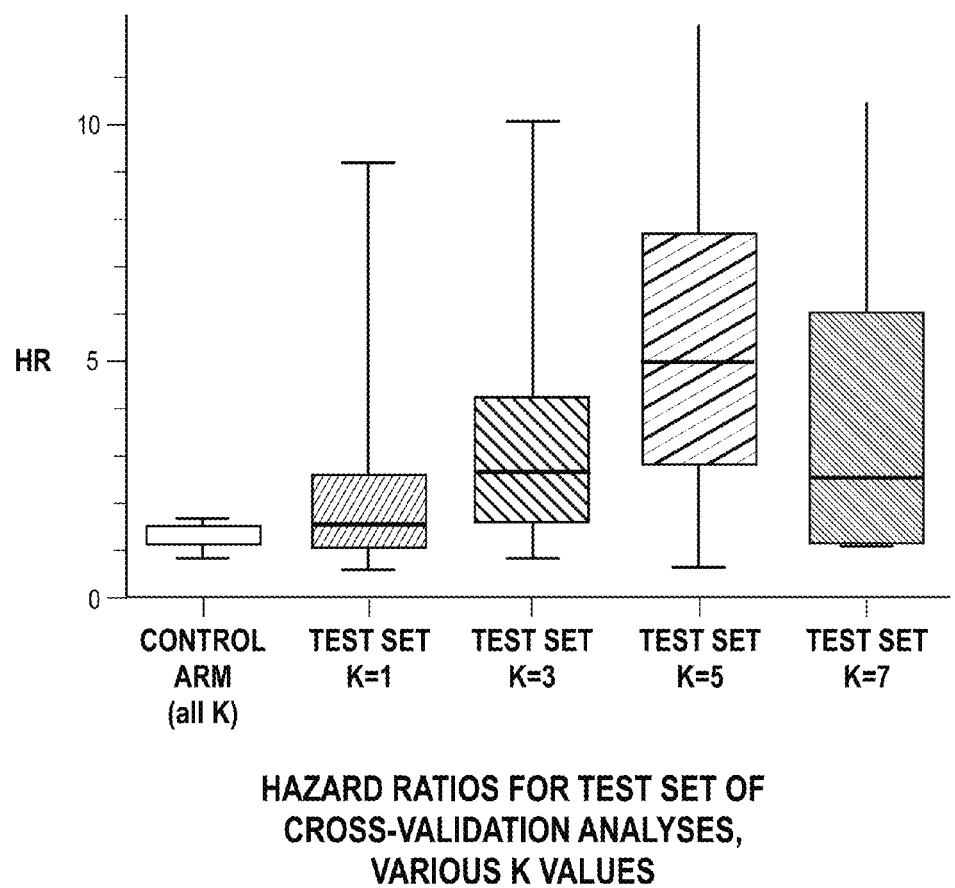

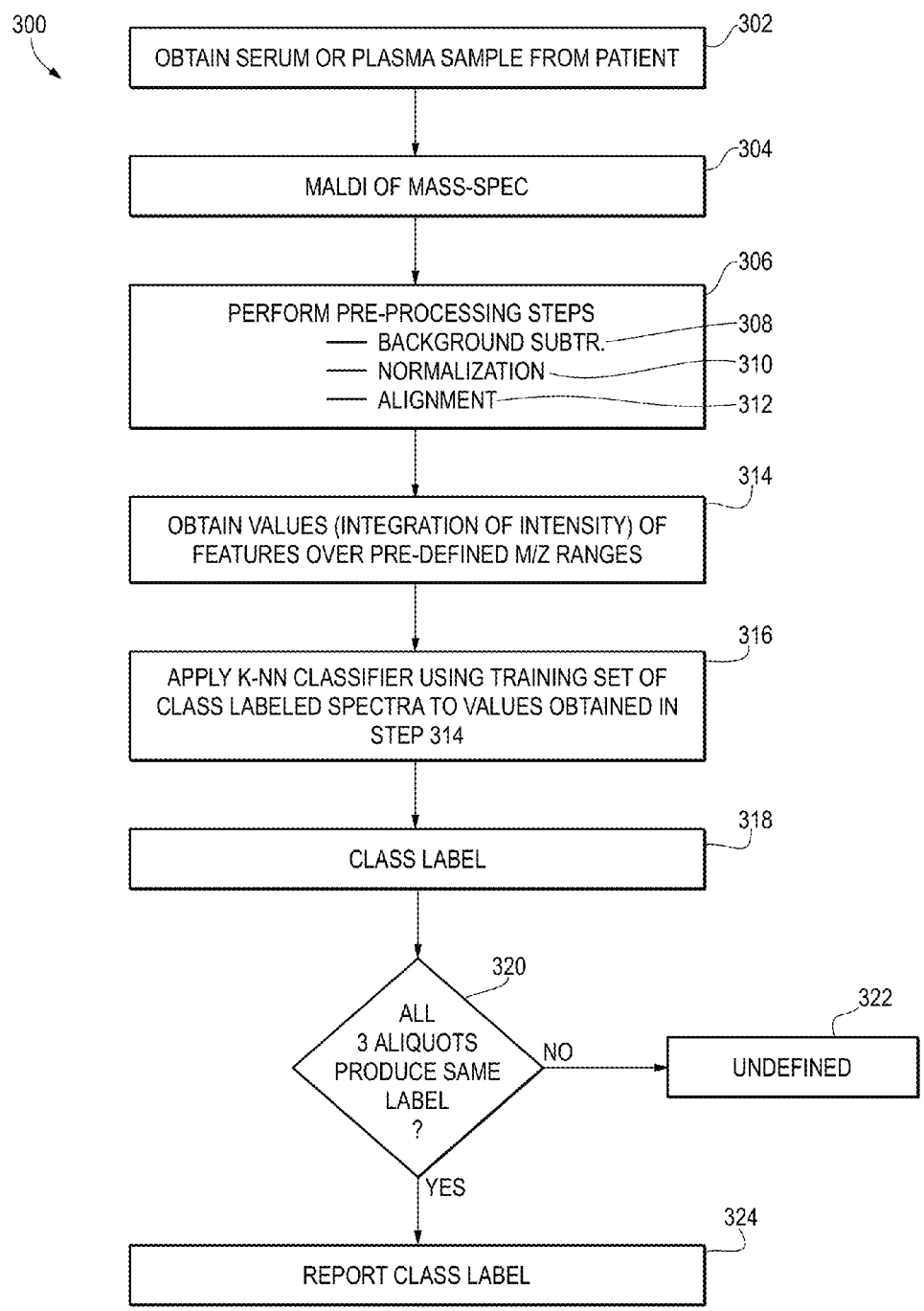

MASS-SPECTRAL METHOD FOR SELECTION, AND DE-SELECTION, OF CANCER PATIENTS FOR TREATMENT WITH IMMUNE RESPONSE GENERATING THERAPIES

CROSS-REFERENCE TO RELATED APPLICATIONS

This application claims the benefit of priority under 35 U.S.C. §119(e) to U.S. Provisional Patent Application No. 61/664,308, filed Jun. 26, 2012, and to U.S. Provisional Patent Application No. 61/664,329, filed Jun. 26, 2012. The entire disclosure of each of U.S. Provisional Patent Application No. 61/664,308 and U.S. Provisional Patent Application No. 61/664,329 is incorporated herein by reference.

STATEMENT REGARDING JOINT RESEARCH AGREEMENT

This invention was made by or on behalf of parties to a joint research agreement, executed Feb. 22, 2012. The parties to the joint research agreement are: Biodesix, Inc. and GlobeImmune, Inc.

REFERENCE TO A SEQUENCE LISTING

This application contains a Sequence Listing submitted electronically as a text file by EFS-Web. The text file, named "12-621-PRO_ST25", has a size in bytes of 19 KB, and was recorded on Mar. 15, 2013. The information contained in the text file is incorporated herein by reference in its entirety pursuant to 37 CFR §1.52(e)(5).

FIELD OF THE INVENTION

This invention relates generally to the field of methods for guiding the treatment of cancer patients. More particularly, in one aspect, this invention relates to a method of predicting, in advance of initiating treatment, whether a patient is a member of a class of patients that are likely to benefit from administration of immune response generating therapies (e.g., as cellular immunotherapy agents), either alone or in addition to standard anticancer drugs and/or other therapeutic regimens for the treatment of cancer. Methods of identifying patients which are not likely to benefit from immune response generating therapies, and/or the addition of immune response generating therapies to standard chemotherapy agents, are also disclosed. The methods of this disclosure use mass spectral data obtained from a blood-derived sample of the patient, a computer configured as a classifier operating on the mass spectral data, and a training set comprising class-labeled spectra from other cancer patients.

BACKGROUND OF THE INVENTION

Cancer is a broad group of various diseases, all involving unregulated cell growth. In cancer, cells divide and grow uncontrollably, forming malignant tumors, and invade nearby parts of the body. The cancer may also spread to more distant parts of the body through the lymphatic system or bloodstream. According to the National Cancer Institute (NCI), which tracks such statistics, the number of estimated new cases of cancer in the United States in 2012 is 1,638,910 (not including non-melanoma skin cancers), and the number of deaths per year from cancer in the United States is estimated to be 577,190(http://cancer.gov/cancertopics/cancerlibrary/what-is-cancer). Management and treatment options for cancer exist. The primary ones include surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or some combination thereof (collectively referred to herein as "anti-cancer therapies").

Additional therapies for cancer include therapeutic strategies for inducing, enhancing or suppressing an immune response, collectively called "immune therapies" or "immunotherapies" (which may also be generally referred to herein as "immune response generating therapies"). Recently, immune therapies have become more relevant in the treatment of advanced or metastatic solid tumors. Immunotherapy for use in cancer is generally designed to augment or stimulate the patient's own immune response to better control or eliminate cancerous cells, and may additionally support other treatments such as chemotherapy, surgery, radiation therapy and the use of targeted cancer therapies. Some examples of such immunotherapies for use in oncology include: (1) PROVENGE® (Dendreon), in which dendritic cells are stimulated to activate a cytotoxic response towards an antigen for use in advanced castrate resistant prostate cancer; (2) adoptive transfer of T cells to activate cytotoxic response to cancer; (3) genetically engineering T cells by introducing a virus that introduces a T cell receptor that is designed to recognize tumor antigens; (4) Algenpantucel-L, a cancer vaccine comprised of irradiated allogeneic pancreatic cancer cells transfected to express murine alpha-1,3-galactosyltransferase with potential antitumor activity; (5) viral vector-based immunotherapy; and (6) yeast-based immunotherapy.

Yeast-based immunotherapy is also referred to as TARMOGEN® (GlobeImmune, Inc., Louisville, Colo.) technology, and generally refers to a yeast vehicle expressing one or more heterologous target antigens extracellularly (on its surface), intracellularly (internally or cytosolically) or both extracellularly and intracellularly. Yeast-based immunotherapy technology has been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety. Yeast-based immunotherapy for cancer is described, for example, in U.S. Pat. Nos. 7,465, 454, 7,563,447, 8,067,559, 8,153,136, U.S. Patent Publication No. 2009-0098154, and PCT Publication No. WO 07/133,835, each of which is incorporated herein by reference in its entirety.

Yeast-based immunotherapy has a unique ability, as compared to other immunotherapies, to induce innate immune responses as well as a wide range of adaptive immune responses against the target antigen, including CD4-dependent TH17 and TH1 T cell responses and antigen-specific CD8+ T cell responses, which include cytotoxic T lymphocyte (CTL) responses, all without the use of exogenous adjuvants, cytokines, or other immunostimulatory molecules, many of which have toxicity issues. In addition, yeast-based immunotherapy compositions inhibit regulatory T cell (Treg) numbers and/or functionality, thereby enhancing effector T cell responses that might normally be suppressed by the presence of the tumor, for example. Moreover, as compared to immunotherapeutic compositions that immunize by generating antibody responses, the antigen-specific, broad-based, and potent cellular immune responses elicited by yeast-based immunotherapy are believed to be particularly effective in targeting tumor cells, even in the face of what may otherwise be a suppressive environment. Since this type of immunotherapy utilizes the natural ability of the antigen presenting cell to present relevant immunogens, it is not necessary to know the precise identity of CTL epitopes or Class II MHC epitopes of a target antigen to produce an effective yeast-based immunotherapeutic, nor is it necessary to isolate any immune cells from the patient to produce the immunotherapeutic. In fact, multiple $CD4^+$ and $CD8^+$ T cell epitopes can be targeted in a single yeast-based immunotherapeutic composition, and so the use of algorithms and complex formulas to identify putative T cell epitopes or T cell receptors is eliminated.

One series of yeast-based immunotherapy products, including the TARMOGEN® product candidates known as "GI-4000" currently in clinical development by GlobeImmune, Inc., has been developed to stimulate immune responses against a mutated Ras protein expressed by a patient's tumor. "Ras" is the name given to a family of related proteins found inside cells, including human cells. All Ras protein family members belong to a class of protein called small GTPase, and are involved in transmitting signals within cells (cellular signal transduction). Ras mutations are found in approximately 180,000 new cancer cases each year in the United States across a spectrum of tumor types, including pancreas, non-small cell lung cancer (NSCLC), colorectal, endometrial and ovarian cancers, as well as melanoma and multiple myeloma. Studies have shown that tumors with Ras mutations are generally less responsive than tumors with normal Ras to conventional chemotherapy as well as targeted agents. For some cancers, such as NSCLC or colorectal cancer, therapies that target epidermal growth factor receptor, or EGFR, have improved clinical outcomes. However, the presence of a Ras mutation in the tumor has been associated with poor prognosis despite use of EGFR targeted therapies in colorectal cancer. Similarly, other studies have shown that patients with Ras-mutated colorectal tumors do not benefit from cetuximab therapy, another EGFR targeted agent, compared to patients with normal Ras, who have improved survival rates when treated with the same therapy. As a result, patients with Ras mutations have fewer available effective treatment options. The targeted reduction of cells containing Ras mutations could result in improved clinical outcomes for patients with a number of human cancers due to the role mutated Ras plays in tumor growth. However, there are presently no available therapies targeting mutated Ras in late-stage clinical trials.

Progress in the field of immunotherapy has been slow, but recent clinical successes have given strong support to the potential of this approach as a treatment modality in cancer. However, there is a need in the art to define biomarkers which identify patients who will obtain clinical benefit from immune-based treatment in cancer and identify clinical responders and non-responders, in advance of treatment. Examples of immunotherapy markers include CD54 expression and interleukin 12p70 production, but they have not been fully validated. Also used are several cellular immune marker assays (cytokine flow cytometry, MHC tetramers, and enzyme-linked immunosorbent spot (ELISPOT)). It is important to note that assays predicting benefit from immunotherapies need to be standardized to produce reproducible and comparable results. This has not been done in this area.

There is a need in the art for practical, useful tests for determining, in advance of treatment, whether a given cancer patient is likely to benefit from administration of immune response generating therapies, either alone or in combination with other anti-cancer drug therapies, or, conversely whether such treatment is not likely to benefit a given cancer patient. This invention meets this need.

Further prior art of interest relating to ability to predict cancer patient benefit from certain types of drugs includes U.S. Pat. Nos. 7,736,905, 7,858,390; 7,858,389, 7,867,775, 8,024,282; 7,906,342 and 7,879,620, and pending U.S. patent application Ser. No. 13/356,730 filed Jan. 24, 2012, and U.S. patent application Ser. No. 12/932,295 filed Feb. 22, 2011, published as US 2011/0208433, all of which are assigned to Biodesix, Inc. The '905 patent and U.S. patent application Ser. No. 12/932,295 filed Feb. 22, 2011 are incorporated by reference herein. The '905 patent describes, among other things, a mass spectrometry based test for determining whether NSCLC cancer patients are likely to benefit from epidermal growth factor receptor (EGFR) targeting drugs. This test is known in its commercial version as "VeriStrat"; references to "VeriStrat" in the following discussion will be understood to be in reference to the test described in the '905 patent.

SUMMARY OF THE INVENTION

This invention relates generally to the field of methods for guiding the treatment of cancer patients. In one aspect, such treatment of cancer patients is immunotherapy for cancer, and in one aspect, the treatment is yeast-based immunotherapy for cancer, and in yet another aspect, the treatment is yeast-based immunotherapy for mutated Ras-positive cancers (i.e., cancers where at least some tumors are positive for a mutated Ras protein, typically detected by detecting mutations in the ras nucleotide sequence). In one aspect, the treatment is yeast-based immunotherapy for mutated Ras-positive pancreas cancer.

More particularly, in one aspect, this invention relates to a method of predicting, in advance of initiating treatment, whether a cancer patient is a member of a class of patients that are likely to benefit from administration of yeast-based immune response generating therapies (e.g., as cellular immunotherapy agents), either alone or in addition to treatment with standard anti-cancer drugs and/or other therapeutic regiments for the treatment of cancer. Methods of identifying patients which are not likely to respond to yeast-based immunotherapies, and/or the addition of immunotherapies to standard chemotherapy agents are also disclosed. Methods of identifying patients which are less likely, or not likely, to respond to yeast-based immunotherapy, and/or the addition of yeast-based immunotherapy to standard chemotherapy agents and/or other treatments for cancer (e.g., surgical resection) are also disclosed.

In yet another aspect, this invention relates to a method of predicting, in advance of initiating treatment, whether a patient is a member of a class of patients that are likely to benefit from administration of yeast-based immunotherapy for mutated Ras-positive cancer, either alone or in addition to standard anti-cancer drugs and/or other therapeutic regiments for the treatment of cancer. Methods of identifying patients which are less likely, or not likely, to respond to yeast-based immunotherapy for mutated Ras-positive cancer, and/or the addition of yeast-based immunotherapy for mutated Ras-positive cancer to standard chemotherapy agents and/or other treatments for cancer (e.g., surgical resection) are also disclosed. In one aspect, the mutated Ras-positive cancer is pancreas cancer. As one example, this document describes a method for predicting whether pancreas cancer patients are likely to benefit from administration of yeast-based immunotherapy targeting mutated Ras (e.g., the series of products known as GI-4000, described in more detail herein) in combination with administration of gemcitabine.

The methods of this disclosure use mass spectral data obtained from a blood-derived sample of the patient, a computer configured as a classifier operating on the mass spectral data, and a training set comprising class-labeled spectra from other cancer patients.

The applicants have discovered a method of predicting, in advance of treatment, whether a cancer patient is likely or not likely to benefit from administration of a yeast-based immune response generating therapy, either alone or in combination with another anti-cancer therapy. The method is based on mass spectrometry of a blood-derived sample. The use of blood-derived samples (e.g., serum, plasma) is significant, as it increases the likelihood of measuring global susceptibility to immunotherapies by giving insight into circulating markers of the immune system. Furthermore, the methods can be conducted quickly via a simple mass spectrometry test from a blood-derived sample, without the need for performing complex, time consuming assays of a patient sample or obtaining a tumor sample from the patient. Notably, the applicants have demonstrated the validity of its test from samples obtained pre-treatment. Accordingly, practical implementations of the test use pre-treatment samples from the patient and predict whether the patient is likely, or not likely, to benefit from a yeast-based immune response generating therapy.

The methods of this disclosure take the form of practical, useful tests which can be performed with the aid of a mass spectrometer (e.g., MALDI TOF instrument) and a general purpose computer configured to function as a classifier.

In one aspect, a method of predicting whether a cancer patient is likely to benefit from administration of a yeast-based immune response generating therapy, either alone or in addition to other anti-cancer therapies, is described comprising the steps of:

(a) obtaining a blood-derived sample of the patient;

(b) conducting mass-spectrometry on the sample and obtaining a mass spectrum from the sample;

(c) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients and thereby classifying the mass spectrum with a class label. The class label predicts whether the patient is likely, or not likely, to benefit from the immune response generating therapy either alone or in addition to other anti-cancer therapies. For example, the class label may take the form of "Slow" or "Quick", with "Slow" indicating that the patient is likely to benefit and the time to recurrence or disease progress of the cancer is relatively slow, whereas "Quick" may indicate that the patient is not likely to benefit and the time to recurrence or disease progressing is relatively brief. Of course, other equivalent class labels could be used, such as "benefit", "non-benefit", "good", "poor" or the like.

In one aspect, a method of predicting whether a cancer patient is likely to benefit from administration of yeast-based immunotherapy for mutated Ras-positive cancer, either alone or in addition to other anti-cancer therapies, is described comprising the steps of:

(a) obtaining a blood-derived sample of the patient to be treated with yeast-based immunotherapy for mutated Ras-positive cancer, alone or in combination with other anti-cancer therapies;

(b) conducting mass-spectrometry on the sample and obtaining a mass spectrum from the sample;

(c) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients prior to their treatment with yeast-based immunotherapy for mutated Ras-positive cancer and thereby classifying the mass spectrum with a class label. The class label predicts whether the patient is likely, or not likely, to benefit from the yeast-based immunotherapy for mutated Ras-positive cancer either alone or in addition to other anti-cancer therapies. For example, the class label may take the form of "Slow" or "Quick", with "Slow" indicating that the patient is likely to benefit and the time to recurrence or disease progress of the cancer is relatively slow, whereas "Quick" may indicate that the patient is not likely to benefit and the time to recurrence or disease progressing is relatively brief. As above, other equivalent class labels could be used, such as "benefit", "non-benefit", "good", "poor" or the like. In one specific embodiment of the invention, the cancer patient for which the test is performed is a pancreas cancer patient. In this embodiment, the yeast-based immunotherapy for mutated Ras-positive cancer may take the form of GI-4000 (described in detail below) or the equivalent. In one aspect, the yeast-based immunotherapy for mutated Ras-positive cancer is administered to the patient in conjunction with gemcitabine or the equivalent. In one aspect of this embodiment of the invention, the mutated Ras-positive cancer can include, but is not limited to, pancreas cancer, non-small cell lung cancer (NSCLC), colorectal cancer (CRC), endometrial cancers, ovarian cancers, melanoma and multiple myeloma.

In one aspect, any of the above-described methods of predicting described above or elsewhere herein are considered applicable to other cancer patients, including for example, but not limited to, non-small cell lung cancer (NSCLC) patients and colorectal cancer (CRC) patients, either alone or as an adjuvant to other standard anti-cancer agents, as the mass spectral features which are useful for classification in this disclosure are believed to be associated with, among other things, regulation of cellular inflammation response, and predictive across a broad range of tumor types as explained in U.S. patent application Ser. No. 12/932,295 filed Feb. 22, 2011 and the previously cited patents of Biodesix, Inc.

The training set used in any of the methods described above or elsewhere herein is preferably in the form of class-labeled spectra from other cancer patients who obtained benefit and who did not obtain benefit from administration of the immune response generating therapy either alone or in combination with another anti-cancer therapy. The features (m/z ranges) in the patient's spectrum that are used in classification can be investigated and selected from analysis of the mass spectra of the patients forming the training set. We speculated that one or more of the features used in U.S. Pat. No. 7,736,905 and listed in Tables 3 and 4 herein, which were developed in an entirely different context of predicting NSCLC patient benefit from Epidermal Growth Factor Receptor Inhibitors (EGFR-Is) are a suitable set of features for use in the instant methods because they could relate to the hosts immunological and inflammatory response to a tumor (see US patent application publication 2011/0208433). (The precise feature values used for classification may vary from the list set forth in '905 patent and in Tables 1-4 below, e.g., depending on the spectra alignment (shift) that is performed during pre-processing of the spectra because the sample type is substantially different.) Unlike the training set used in the '905 patent (spectra from NSCLC patients that either did or did not respond to EGFR targeting drugs), the training set used in the present methods uses spectra from samples of patients who obtained benefit and who did not obtain benefit from administration of the immune response generating therapy either alone or in combination with another anti-cancer therapy. Note, that the sample type in the current application is different from serum and plasma which was described in the '905 patent. However, as explained below, there are other features in the spectra that could be used for classification from an investigation of the spectra forming the training set examples of which are given herein.

In another aspect of this disclosure, a method of treating a cancer patient is described comprising the steps of: conducting a test in accordance with any of the methods of predicting described above or elsewhere herein, and if the class label for the spectra indicates the patient is likely to benefit from the yeast-based immune response generating therapy, administering a yeast-based immune response generating therapy either alone or in combination with another anti-cancer agent to the patient.

In one aspect, the patient is additionally treated with one or more additional anti-cancer therapies, either prior to, concurrently with, or after, treatment with the yeast-based immunotherapy for cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof.

In another aspect of this disclosure, a method of treating a cancer patient with yeast-based immunotherapy for cancer is described, comprising the step of: administering yeast-based immunotherapy for cancer to a cancer patient selected by a test in accordance with any of the methods of predicting described above or elsewhere herein in which the class label for the spectra indicates the patient is likely to benefit from the yeast-based immunotherapy for cancer. In one aspect, the patient is additionally treated with one or more additional anti-cancer therapies, either prior to, concurrently with, or after, treatment with the yeast-based immunotherapy for cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof.

In yet another aspect of this disclosure, a method of treating a cancer patient with yeast-based immunotherapy for mutated Ras-positive cancer is described, comprising the steps of: conducting a test in accordance with any of the methods of predicting described above or elsewhere herein, and if the class label for the spectra indicates the patient is likely to benefit from yeast-based immunotherapy for mutated Ras-positive cancer, administering the yeast-based immunotherapy for mutated Ras-positive cancer. In this aspect of the invention, the patient has a cancer in which mutated Ras has been identified in at least some of the tumor cells from the patient. In one aspect, the patient is additionally treated with one or more additional anti-cancer therapies, either prior to, concurrently with, or after, treatment with the yeast-based immunotherapy for mutated Ras-positive cancer. In one embodiment, the yeast-based immunotherapy for mutated Ras-positive cancer is a product in the series of yeast-based immunotherapy products known as GI-4000, or the equivalent. In one aspect of this embodiment of the invention, the mutated Ras-positive cancer can include, but is not limited to, pancreas cancer, non-small cell lung cancer (NSCLC), colorectal cancer (CRC), endometrial cancers, ovarian cancers, melanoma and multiple myeloma. In one aspect, the cancer is pancreas cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof. In one aspect, the yeast-based immunotherapy for mutated Ras-positive cancer is administered to the patient in conjunction with gemcitabine or the equivalent. In one embodiment, the patient is a pancreas cancer patient and the therapy comprises a product in the series of yeast-based immunotherapy products known as GI-4000 or the equivalent (described in detail below), either alone or in combination with gemcitabine or the equivalent. In one aspect, the cancer patient's tumor has been surgically resected prior to treatment with the yeast-based immunotherapy composition.

In another aspect of this disclosure, a method of treating a cancer patient with yeast-based immunotherapy for cancer is described, comprising the step of: administering yeast-based immunotherapy for mutated Ras-positive cancer to a cancer patient selected by a test in accordance with any of the methods of predicting described above or elsewhere herein in which the class label for the spectra indicates the patient is likely to benefit from the yeast-based immunotherapy for mutated Ras-positive cancer. In this aspect of the invention, the patient has a cancer in which mutated Ras has been identified in tumor cells from the patient. In one aspect, the patient is additionally treated with one or more additional anti-cancer therapies, either prior to, concurrently with, or after, treatment with the yeast-based immunotherapy for mutated Ras-positive cancer. In one embodiment, the yeast-based immunotherapy for mutated Ras-positive cancer is a product in the series of yeast-based immunotherapy products known as GI-4000, or the equivalent. In one aspect of this embodiment of the invention, the mutated Ras-positive cancer can include, but is not limited to, pancreas cancer, non-small cell lung cancer (NSCLC), colorectal cancer (CRC), endometrial cancers, ovarian cancers, melanoma and multiple myeloma. In one aspect, the cancer is pancreas cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof. In one aspect, the yeast-based immunotherapy for mutated Ras-positive cancer is administered to the patient in conjunction with gemcitabine or the equivalent. In one embodiment, the patient is a pancreas cancer patient and the therapy comprises a product in the series of yeast-based immunotherapy products known as GI-4000 or the equivalent, either alone or in combination with gemcitabine or the equivalent. In one aspect, the cancer patient's tumor has been surgically resected prior to treatment with the yeast-based immunotherapy composition.

In any of the aspects of a method to treat a patient with cancer using a yeast-based immunotherapy, the yeast-based immunotherapy can include, but is not limited to, a whole, heat-inactivated recombinant yeast that has expressed at least one cancer antigen associated with or expressed by the patient's tumor. In one aspect, the yeast can be from a genus of yeast including, but not limited to, *Saccharomyces*. In one aspect, the yeast can be from a species of yeast including, but not limited to, *Saccharomyces cerevisiae*.

In another aspect, a system is disclosed for predicting whether a cancer patient is likely to benefit from administration of a yeast-based immune response generating therapy either alone or in combination with another anti-cancer agent. The system includes a mass spectrometer generating a mass spectrum from a blood-derived sample from the cancer patient. The system also includes a machine-readable memory storing a training set of class-labeled spectra from other cancer patients. The training set includes class-labeled spectra from plurality of patients that did not benefit from yeast-based immune response generating therapy either alone or in combination with another anti-cancer agent and class-labeled spectra from plurality of patients that did benefit from the cellular immunotherapy either alone or in combination with the another anti-cancer agent. The system further includes a computer system configured to operate on the mass spectrum and classify the mass spectrum using the training set, producing a class label for the mass spectrum, wherein the class label is used to predict whether the patient is likely to benefit from administration of the yeast-based immune response generating therapy either alone or in combination with another anti-cancer agent.

In another aspect, a system is disclosed for predicting whether a cancer patient is likely to benefit from administration of yeast-based immunotherapy for cancer, either alone or in conjunction with treatment with another anti-cancer therapy. The system includes a mass spectrometer generating a mass spectrum from a blood-derived sample from the cancer patient. The system also includes a machine-readable memory storing a training set of class-labeled spectra from other cancer patients. The training set includes class-labeled spectra from plurality of patients that did not benefit from the yeast-based immunotherapy for cancer either alone or in conjunction with treatment with another anti-cancer therapy and class-labeled spectra from plurality of patients that did benefit from the yeast-based immunotherapy for cancer either alone or in conjunction with treatment with the another anti-cancer therapy. The system further includes a computer system configured to operate on the mass spectrum and classify the mass spectrum using the training set, producing a class label for the mass spectrum, wherein the class label is used to predict whether the patient is likely to benefit from administration of the yeast-based immunotherapy for cancer either alone or in conjunction with treatment with another anti-cancer therapy.

In another aspect, a system is disclosed for predicting whether a cancer patient is likely to benefit from administration of yeast-based immunotherapy for mutated Ras-positive cancer, either alone or in conjunction with treatment with another anti-cancer therapy. The system includes a mass spectrometer generating a mass spectrum from a blood-derived sample from the cancer patient. The system also includes a machine-readable memory storing a training set of class-labeled spectra from other cancer patients. The training set includes class-labeled spectra from plurality of patients that did not benefit from the yeast-based immunotherapy for mutated Ras-positive cancer either alone or in conjunction with treatment with another anti-cancer therapy and class-labeled spectra from plurality of patients that did benefit from the yeast-based immunotherapy for mutated Ras-positive cancer either alone or in conjunction with treatment with the another anti-cancer therapy. The system further includes a computer system configured to operate on the mass spectrum and classify the mass spectrum using the training set, producing a class label for the mass spectrum, wherein the class label is used to predict whether the patient is likely to benefit from administration of the yeast-based immunotherapy for mutated Ras-positive cancer either alone or in conjunction with treatment with another anti-cancer therapy. In one aspect, the yeast-based immunotherapy for mutated Ras-positive cancer is a product within the series of products known as GI-4000. In one aspect, the mutated Ras-positive cancer is selected from pancreas cancer, non-small cell lung cancer (NSCLC), colorectal cancer (CRC), endometrial cancers, ovarian cancers, melanoma and multiple myeloma. In one aspect, the cancer is pancreas cancer.

BRIEF DESCRIPTION OF THE DRAWINGS

The following detailed description will make reference to the appended drawings, which are offered by way of example and not limitation, and in which:

FIGS. 2A and 2B are Kaplan-Meier plots or recurrence free survival (RFS) and overall survival (OS) illustrating ability of a mass spectrometry method of this disclosure to identify patients which are likely to benefit from the combination of GI-4000 and gemcitabine in the treatment of pancreatic cancer.

In FIGS. 3A-3B, the value of K was 1, in FIGS. 3C and 3D the value of K was 3 and in 3E and 3F the value of K was 5. The plots show the ability of the applicant's classifier to separate, in the treatment arm (patients treated with both gemcitabine and GI-4000), patients which benefited from those that did not, and moreover that some patients in the treatment arm did worse than some patients in the control arm. Therefore, the plots demonstrate the ability of the applicant's mass spectral method to both predict those patients that are likely to benefit from the treatment with immune response generating therapies as well as those patients that are not likely to benefit from the treatment with immune response generating therapies.

FIGS. 4A-4B, 4C-4D, 4E-4F, and 4G-4H each represent plots for RFS and OS from four different classifiers, respectively, based on different sets of peaks in mass spectra used for classification.

FIG. 10B is a plot of Hazard ratios for the Test Set used in cross validation analyses for various values of K used in the K-nearest neighbor classifier.

FIG. 11 is a flow chart of a testing method for predicting cancer patient benefit, or non-benefit from immune response generating therapies either alone or in combination with other anti-cancer agents.

FIGS. 13A-13B, 13C-13D, 13E-13F, 13G-13H, 13I-13J, and 13K-13L each represent plots for RFS and OS from six different classifiers, respectively, based on different sets of peaks or features in mass spectra used for classification.

In FIG. 16D, a portion of the spectrum in an m/z range from 7140 to 7890 Da is shown enlarged in the inset of FIG. 16D showing a wealth of spectral information obtained at approximately 500,000 shots. In FIG. 16E, the spectrum is shown in the inset with the Y axis amplified in order to show additional spectral information and peaks in the region of m/z around 9520, which are revealed with the DeepMALDI method but which are not visible in a typical ~1,000 shot spectrum.

DETAILED DESCRIPTION, WORKING EXAMPLES AND EXPERIMENTAL RESULTS

Figure 1:
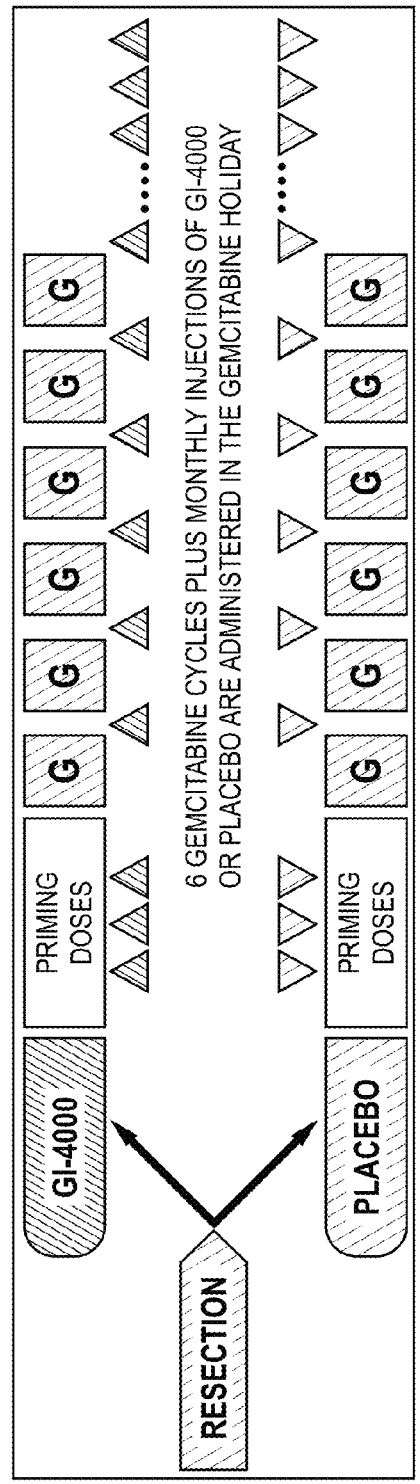
FIG. 1 is a schematic drawing showing the design of a Phase 2 clinical trial in pancreas cancer using GlobeImmune's yeast-based immunotherapy product series targeting mutated Ras-positive cancers, known as GI-4000.

Described herein are predictive tests for immune response generating therapies, related classifiers and systems and treatment of patients identified by these tests, classifiers and systems.

In particular, methods are described herein for predicting, in advance of treatment, whether a cancer patient is likely or not likely to benefit from administration of a yeast-based immune response generating therapy, either alone or in combination with another anti-cancer therapy. Methods are also described herein for predicting, in advance of treatment, whether a cancer patient is likely or not likely to benefit from administration of yeast-based immunotherapy for mutated Ras-positive cancer (e.g., GI-4000 described herein), including, but not limited to, pancreas cancer. The methods of the invention are based on mass spectrometry of a blood-derived sample (e.g., serum or plasma) obtained pre-treatment, and classification based on the proteomic signature in the sample revealed by mass spectrometry. The use of blood-derived samples is significant, as it increases the likelihood of measuring global susceptibility to immunotherapy by giving insight into circulating markers of the immune system. Furthermore, the methods can be conducted quickly via a simple mass spectrometry test from a blood-derived sample, without the need for performing complex, time consuming assays of a patient sample or obtaining a tumor sample from the patient. The tests are useful in that, if the patient is predicted to be likely to benefit the treatment can proceed with some confidence that the patient will have an improved outcome, whereas if the patient is predicted in advance that they are not likely to benefit, the patient can be steered towards other treatments in which the patient is likely to derive benefit, or other treatment options can be considered.

Methods are also described herein for treating a patient with a yeast-based immune response generating therapy for cancer, either alone or in combination with another anti-cancer agent, where the patient has first been selected by a method or test in accordance with any of the methods of predicting described above or elsewhere herein to be likely to benefit from the immune response generating therapy for cancer (e.g., the class label for the spectra generated in the test or method indicates the patient is likely to benefit from the immune response generating therapy for cancer).

Methods are also described herein for treating a patient with yeast-based immunotherapy for mutated Ras-positive cancer (e.g., GI-4000 described herein), either alone or in combination with another anti-cancer agent, where the patient has first been selected by a method or test in accordance with any of the methods of predicting described above or elsewhere herein to be likely to benefit from the yeast-based immunotherapy for mutated Ras-positive cancer (e.g., the class label for the spectra generated in the test or method indicates the patient is likely to benefit from the yeast-based immunotherapy for mutated Ras-positive cancer). In any of these methods of treating of the invention, the method includes a step of administering the yeast-based immune response generating therapy (which may include, but is not limited to, a yeast-based immunotherapy for mutated Ras-positive cancer) to a subject that has a cancer expressing the cancer antigen, and who has been identified or selected as likely to benefit from administration of the composition by a test performed in accordance with any of the methods of predicting of the invention as described herein.

A Working Example Describing GI-4000-02: A Phase 2b Clinical Trial for GI-4000 and Gemcitabine in Pancreas Cancer GI-4000-02 is a fully-enrolled Phase 2b randomized, double-blind, placebo-controlled, multi-center, adjuvant clinical trial of GI-4000 plus gemcitabine or placebo plus gemcitabine in patients with R0 or R1 resected pancreas cancer (see FIG. 1). An R0 resection is defined by the absence of microscopic residual disease at the surgical margin. An R1 resection is defined by the presence of microscopic residual disease at the surgical margin. R0 and R1 patients have different expected survival rates, with R0 patients living longer on average. In this clinical trial, a sample of tumor tissue was obtained from each subject during the screening period and the tumor was evaluated for the presence of a Ras mutation. If a subject had a product-related mutation, then the GI-4000 yeast-based immunotherapy product that matched the specific Ras mutation in the subject's tumor was administered (the GI-4000 series is described in detail below).

The study population consisted of 176 subjects with Ras mutated resected pancreas cancer enrolled at 39 centers in the United States and five international centers. Following resection, subjects were prospectively stratified into two groups by resection status, and both the R1 and R0 groups were randomly assigned into two treatment groups at a one-to-one ratio to receive either 40Y.U. of GI-4000 ("Y.U." is a "Yeast Unit" or "yeast cell equivalent; one Y.U.=10 million yeast cells) plus gemcitabine or placebo plus gemcitabine. Thirty-nine R1 subjects were enrolled, of whom 19 were assigned to the GI-4000 plus gemcitabine group and 20 were assigned to the placebo plus gemcitabine group. One hundred thirty-seven R0 subjects were enrolled, of whom 69 were assigned to the GI-4000 plus gemcitabine group and 68 were assigned to the placebo plus gemcitabine group. The 40 Y.U. dose of GI-4000 was administered as four separate 10Y.U. subcutaneous injections, one in each arm and leg. Subjects were given three weekly doses of either GI-4000 or placebo between resection and the initiation of gemcitabine therapy. All subjects were administered up to six monthly cycles of gemcitabine beginning between six and eight weeks after resection. Monthly doses of GI-4000 or placebo were given after each cycle of gemcitabine to coincide with the scheduled breaks in monthly gemcitabine treatment. Monthly administration of GI-4000 or placebo continued until subjects withdrew from the study, experienced disease recurrence or died. A number of disease-specific baseline characteristics were evaluated, including the following prognostic factors, which have been shown to have an impact on outcome: (a) Lymph node status was defined by the presence or absence of microscopic evidence of pancreas cancer cells. Positive nodes are considered a poor prognostic indicator; (b) Performance status, which consists of a five point scale (0, 1, 2, 3, 4) that reflects the general health of the patients, with 0 being the most favorable status and 4 being the least favorable; (c) CA19-9, which is a blood biomarker of pancreas cancer cells that serves as a measure of tumor burden. Higher CA19-9 levels are associated with poorer clinical outcomes; (d) Tumor size in centimeters, with larger size generally associated with poorer outcomes; and (e) Tumor stage, which ranges from Stage I through IV and is defined based on a standardized scoring system that consists of primary tumor size, extent of local invasion, extent of involvement of regional lymph nodes and systemic spread of the cancer away from the primary tumor.

The primary endpoint for this clinical trial was recurrence-free survival. Secondary endpoints included overall survival, immune responses and biomarkers of disease burden, such as CA19-9. To date, GI-4000 in combination with adjuvant gemcitabine has shown evidence of a clinically meaningful effect on survival in Ras-mutation positive R1 pancreas cancer subjects, including: (a) 2.6 month improvement in median OS (17.2 months compared to 14.6 months); an 18% relative improvement; (b) 5.0 month improvement in median OS for GI-4000 immune responders (19.6 months compared to 14.6 months); a 34% relative improvement; (c) 16% advantage in one-year survival (72% vs. 56%); a 30% relative improvement; and (d) 1 month improvement in median RFS (9.6 months for GI-4000/gemcitabine vs. 8.5 months); a 13% relative advantage. In addition, GI-4000 was immunogenic and well tolerated in R1 subjects: (a) 7/15(47%) in the GI-4000/gem arm vs. 1/12(8%) in the placebo/gem arm had Ras mutation specific T cell response; and (b) GI-4000 has been well tolerated to date with no evidence of significant novel toxicities. Additional results were observed following the development of a predictive mass spectral method of the invention, which will be described in detail below.

Predictive Mass Spectral Methods

An example of the mass-spectral methods of this disclosure will be described below in detail in conjunction with a study of samples in the GI-4000+gemcitabine Phase 2b clinical trial in pancreas cancer described above. Some, but not all patients receiving the combination of GI-4000+gemcitabine experienced a substantial improvement in RFS and OS as compared to those patients that received gemcitabine and placebo. A classifier was developed to predict in advance of treatment whether a patient is a member of the class of patient that is likely to benefit ("Slow" in the following discussion), or conversely is not likely to benefit ("Quick" in the following discussion). FIGS. 2A and 2B are Kaplan-Meier plots of recurrence-free survival (RFS) and overall survival (OS), of patients positive for a proteomic signature indicating they are likely to benefit from GI-4000 in combination with gemcitabine. FIG. 2A shows RFS by treatment group (GI-4000 vs. placebo) for subjects with the late recurrence ("Slow") proteomic signature, whereas FIG. 2B shows OS by treatment group for subjects with the late recurrence proteomic signature. The plots illustrate the ability of a mass spectrometry method of this disclosure to identify patients which are likely to benefit from the combination of GI-4000 and gemcitabine in the treatment of pancreatic cancer. Further Kaplan-Meier plots from our study showing the ability of our method to identify patients in the treatment arm that did or did not obtain benefit from the combination of GI-4000 and gemcitabine will be discussed in conjunction with FIGS. 3 and 4 below.

In our study, samples suitable for generation of mass spectra were available from 90 patients enrolled in GI-4000-02, described in detail above. The samples were derived from blood, and in this particular case were plasma that had been obtained from whole blood by a prior density-based separation method. Whole blood (in sodium heparin glass tubes) was received at GlobeImmune laboratories from clinical trial sites by overnight delivery at room temperature and was processed within 30 hr. of collection. To separate peripheral blood mononuclear cells (PBMCs), blood was diluted approximately 1:1 with Dulbecco's phosphate buffered saline (D-PBS; Gibco/InVitrogen catalog #14190-250), layered onto a Ficoll-Hypaque gradient in Leucosep™ tubes (Greiner) and centrifuged at 1000×g for 10 minutes at ambient temperature. Before cells were harvested from the gradients, the plasma diluted 1:1 with D-PBS was aspirated off and frozen at minus 80° C. Prior to use in the mass spectra methods of the invention, the samples were thawed, aliquoted and then refrozen once before use.

Spectra were generated from the samples using the standard dilute-and-shoot (DNS) method and the "DeepMALDI" method, described in pending U.S. Provisional Application Ser. No. 61/652,394 filed May 29, 2012, incorporated by reference herein, and described in further detail below.

We performed the VeriStrat test as described in U.S. Pat. No. 7,736,905 and the previously-cited patent literature of Biodesix, Inc. on the dilute-and-shoot spectra, but found that the classifier did not yield useful information. Few VeriStrat Poor samples were identified and no significant differences were found between VeriStrat Good and Poor patients in either treatment arm.

Hence, a new classifier with a new training set needed to be defined. We speculated that VeriStrat features might be useful, because we believe that these are related to the host's immune and inflammatory response to the presence of cancer (See US patent application publication 2011/0208433). Indeed, it was discovered that mass spectral features in the spectra used in the VeriStrat test (see Tables 3 and 4, below) could be used for classification in the pancreatic cancer study provided that the classifier training set was properly defined and the spectral pre-processing procedures changed, as described below. This discovery of the classifier design and training set will be described in the following section.

Classifier Design

The starting point for designing a classifier to split patients into those with better and worse prognosis on the GI-4000 treatment was to define a training set of patients with better and worse recurrence-free survival (RFS). Based on the distribution of times of RFS, it was decided to define patients with quick recurrence ("Quick") as those patients recurring before 276 days and patients with slow recurrence ("Slow") as those patients without a recurrence event before 500 days. This gave a training set of 20 patients in the "Quick" group and 14 patients in the "Slow" group, with 9 patients with intermediate RFS times. (Aside: In fact there were 21 patients with RFS event before 276 days, but the spectrum for one of these patients was missed when starting the project, so this patient was not initially included in the training set for the "dilute-and-shoot" and 150,000 shot DeepMALDI analysis, and was only used when the classifier was applied to the whole cohort. For the 500,000 shot DeepMALDI analysis, this patient was included in the training set and one patient with long recurrence time was excluded, as it was determined that the plasma sample for this patient had been taken during treatment.) It would be possible to produce similar results by taking different cutoff points to define the "Slow" and "Quick" groups or to define them by quick and slow times to death.

Having defined the training set of "Quick" and "Slow" groups, the mass spectra to be compared were pre-processed using the methods of U.S. Pat. No. 7,736,905, including background subtraction, partial ion current normalization, and spectral alignment. The details of the pre-processing are different for the Dilute-and-Shoot spectra and the Deep-MALDI spectra, although the general procedure is similar. First the background is estimated and subtracted from the spectra. The spectra are normalized to partial ion current. The regions used in calculating partial ion current can be chosen in various ways, as long as they exclude the strong and most variable peaks in the mass spectra. In the example dilute-and-shoot classifier for which results are given below, the regions used for partial ion current calculation and normalization were 3 kDa-11.4 kDa, 13 kDa-15 kDa and 16.1 kDa-30 kDa, but other choices could be made. For example, for the 500,000 shot DeepMALDI spectra-based classifiers the regions used for partial ion current normalization were 4.9 kDa-6.54 kDa, 12 kDa-13.5 kDa and 18 kDa-27 kDa. The noise in the spectra is estimated. Once the peaks are detected in the spectra, the spectra can be aligned using a set of alignment points. A set of alignment points can be compiled by choosing a subset of the peaks detected in the spectra that are common to most of the spectra to be aligned or can be chosen beforehand from peaks that are known to exist in most spectra from prior experience. In the case of the dilute-and-shoot classifier shown below, the following alignment points were selected from prior experience. These were peaks at the following m/z positions: 6434.5, 6632.1, 11686.9, 12864.8, 15131.1, 15871.5, and 28102.5. It is worth noting that, if the DeepMALDI methods for obtaining mass spectral data from the samples (see explanation below) are used, other features in the spectra could be used for partial ion current normalization and spectral alignment and pre-processing methods for background subtraction more suitable for the DeepMALDI spectra may be used. For example, in the 500,000 shot Deep-MALDI spectra-based classifiers presented below, the following alignment points were used: 3315, 4153, 4457, 4710, 4855, 5289, 6431, 6629, 6835, 7561, 7931, 8202, 8807, 8912, 9707, 12856, 13735, 14031, 14134, 15117, 15856, 17366, 21046, 27890, 28019, 28067, and 28228. It should be noted, however, that other choices of number and location of alignment points are possible for both methods of spectral acquisition.

Pre-processing the spectra renders them comparable with one another and they can then be used to make a classifier, based on features that are defined from external consideration, or the groups of spectra can be compared to determine features that are differentially expressed between the groups, a subset of these features can then be selected and a classifier built using this set of features. One of the classifiers with results shown below was constructed using features determined from external considerations.

As it is believed that the mass spectral features used in the VeriStrat classifier (see Tables 3 and 4 below) are correlated with inflammatory processes linked to the host response to the presence of the tumor (see our prior U.S. patent application Ser. No. 12/932,295 filed Feb. 22, 2011, incorporated by reference herein) and that this is related to the response of the immune system to the tumor, it was of interest to try using the eight VeriStrat features with a new reference set of spectra defined from patients' recurrence times following GI-4000 treatment. The results are shown in FIG. 3, described below. However, other classifiers could be constructed using features found to differentiate between the two reference set groups during their comparison. For dilute-and-shoot spectra these features include one or more of the following:

TABLE 1

| m/Z center of feature | m/Z left edge of feature | m/Z right edge of feature |
| --- | --- | --- |
| 5841.168 | 5831.035 | 5851.302 |
| 6433.537 | 6427.831 | 6439.244 |
| 8765.432 | 8757.666 | 8773.197 |
| 9669.883 | 9618.946 | 9720.82 |
| 11442.47 | 11428.45 | 11456.49 |
| 11474.93 | 11460.88 | 11488.99 |
| 11529.59 | 11518.95 | 11540.22 |
| 11696.79 | 11650.43 | 11743.15 |
| 11900.24 | 11878.99 | 11921.49 |
| 12865.48 | 12856.36 | 12874.6 |

One or more of the features of Table 1 could be used in combination with features in Tables 2, 3 and 5 for use in classifier.

For 150,000 shot "DeepMALDI" spectra, the features useful for classification include the following:

TABLE 2

| Peak # | m/z center | m/z left edge | m/z right edge |
| --- | --- | --- | --- |
| 1 | 3039.529 | 3037.053 | 3042.005 |
| 2 | 3366.615 | 3358.219 | 3375.011 |
| 3 | 3432.149 | 3412.777 | 3451.52 |
| 4 | 3473.153 | 3453.337 | 3492.969 |
| 5 | 3552.474 | 3543.957 | 3560.992 |
| 6 | 3680.091 | 3672.995 | 3687.187 |
| 7 | 3842.836 | 3836.58 | 3849.092 |
| 8 | 4203.838 | 4193.707 | 4213.969 |
| 9 | 5180.126 | 5176.524 | 5183.728 |
| 10 | 5291.206 | 5287.73 | 5294.682 |
| 11 | 5700.687 | 5689.381 | 5711.994 |
| 12 | 5843.129 | 5840 | 5846.258 |
| 13 | 5860.729 | 5851.114 | 5870.344 |
| 14 | 5866.576 | 5862.227 | 5870.926 |
| 15 | 6008.828 | 6004.271 | 6013.384 |
| 16 | 6192.594 | 6182.541 | 6202.648 |
| 17 | 6298.994 | 6294.655 | 6303.333 |
| 18 | 6873.363 | 6870.128 | 6876.598 |
| 19 | 6903.79 | 6894.561 | 6913.018 |
| 20 | 6971.019 | 6967.629 | 6974.408 |
| 21 | 6985.879 | 6982.461 | 6989.296 |
| 22 | 6995.012 | 6991.486 | 6998.538 |
| 23 | 7009.091 | 7002.267 | 7015.914 |
| 24 | 7023.426 | 7019.431 | 7027.422 |
| 25 | 7035.244 | 7031.664 | 7038.825 |
| 26 | 7045.484 | 7041.962 | 7049.005 |
| 27 | 7057.527 | 7050.655 | 7064.399 |
| 28 | 7074.719 | 7070.399 | 7079.039 |
| 29 | 7150.539 | 7136.65 | 7164.429 |
| 30 | 7245.544 | 7237.996 | 7253.093 |
| 31 | 7301.145 | 7297.011 | 7305.279 |
| 32 | 7783.506 | 7778.087 | 7788.925 |
| 33 | 8361.169 | 8355.605 | 8366.734 |
| 34 | 8476.978 | 8470.468 | 8483.489 |
| 35 | 8767.557 | 8761.746 | 8773.368 |
| 36 | 9362.525 | 9353.951 | 9371.098 |
| 37 | 9671.94 | 9664.199 | 9679.681 |
| 38 | 9759.032 | 9751.081 | 9766.982 |
| 39 | 9788.134 | 9772.707 | 9803.561 |
| 40 | 9871.152 | 9861.387 | 9880.918 |
| 41 | 11302.64 | 11295.53 | 11309.76 |
| 42 | 10485.61 | 10471.48 | 10499.73 |
| 43 | 10776.72 | 10762.23 | 10791.21 |
| 44 | 11475.86 | 11468.27 | 11483.45 |
| 45 | 11494.79 | 11487.31 | 11502.27 |
| 46 | 11529.86 | 11522.63 | 11537.1 |
| 47 | 11555.31 | 11541.01 | 11569.61 |
| 48 | 11655.18 | 11616.93 | 11693.44 |
| 49 | 11709.95 | 11701.41 | 11718.49 |
| 50 | 11761.94 | 11724.72 | 11799.16 |
| 51 | 11858.02 | 11814.24 | 11901.79 |
| 52 | 11909.8 | 11902.01 | 11917.58 |
| 53 | 11939.01 | 11929.83 | 11948.2 |
| 54 | 12348.32 | 12339.42 | 12357.22 |
| 55 | 12866.6 | 12858.57 | 12874.62 |
| 56 | 13072.62 | 13064.42 | 13080.81 |
| 57 | 13090.91 | 13082.14 | 13099.68 |
| 58 | 13360.65 | 13351.7 | 13369.59 |
| 59 | 13807.33 | 13786.47 | 13828.18 |
| 60 | 13913.92 | 13897.53 | 13930.32 |
| 61 | 14043.98 | 14035.87 | 14052.09 |
| 62 | 14092.28 | 14084.11 | 14100.46 |
| 63 | 14125.28 | 14117.13 | 14133.43 |
| 64 | 14148.15 | 14139.99 | 14156.32 |
| 65 | 14197.84 | 14181.99 | 14213.69 |
| 66 | 14258.28 | 14249.88 | 14266.69 |
| 67 | 14429.84 | 14414.32 | 14445.35 |
| 68 | 14384.69 | 14357.6 | 14411.78 |
| 69 | 14530.4 | 14520.1 | 14540.7 |
| 70 | 18801.94 | 18784.71 | 18819.18 |
| 71 | 18861.88 | 18844.22 | 18879.55 |
| 72 | 18904.03 | 18884.67 | 18923.4 |
| 73 | 19860.06 | 19771.09 | 19949.03 |
| 74 | 21710.89 | 21683.49 | 21738.29 |
| 75 | 22998.95 | 22839.61 | 23158.29 |
| 76 | 28314 | 28282.63 | 28345.37 |
| 77 | 28518.76 | 28486.77 | 28550.75 |

For 500,000 shot DeepMALDI spectra, the features useful for classification include the following:

TABLE 5

| | m/z center | m/z left edge | m/z right edge |
|---|---|---|---|
| 1 | 3463.350 | 3459.400 | 3467.300 |
| 2 | 3609.960 | 3605.630 | 3614.280 |
| 3 | 3679.430 | 3674.080 | 3684.770 |
| 4 | 3840.800 | 3834.810 | 3846.780 |
| 5 | 3892.750 | 3889.050 | 3896.440 |
| 6 | 4077.700 | 4072.100 | 4083.300 |
| 7 | 4492.020 | 4485.400 | 4498.640 |
| 8 | 4597.040 | 4592.710 | 4601.370 |
| 9 | 5405.660 | 5400.820 | 5410.500 |
| 10 | 5555.430 | 5549.440 | 5561.410 |
| 11 | 5582.800 | 5578.980 | 5586.620 |
| 12 | 5635.590 | 5631.640 | 5639.530 |
| 13 | 5706.610 | 5701.520 | 5711.700 |
| 14 | 5762.000 | 5758.050 | 5765.940 |
| 15 | 5840.660 | 5836.580 | 5844.730 |
| 16 | 5873.770 | 5870.200 | 5877.330 |
| 17 | 5890.570 | 5885.730 | 5895.410 |
| 18 | 6107.260 | 6102.290 | 6112.220 |
| 19 | 6129.670 | 6125.720 | 6133.610 |
| 20 | 6328.570 | 6323.730 | 6333.410 |
| 21 | 6892.580 | 6888.250 | 6896.900 |
| 22 | 6951.990 | 6948.040 | 6955.930 |
| 23 | 6981.660 | 6977.580 | 6985.730 |
| 24 | 7004.170 | 6999.330 | 7009.000 |
| 25 | 7054.210 | 7048.220 | 7060.190 |
| 26 | 7153.620 | 7148.910 | 7158.330 |
| 27 | 7295.310 | 7289.320 | 7301.290 |
| 28 | 7421.920 | 7417.970 | 7425.870 |
| 29 | 8357.210 | 8351.730 | 8362.680 |
| 30 | 8762.290 | 8756.430 | 8768.140 |
| 31 | 8992.440 | 8987.350 | 8997.530 |
| 32 | 9199.780 | 9193.160 | 9206.400 |
| 33 | 9794.720 | 9791.280 | 9798.160 |
| 34 | 10000.020 | 9993.530 | 10006.510 |
| 35 | 10018.610 | 10013.260 | 10023.960 |
| 36 | 10090.630 | 10083.880 | 10097.370 |
| 37 | 10174.760 | 10168.520 | 10181.000 |
| 38 | 10200.610 | 10191.950 | 10209.270 |
| 39 | 10657.440 | 10651.960 | 10662.910 |
| 40 | 10713.840 | 10704.160 | 10723.510 |
| 41 | 10912.750 | 10905.490 | 10920.000 |
| 42 | 11402.140 | 11396.410 | 11407.870 |
| 43 | 11432.410 | 11425.280 | 11439.540 |
| 44 | 11466.160 | 11459.660 | 11472.650 |
| 45 | 11488.190 | 11481.820 | 11494.550 |
| 46 | 11520.580 | 11514.720 | 11526.430 |
| 47 | 11543.880 | 11538.400 | 11549.350 |
| 48 | 11563.080 | 11556.070 | 11570.080 |
| 49 | 11620.250 | 11613.120 | 11627.380 |
| 50 | 11676.220 | 11670.870 | 11681.570 |
| 51 | 11699.260 | 11694.040 | 11704.480 |
| 52 | 11723.200 | 11716.450 | 11729.950 |
| 53 | 11744.210 | 11739.370 | 11749.050 |
| 54 | 11775.740 | 11767.330 | 11784.140 |
| 55 | 11821.600 | 11814.600 | 11828.600 |
| 56 | 11839.680 | 11833.950 | 11845.410 |
| 57 | 11882.560 | 11877.850 | 11887.270 |
| 58 | 11900.770 | 11894.660 | 11906.880 |
| 59 | 12401.800 | 12392.760 | 12410.840 |
| 60 | 12975.720 | 12968.730 | 12982.740 |
| 61 | 13104.010 | 13098.150 | 13109.860 |
| 62 | 13145.130 | 13138.380 | 13151.880 |
| 63 | 13399.430 | 13388.090 | 13410.760 |
| 64 | 13475.490 | 13468.100 | 13482.870 |
| 65 | 13622.780 | 13616.670 | 13628.890 |
| 66 | 13648.070 | 13642.590 | 13653.540 |
| 67 | 13677.100 | 13670.860 | 13683.340 |
| 68 | 13735.490 | 13731.670 | 13739.310 |
| 69 | 13781.970 | 13774.960 | 13788.970 |
| 70 | 13800.220 | 13794.870 | 13805.570 |
| 71 | 14007.100 | 14002.010 | 14012.190 |
| 72 | 14030.530 | 14023.400 | 14037.660 |
| 73 | 14057.140 | 14051.410 | 14062.870 |
| 74 | 14078.920 | 14073.060 | 14084.770 |

TABLE 5-continued

| | m/z center | m/z left edge | m/z right edge |
|---|---|---|---|
| 75 | 14096.180 | 14091.340 | 14101.020 |
| 76 | 14112.220 | 14107.890 | 14116.550 |
| 77 | 14137.690 | 14129.540 | 14145.840 |
| 78 | 14186.020 | 14178.130 | 14193.910 |
| 79 | 14244.340 | 14232.110 | 14256.560 |
| 80 | 14280.730 | 14272.960 | 14288.490 |
| 81 | 14408.640 | 14403.290 | 14413.980 |
| 82 | 14423.030 | 14418.310 | 14427.740 |
| 83 | 14436.400 | 14431.050 | 14441.740 |
| 84 | 14518.120 | 14508.310 | 14527.920 |
| 85 | 14537.850 | 14531.740 | 14543.960 |
| 86 | 14653.490 | 14645.820 | 14661.150 |
| 87 | 14715.700 | 14706.780 | 14724.610 |
| 88 | 15618.160 | 15597.660 | 15638.660 |
| 89 | 17443.590 | 17430.700 | 17456.470 |
| 90 | 18734.930 | 18724.840 | 18745.010 |
| 91 | 21675.550 | 21649.880 | 21701.220 |
| 92 | 22987.930 | 22971.630 | 23004.220 |
| 93 | 23020.930 | 23009.110 | 23032.740 |
| 94 | 28038.090 | 27994.740 | 28081.430 |
| 95 | 28231.950 | 28203.250 | 28260.650 |
| 96 | 28438.910 | 28393.220 | 28484.590 |
| 97 | 28804.560 | 28750.090 | 28859.030 |

Note that improvements to normalization of spectra may reveal still further differentiating peaks, hence the above lists are not considered exhaustive. Again, the precise m/z location is subject to slight shift depending on spectral alignment during pre-processing.

A. Dilute-and-Shoot Spectra-Based Classifiers

Figure 3A:
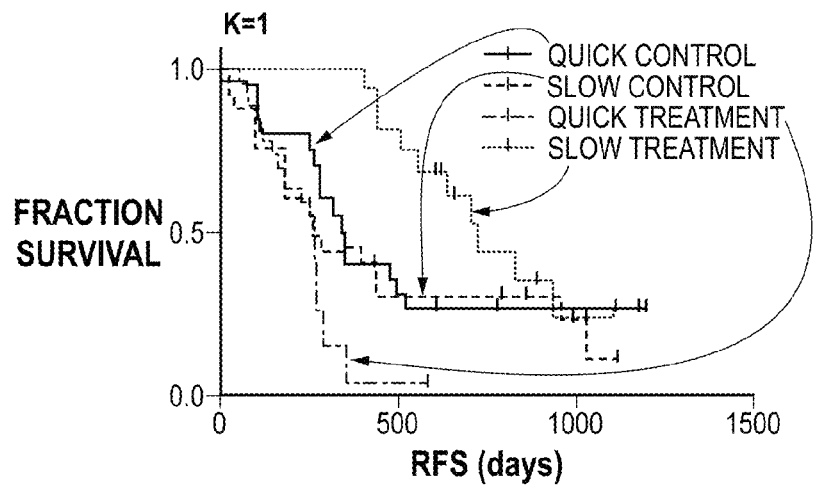
FIGS. 3A-3F are pairs of Kaplan-Meier plots of RFS and OS for patients in both the treatment and control arms in the study of GI-4000 and gemcitabine in the treatment of pancreatic cancer for different values of K used in a K-nearest neighbor classification algorithm.
Figure 3B:
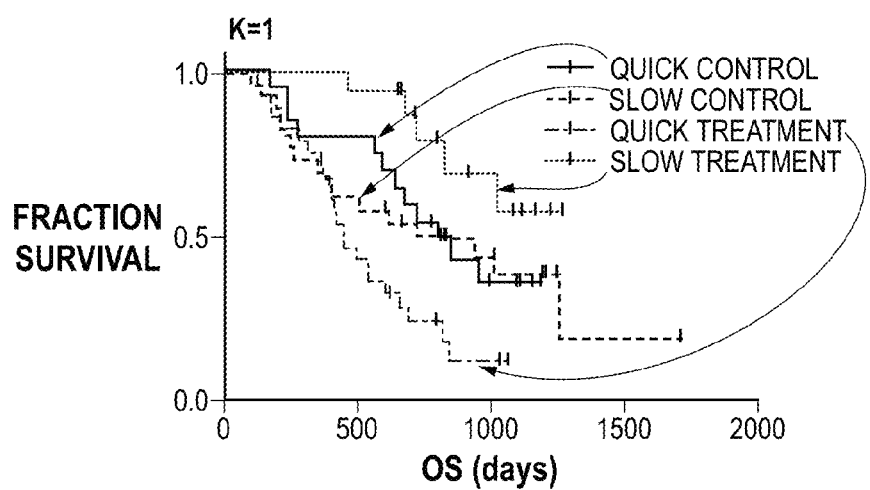
Figure 3C:
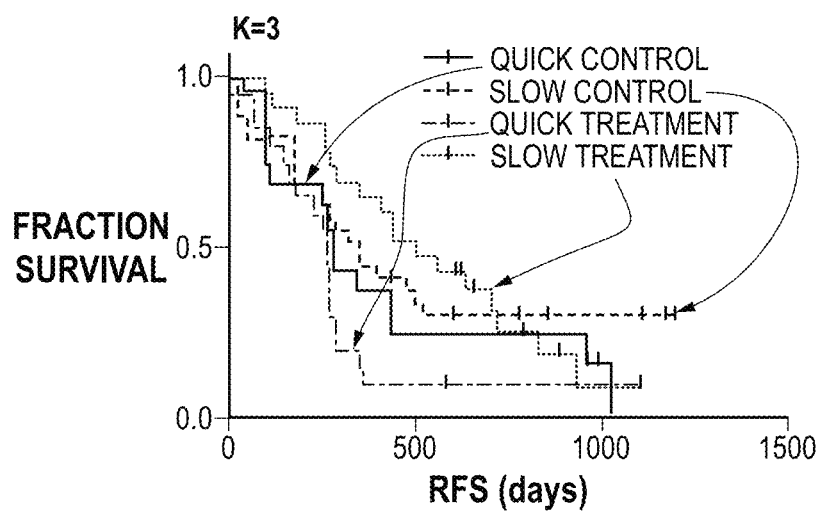
Figure 3D:
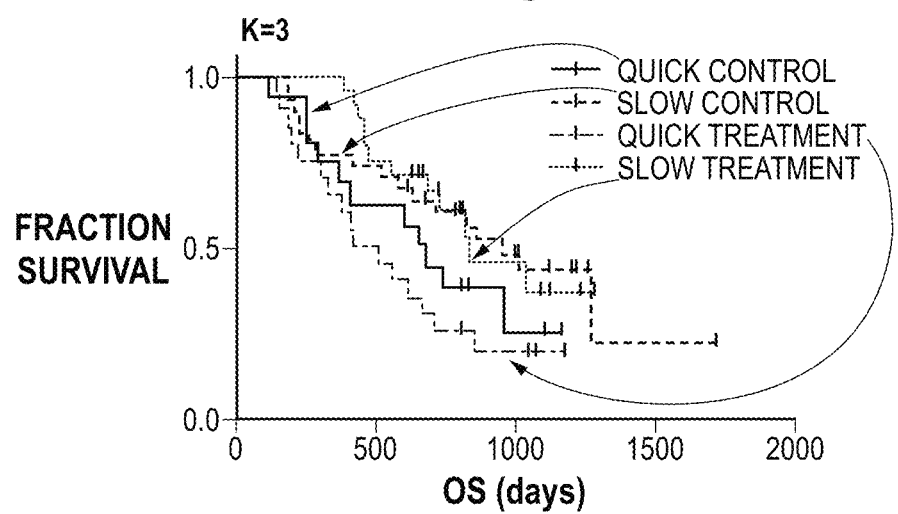
Figure 3E:
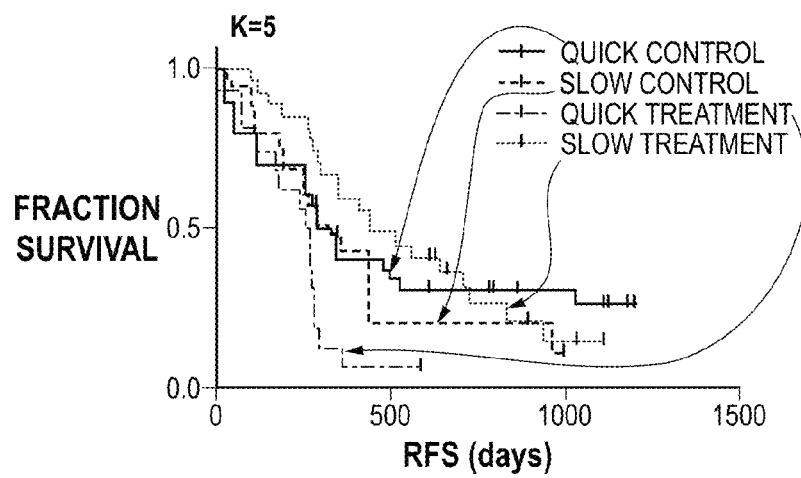
Figure 3F:
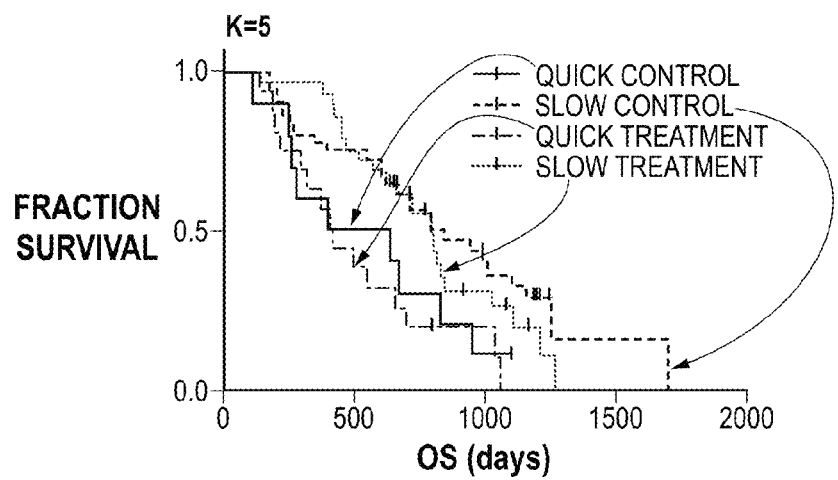

The plots of FIGS. 3A-3F show the performance of classifiers built using the "Slow" and "Quick" definitions for the reference set ("Slow"=no recurrence event before 500 days, "Quick"=recurrence before 276 days), the VeriStrat feature definitions (Tables 3 and 4), and dilute-and-shoot pre-processed spectra. The classifier was applied both to the spectra of the GI-4000 (treatment) arm and to the 46 spectra from the placebo (control) arm. The classifier generated class labels of Quick or Slow for the spectra based on a K-nearest neighbor classification algorithm (see U.S. Pat. No. 7,736,905), with FIGS. 3A-3B showing the classification with K=1, FIGS. 3C-3D showing the classification with K=3 and FIGS. 3E and 3F showing the classification with K=5.

From these results shown in FIGS. 3A-3F, we see that it is possible to separate the treatment arm (GI-4000+gemcitabine) into two groups, "Quick" and "Slow", where the "Quick" group has significantly worse outcomes, in terms of both RFS and OS, than the "Slow" group. In contrast, the control arm (gemcitabine+placebo) has similar RFS in both "Quick" and "Slow" groups. There is a treatment benefit in RFS in favor of GI-4000 in the "Slow" group. The case of treatment effect in OS is difficult to decipher and it may be that the treatment benefit from the addition of GI-4000 in the "Slow" group is diluted by treatments received after recurrence. Analysis of OS is also complicated by censoring of events in 38% of the cohort.

Note that the 'Quick' treatment arm is lower than the control arms indicating that the 'Quick' patients, did not benefit from treatment with GI-4000 and gemcitabine. Therefore, the classifier provides the ability to predict those patients that are not likely to benefit from treatments stimulating an immune response.

B. 150,000 Shot DeepMALDI Based Classifiers

Figure 4A:
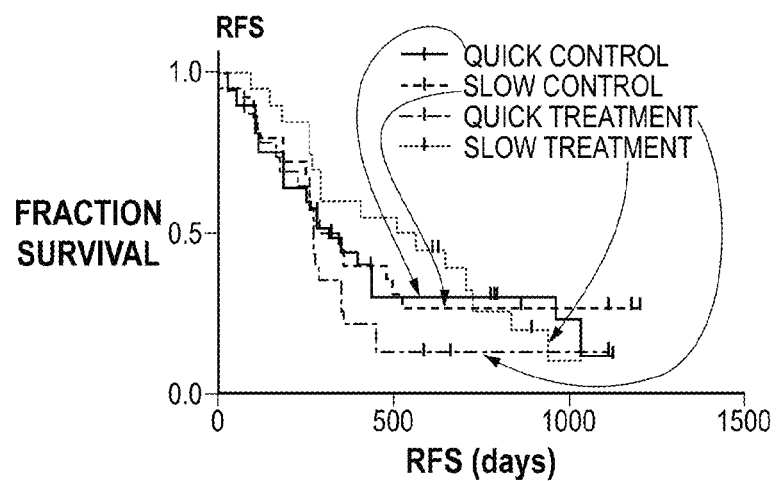
FIGS. 4A-4H are sets of Kaplan-Meier plots of RFS and OS in the GI-4000 and gemcitabine study as defined by a classifier based on spectra obtained using 150,000 shots with the "DeepMALDI" method of mass spectrometry of blood-derived samples, using the techniques described herein and in U.S. provisional patent application 61/652,394 filed May 29, 2012, the content of which is incorporated by reference herein.
Figure 4B:
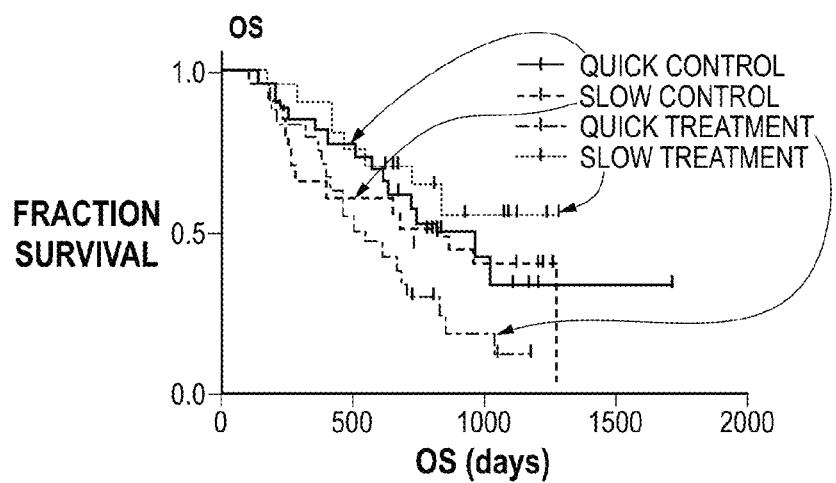

The performance of a classifier based on pre-processed DeepMALDI spectra (see description below) and features selected from a comparison of the training set groups "Quick" and "Slow" as defined above, is shown in FIGS. 4A and 4B, with FIG. 4A showing the ability of the classifier to separate Quick and Slow patients in RFS in the treatment arm but not in the control arm, and FIG. 4B showing the ability of the classifier to separate Quick and Slow patients in OS in the treatment arms but not in the control arm. The features used in the classifier were chosen to approximate the eight features in Table 4. Significant separation was observed between "Quick" and "Slow" groups in the treatment arm, but not in the control arm for both RFS and OS. Although not significantly different, the "Slow" group shows a trend to better outcome, especially RFS, on GI-4000 treatment compared with the control arm of placebo.

FIGS. 4C-4D, 4E-4F, and 4G-4H, are Kaplan-Meier plots of RFS and OS for three additional classifiers using Deep-MALDI mass spectrometry of the samples and subsets of the 77 features for DeepMALDI that are listed in Table 2 above. All three classifiers used the reference set of 20 spectra from patients with recurrence times before 276 days ("Quick") and 14 spectra from patients with no recurrence event or censoring before 500 days ("Slow"), the same pre-processing, optimized for DeepMALDI spectra, and K=5 in the K-nearest neighbor classification algorithm.

Figure 4C:
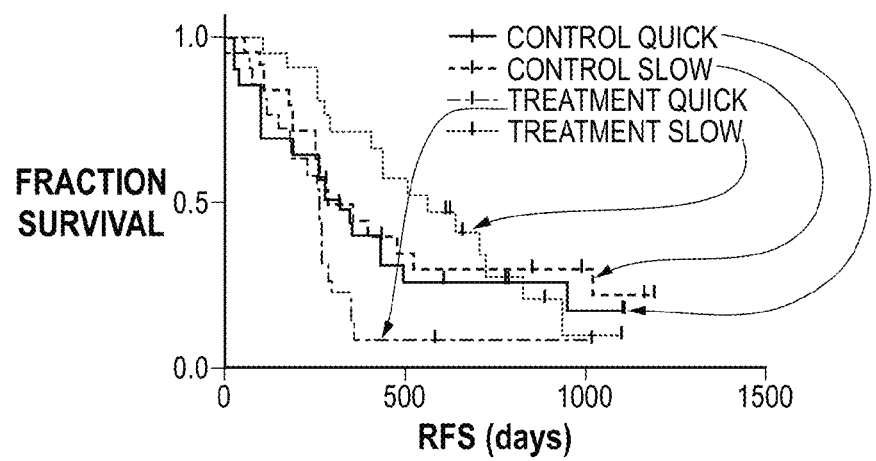
Figure 4D:
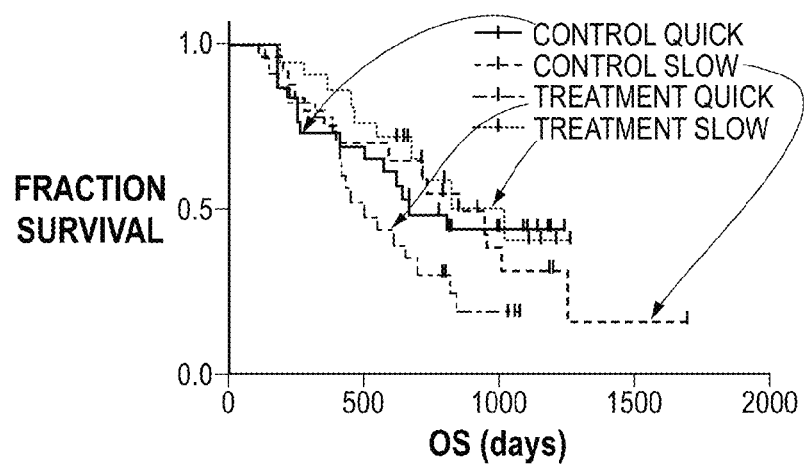

The classifier of FIGS. 4C and 4D used a subset of features from the list of 77 candidate features of Table 2 above. We sorted the 77 features by p value and used the 20 features with the lowest p values describing their relative expression difference:

| m/Z center of feature | m/Z left edge of feature | m/Z right edge of feature |
|---|---|---|
| 3842.836 | 3836.5801 | 3849.0918 |
| 5860.7288 | 5851.1136 | 5870.3441 |
| 6903.7895 | 6894.5605 | 6913.0184 |
| 7023.4264 | 7019.4307 | 7027.422 |
| 7074.7189 | 7070.3989 | 7079.0389 |
| 7301.1449 | 7297.0108 | 7305.279 |
| 9362.5245 | 9353.9508 | 9371.0983 |
| 9671.9403 | 9664.1994 | 9679.6812 |
| 9759.0315 | 9751.0808 | 9766.9822 |
| 10776.7214 | 10762.229 | 10791.2138 |
| 11709.9483 | 11701.4091 | 11718.4875 |
| 11761.9383 | 11724.7165 | 11799.1602 |
| 11858.0166 | 11814.2429 | 11901.7903 |
| 13090.909 | 13082.1414 | 13099.6766 |
| 14043.9806 | 14035.8701 | 14052.091 |
| 14125.2798 | 14117.1271 | 14133.4325 |
| 14148.1548 | 14139.9896 | 14156.3199 |
| 14197.8412 | 14181.9925 | 14213.6898 |
| 14258.2834 | 14249.8779 | 14266.689 |
| 18801.9437 | 18784.7057 | 18819.1817 |

Figure 4E:
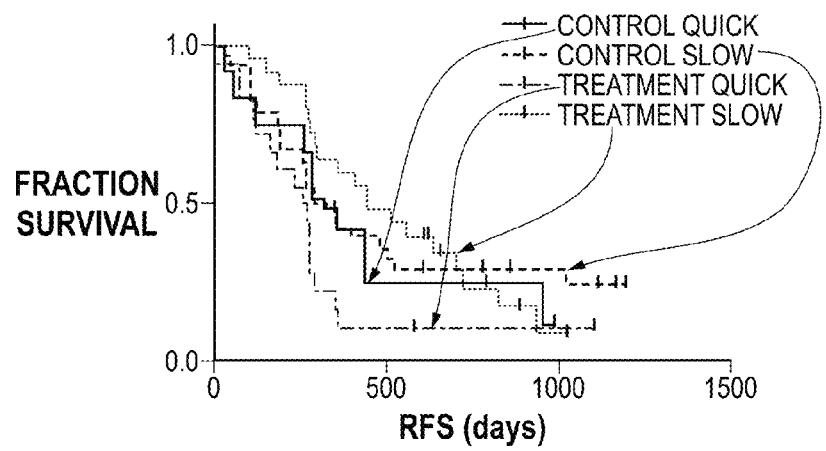
Figure 4F:
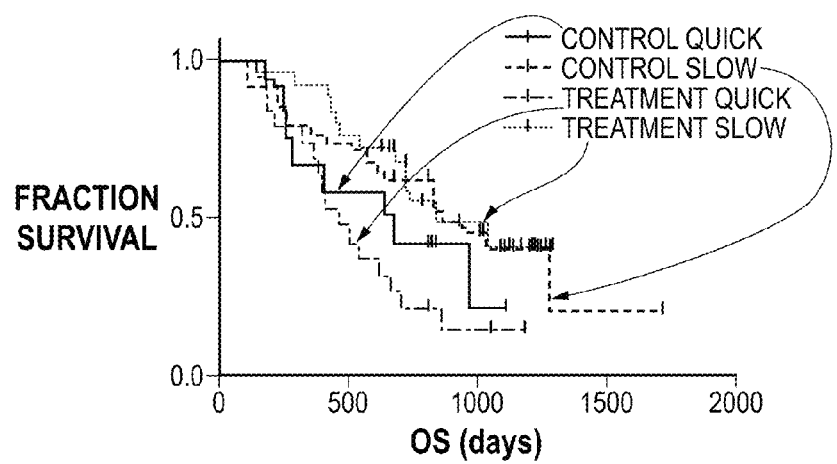

FIGS. 4E and 4F show Kaplan-Meier plots of RFS and OS for a third DeepMALDI classifier. In this example, we used features from the list of spectra (Table 2) that were in the regions of VeriStrat features (Tables 3 and 4) or strongly correlated with them.

| m/Z center of feature | m/Z left edge of feature | m/Z right edge of feature |
|---|---|---|
| 5843.1286 | 5839.9995 | 5846.2576 |
| 5860.7288 | 5851.1136 | 5870.3441 |
| 11475.8583 | 11468.2665 | 11483.4501 |
| 11494.7897 | 11487.3141 | 11502.2653 |
| 11529.8615 | 11522.6267 | 11537.0962 |
| 11555.3129 | 11541.0141 | 11569.6118 |
| 11655.1818 | 11616.9251 | 11693.4385 |
| 11709.9483 | 11701.4091 | 11718.4875 |
| 11761.9383 | 11724.7165 | 11799.1602 |
| 11858.0166 | 11814.2429 | 11901.7903 |
| 11909.7985 | 11902.0132 | 11917.5837 |
| 11939.0138 | 11929.8302 | 11948.1974 |
| 22998.948 | 22839.6075 | 23158.2885 |

Figure 4G:
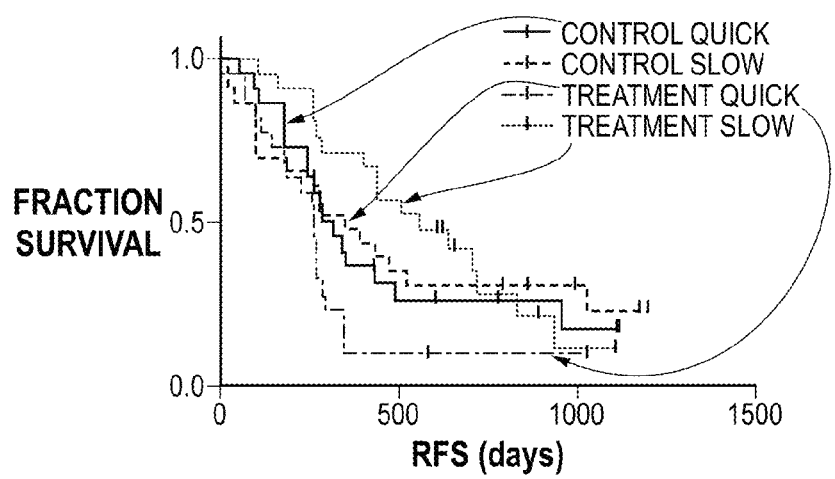
Figure 4H:
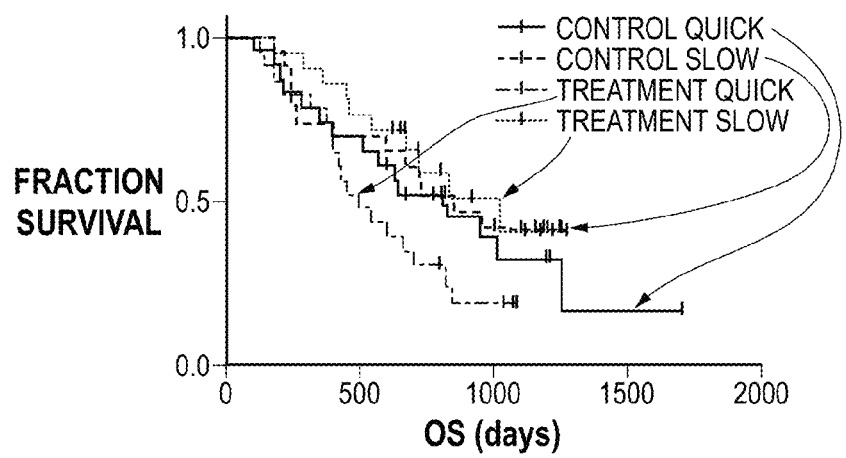

The results for the fourth DeepMALDI classifier are shown in FIGS. 4G-4H. For this classifier, we used a subset of the features (Table 2) whose expression levels between groups were correlated in the opposite way to those in the classifier of FIGS. 4E-4F, and which are not related to VeriStrat features.

| m/Z center of feature | m/Z left edge of feature | m/Z right edge of feature |
|---|---|---|
| 7009.0908 | 7002.2674 | 7015.9142 |
| 7023.4264 | 7019.4307 | 7027.422 |
| 7035.244 | 7031.6636 | 7038.8245 |
| 7074.7189 | 7070.3989 | 7079.0389 |
| 14043.9806 | 14035.8701 | 14052.091 |
| 14092.2825 | 14084.1062 | 14100.4588 |
| 14125.2798 | 14117.1271 | 14133.4325 |
| 14148.1548 | 14139.9896 | 14156.3199 |
| 14197.8412 | 14181.9925 | 14213.6898 |

Note that the DeepMALDI classifiers of FIGS. 4A-4H clearly separate the Quick and Slow patients in the treatment arm while showing little or no separation in the control arm, and thus perform similarly to the "dilute and shoot" classifiers of FIG. 3A-3F.

In interpreting the results of FIGS. 3A-3F and 4A-4H, it should be noted that the results above will tend to be over-estimates of separation between "Quick" and "Slow" groups because the reference set of the classifier is used in the analysis. Unfortunately, a validation set was not yet available with which to test the classifier performance in an independent way. Hence, to provide an alternative assessment of classifier performance, a cross-validation analysis was carried out, as described in the "cross-validation of classifier" section below.

C. 500,000 Shot DeepMALDI Spectra-Based Classifiers

Classifiers able to separate "Quick" and "Slow" patients in RFS well in the treatment arm, but not in the control arm could also be constructed using 500,000 shot DeepMALDI spectra. The DeepMALDI spectra were pre-processed identically for all classifiers presented in this section and the training set for these classifiers was again the "Quick" and "Slow" recurrence groups defined previously. At the time of this DeepMALDI analysis updated survival data were available and so the performance analysis of these classifiers made use of updated data relative to those presented in sections A and B. The sets of differentiating features used in each classifier were subsets of the 97 features in Table 5 above. The K neighbors chosen for the K-nearest neighbor classification algorithm was optimized for each classifier.

FIGS. 13A-13L are Kaplan-Meier plots of RFS and OS showing the performance of 6 classifiers built using 500,000 shot DeepMALDI spectra and subsets of the 97 features listed in Table 5.

Figure 13A:
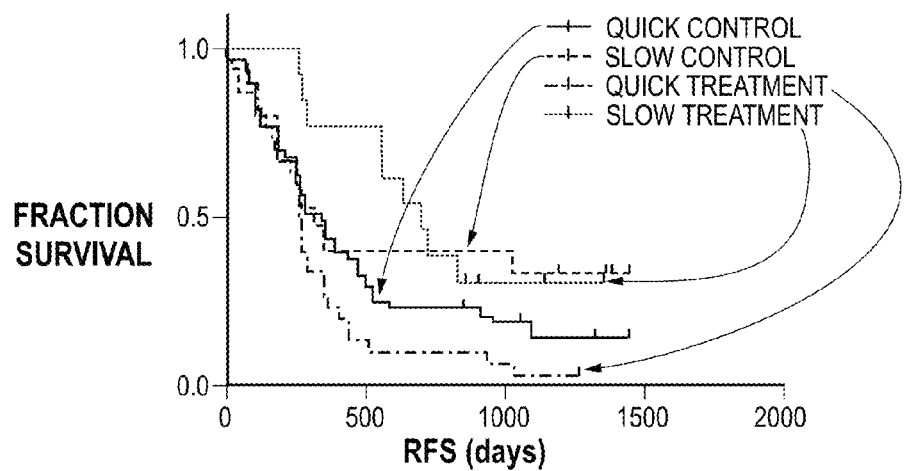
FIGS. 13A-13L are sets of Kaplan-Meier plots of RFS and OS in the GI-4000 and gemcitabine study as defined by classifiers based on spectra obtained from the DeepMALDI method using 500,000 shots, using techniques of pending U.S. provisional patent application 61/652,394 filed May 29, 2012, the content of which is incorporated by reference herein.
Figure 13B:
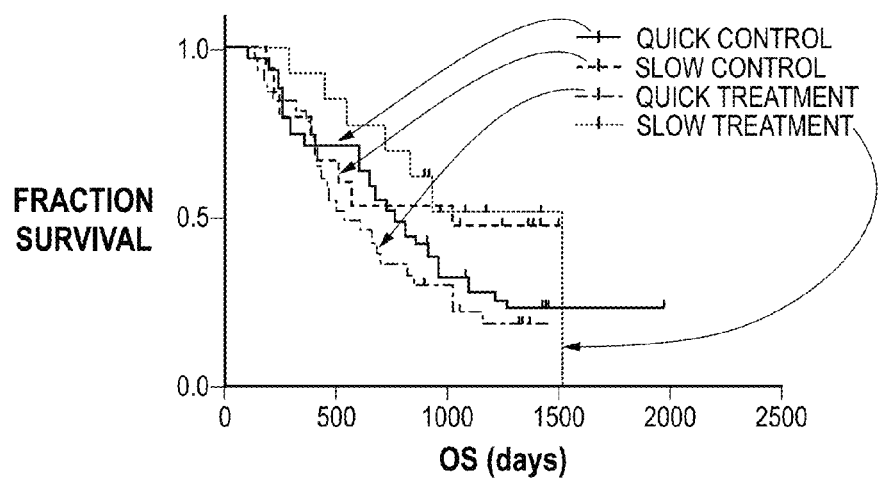

The classifier of FIGS. 13A and 13B used a subset of 42 features from the list in Table 5. They were selected to include both features contained in the m/z regions of the VeriStrat features (Tables 3 and 4) and also additional features selected based on low univariate p values for differentiating between 'Slow' and 'Quick' groups in the training set. For this classifier, K=3 was found to be optimal and the center (m/z) of the features used are listed in the first column of Table 6.

TABLE 6

Figure 13C:
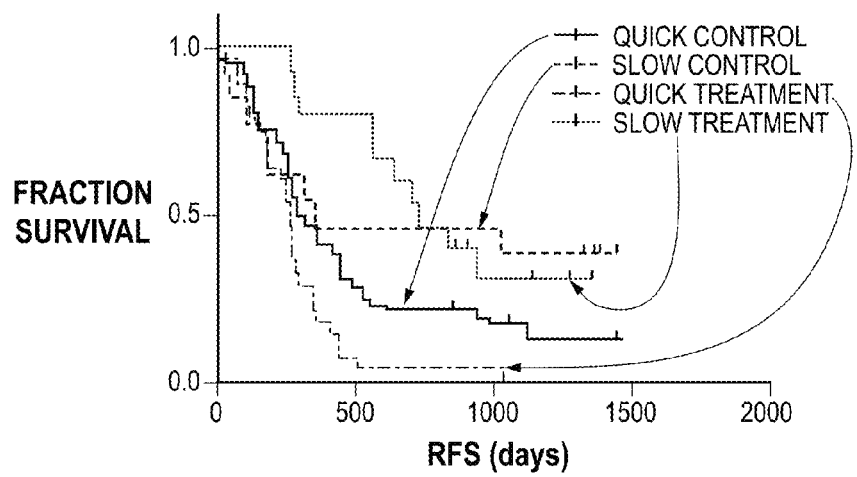
Figure 13D:
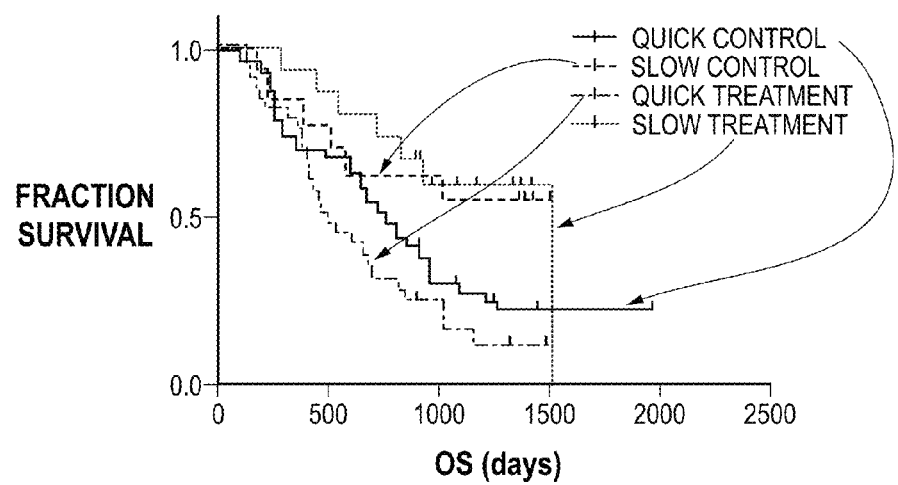
Figure 13E:
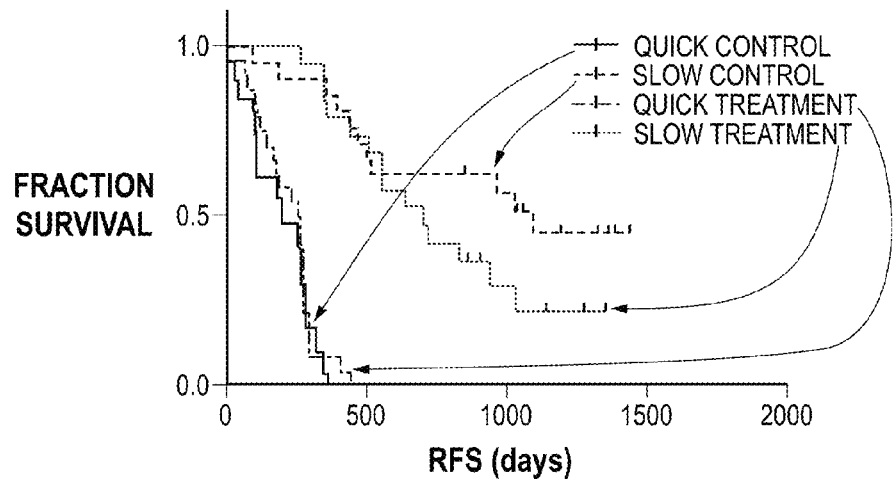
Figure 13F:
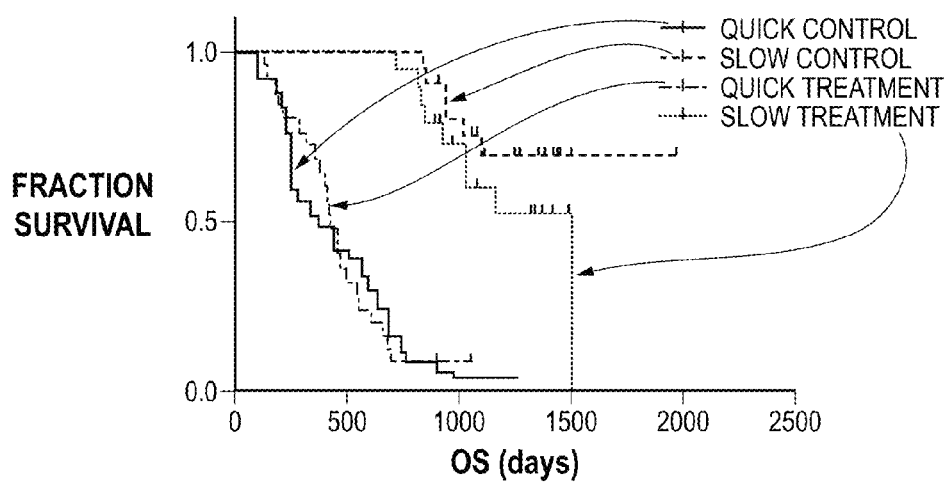
Figure 13G:
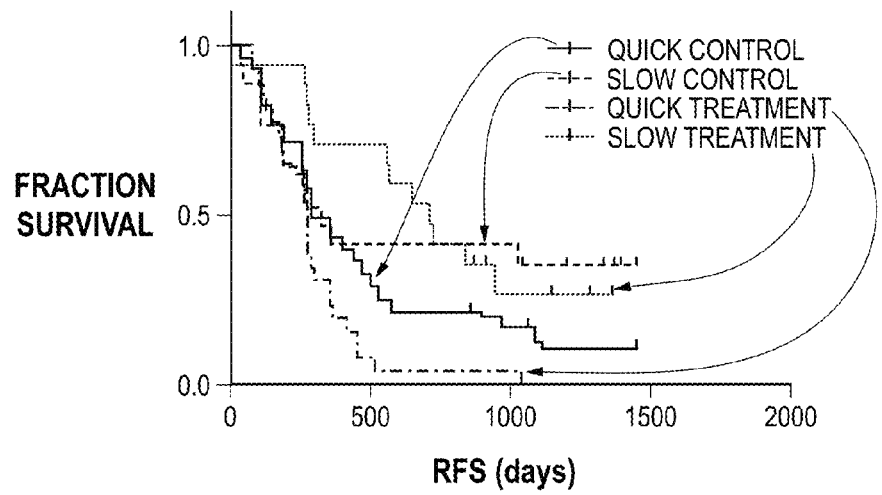
Figure 13H:
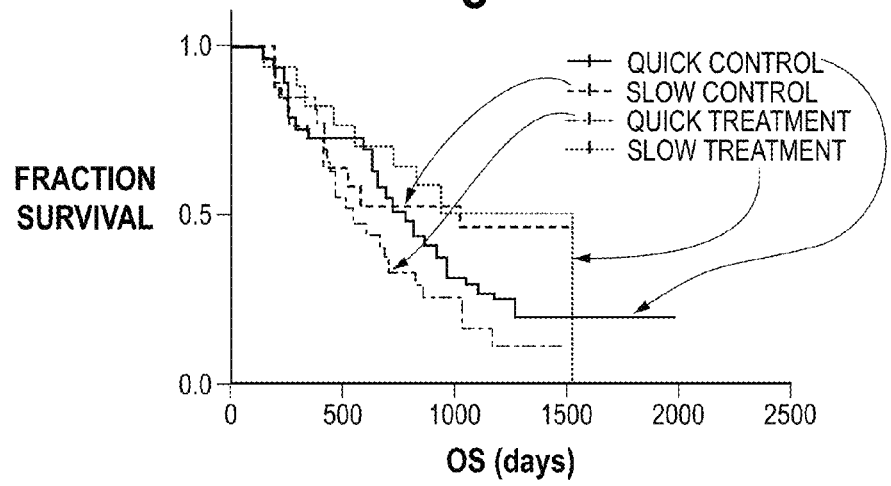
Figure 13I:
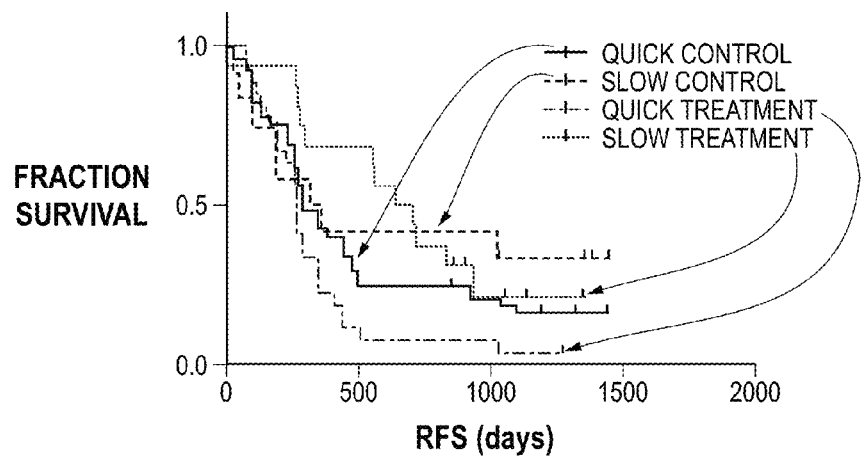
Figure 13J:
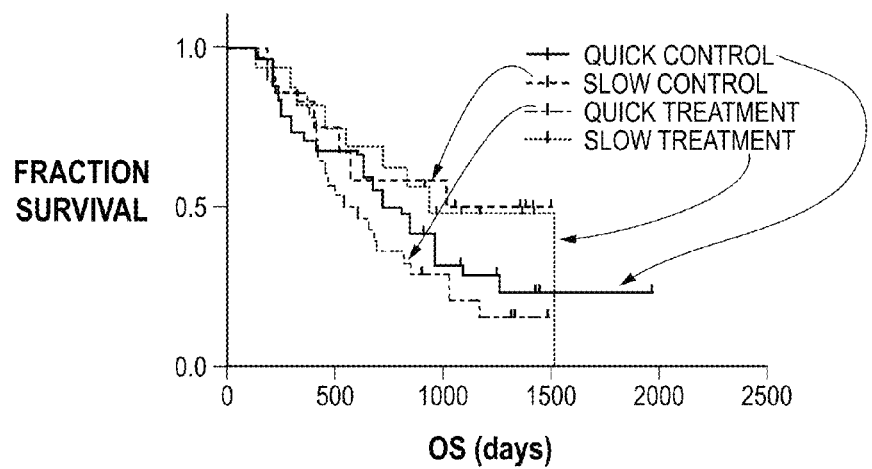
Figure 13K:
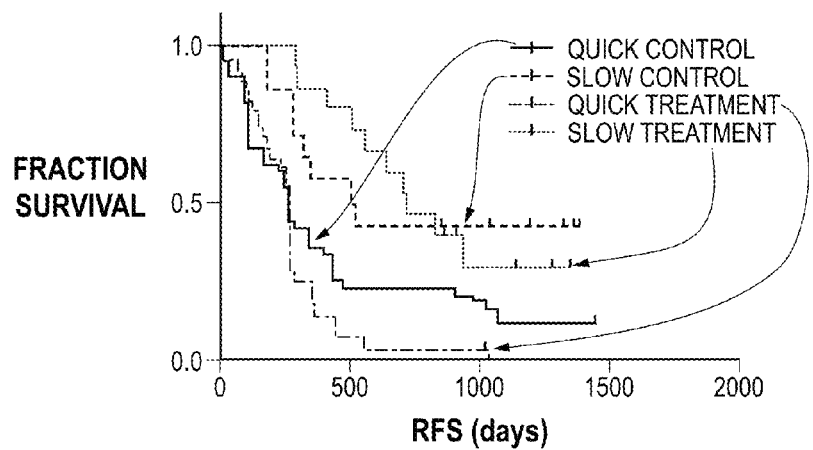
Figure 13L:
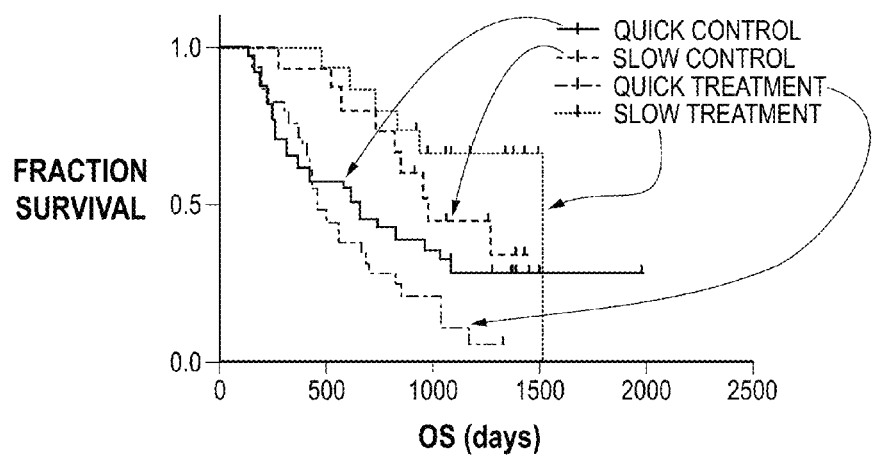

| FIG. 13A-13B | FIG. 13C-13D | FIG. 13E-13F | FIG. 13G-13H | FIG. 13I-13J | FIG. 13K-13L |
|---|---|---|---|---|---|
|  | 4492 |  |  | 4492 |  |
|  |  |  |  |  | 5636 |
|  | 5762 |  |  |  |  |
| 5841 | 5841 |  |  |  |  |
|  |  |  |  |  | 5891 |
|  | 6893 | 6893 |  | 6893 |  |
|  | 7004 |  |  | 7004 |  |
| 7295 |  | 7295 |  |  |  |
| 7422 | 7422 |  |  | 7422 |  |
| 8357 |  | 8357 |  |  | 8357 |
|  | 8762 | 8762 | 8762 | 8762 |  |
|  | 8992 |  |  | 8992 |  |
| 9795 |  |  |  | 9795 |  |
| 10000 |  | 10000 |  |  |  |
|  | 10175 |  |  | 10175 |  |
| 11402 |  |  |  |  |  |
| 11432 |  |  |  |  |  |
| 11466 | 11466 | 11466 | 11466 |  | 11466 |
| 11488 |  |  |  |  |  |
| 11521 | 11521 | 11521 | 11521 |  |  |
| 11544 |  |  |  |  |  |
| 11563 |  |  |  |  |  |
| 11620 | 11620 | 11620 | 11620 |  |  |
| 11676 | 11676 |  |  |  |  |
| 11699 | 11699 |  |  |  |  |
| 11723 | 11723 | 11723 |  |  |  |
| 11744 |  |  |  |  |  |
| 11776 |  |  |  |  |  |
|  |  |  |  | 11822 |  |
| 11883 | 11883 |  |  |  |  |
| 11901 |  |  |  |  |  |
|  | 12976 |  |  |  |  |
|  |  |  |  | 13104 |  |
| 13145 |  | 13145 |  |  |  |
| 13623 |  | 13623 |  |  |  |
| 13648 | 13648 | 13648 | 13648 | 13648 | 13648 |
|  | 13677 |  |  | 13677 |  |
| 13735 | 13735 | 13735 | 13735 | 13735 |  |
| 13782 | 13782 | 13782 | 13782 | 13782 |  |
|  | 14007 |  |  | 14007 |  |
| 14057 | 14057 | 14057 | 14057 | 14057 |  |
| 14096 |  | 14096 |  |  |  |
| 14112 |  | 14112 |  |  |  |
| 14138 |  | 14138 |  |  |  |
| 14244 |  | 14244 |  |  |  |
| 14281 |  | 14281 |  |  |  |
| 14423 | 14423 | 14423 | 14423 | 14423 |  |
| 14436 | 14436 |  |  | 14436 |  |
| 14538 | 14538 | 14538 | 14538 | 14538 |  |
|  | 14716 |  |  | 14716 |  |
| 17444 |  |  |  |  |  |
| 18735 |  |  |  |  |  |
| 22988 | 22988 | 22988 | 22988 | 22988 |  |
| 23021 |  |  |  |  |  |
| 28038 | 28038 | 28038 | 28038 | 28038 |  |
| 28232 | 28232 | 28232 | 28232 | 28232 |  |
|  | 28439 |  |  | 28439 |  |
| 28805 | 28805 |  |  | 28805 |  |

The classifier of FIGS. 13C and 13D used a subset of 32 features from the list in Table 5 (center of feature m/z given), selected on the basis of univariate p values for differentiating between 'Slow' and 'Quick' groups in the training set and on the ratio of amplitudes of feature values between 'Slow' and 'Quick' groups. This classifier used K=3 and the features listed in the second column of Table 6. Although 19 features are common to this classifier and the previous one, this classifier also contains 13 features not used in the previous classifier and yet gives similar performance in terms of the Kaplan-Meier plots.

The classifier of FIGS. 13E and 13F was developed using similar criteria to that of the previous classifier and used K=5. The features used are listed in the third column of Table 6. The classifier has 23 of its 25 features in common with the classifier of FIGS. 13A and 13B and more than half in common with the classifier of FIGS. 13C and 13D. Despite the similarity in the features chosen for the classifier, the performance in the Kaplan-Meier plots would indicate that this classifier is more prognostic of outcome, rather than predictive of treatment effect from GI-4000.

The classifier of FIGS. 13G and 13H used a subset of 13 of the features of the classifier of FIGS. 13E and 13F, listed in the fourth column of Table 6, and K=5; the Kaplan-Meier plots indicate a performance more similar to the first two DeepMALDI classifiers (FIGS. 13A-D).

The classifier of FIGS. 13I and 13J was constructed using no features in the m/z regions of the VeriStrat features of Table 3. However, it can be seen that it has similar performance in terms of Kaplan-Meier plots as the classifiers which do include features from the m/z regions of VeriStrat features. The features used are listed in the fifth column of Table 6 and for this classifier K=7.

The classifier of FIGS. 13K and 13L uses only eight features, listed in the last column of Table 6, and K=3. Four of the eight features were not used in any of the other classifiers. Still, the performance as assessed by the Kaplan-Meier plots is not markedly different from the other classifiers tested.

Note that most of these DeepMALDI classifiers also clearly separate the 'Quick' and 'Slow' classified patients in the treatment arm, while showing little separation in the control arm, and thus perform similarly to the "dilute-and-shoot" classifiers and those based on DeepMALDI with fewer shots.

Cross-Validation of Classifier

A. General Formulation and its Application to the "Dilute-and-Shoot" Classifier

Figure 5:
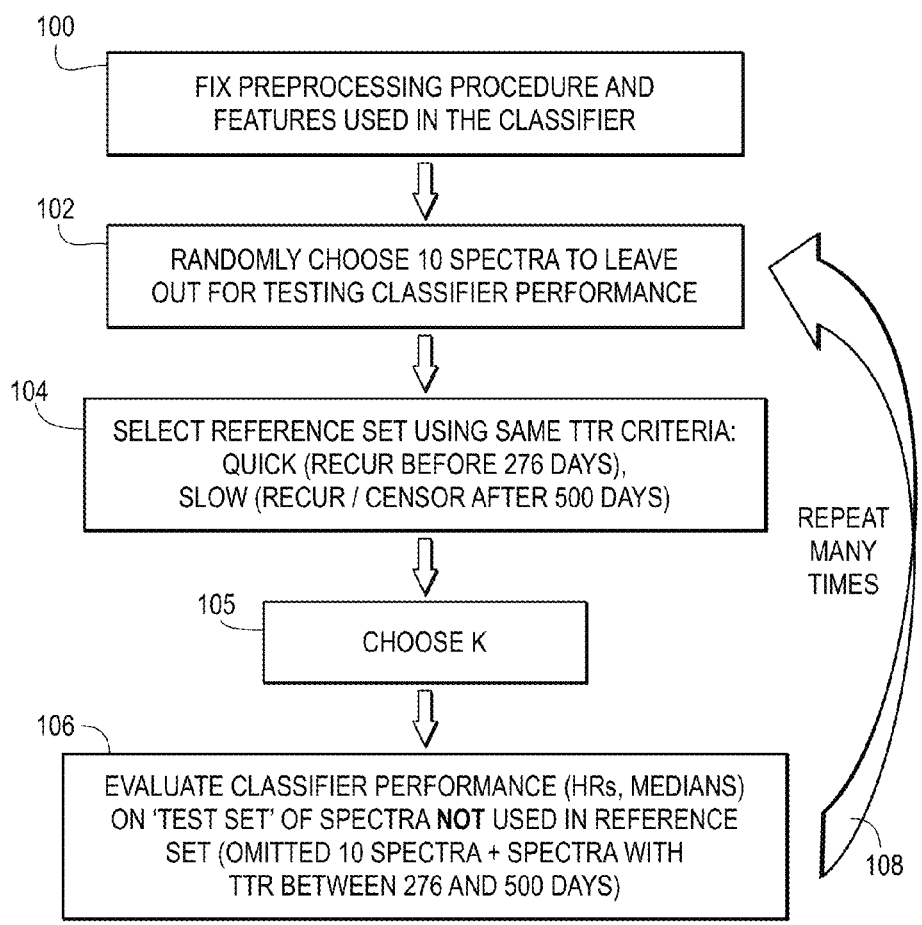
FIG. 5 is a flow chart of a cross-validation process for classifier validation used in the pancreatic cancer/GI-4000 and gemcitabine study.

A cross-validation of the "dilute and shoot" classifier shown in FIGS. 3A-3F and described above was done by following the procedure outlined in FIG. 5.

In the procedure of FIG. 5, at step 100 the features (peaks or m/z ranges) used for classification and the pre-processing steps (background subtraction, normalization and alignment) were fixed. Then, steps 102, 104, 105 and 106 were performed in an iterative fashion indicated by the loop 108. In step 102, 10 spectra were randomly chosen to leave out for testing classifier performance. In step 104, a reference set of spectra were selected from the remaining 34 spectra using the same time to recurrence (TTR) criteria, namely "Quick" defined as recurrence before 276 days and "Slow" defined as above (no recurrence before 500 days). At step 105, a value of K in a K nearest neighbor classification algorithm was chosen. At step 106, the classifier performance was evaluated, in terms of Hazard ratios (HR) and medians on a "test set" of spectra. The test set of spectra are spectra in the treatment arm not included in the reference set (step 104), i.e. the 10 spectra omitted at step 102 plus any other spectra from patients with a TTR between 276 and 500 days. The process was repeated (108) many times (70 in this example).

It will be appreciated that the procedure of FIG. 5 is of general applicability, with appropriate selection of the reference and test sets given the particular study under consideration.

This cross-validation of FIG. 5 will tend to provide a lower bound to the performance of the classifier as it under-estimates performance in the following ways:
1. The reference sets of the cross-validation classifiers are smaller than those of the original classifier, which can impact performance.
2. The test set of samples not included in the reference set, while larger than the 10 intermediate recurrence spectra before, is still small. This can lead to large variability in calculated statistics and in some cases, when group sizes are very small, these statistics can be meaningless.
3. The test set is not representative of the treatment arm cohort as a whole. It contains a higher proportion of patients with intermediate recurrence times. This imbalance makes comparison of the test set results with other groups outside the test set (e.g. control arm) difficult.

Despite these limitations, the cross-validation analysis of classifiers built using the definitions of "Quick" and "Slow" groups and VeriStrat features yielded some useful insights.

Figure 6:
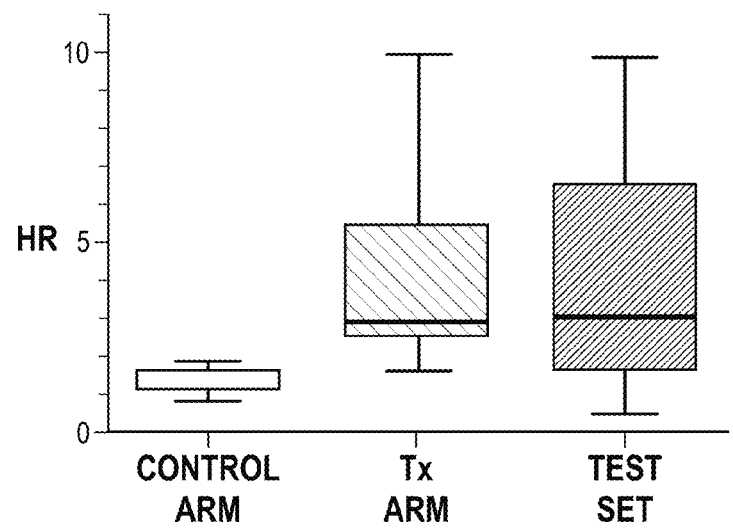
FIG. 6 is a plot of the distributions of hazard ratios between "Quick" and "Slow" groups for RFS from cross-validation analysis of the "dilute-and-shoot" classifier of FIGS. 3E-3F.

FIG. 6 shows the distribution of hazard ratios between "Quick" and "Slow" groups calculated for the 70 realizations in the cross-validation analysis for the control arm, the whole treatment arm, and the test set (treatment arm excluding the classifier reference set). While all classifiers produced a HR close to 1 for the control arm, the median HR for the test set was 3.1, close to that for the whole treatment arm.

Figure 7A:
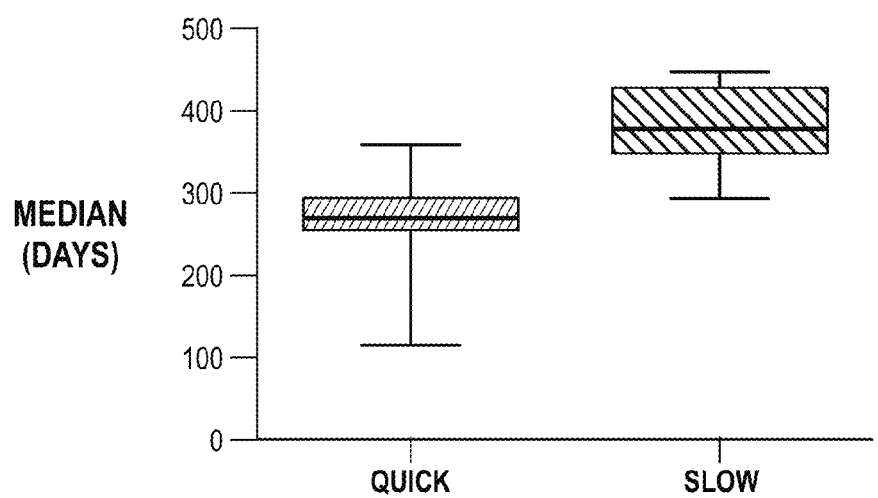
FIG. 7A is a plot of the distributions of median RFS in "Quick" and "Slow" groups in the Test Set of the cross-validation analysis in the GI-4000 and gemcitabine study.
Figure 7B:
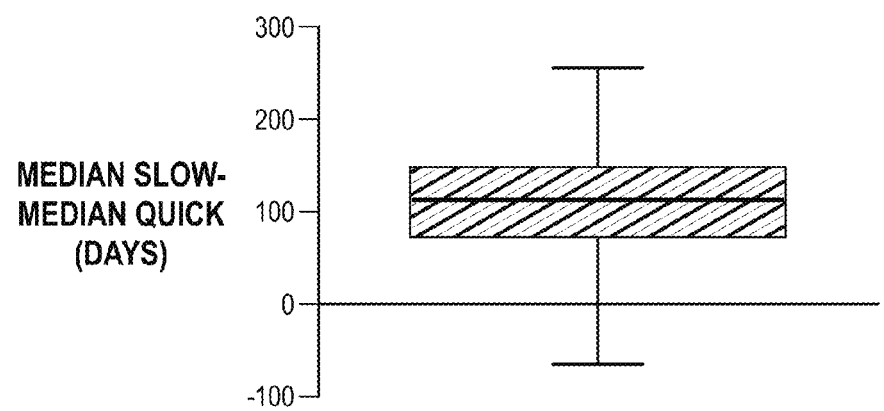
FIG. 7B is a plot of the distribution of difference in medians between "Quick" and "Slow" groups in the Test Set of the cross-validation analysis of the GI-4000 and gemcitabine study. Both plots use the "dilute-and-shoot" classifier of FIGS. 3E-3F.
Figure 8:
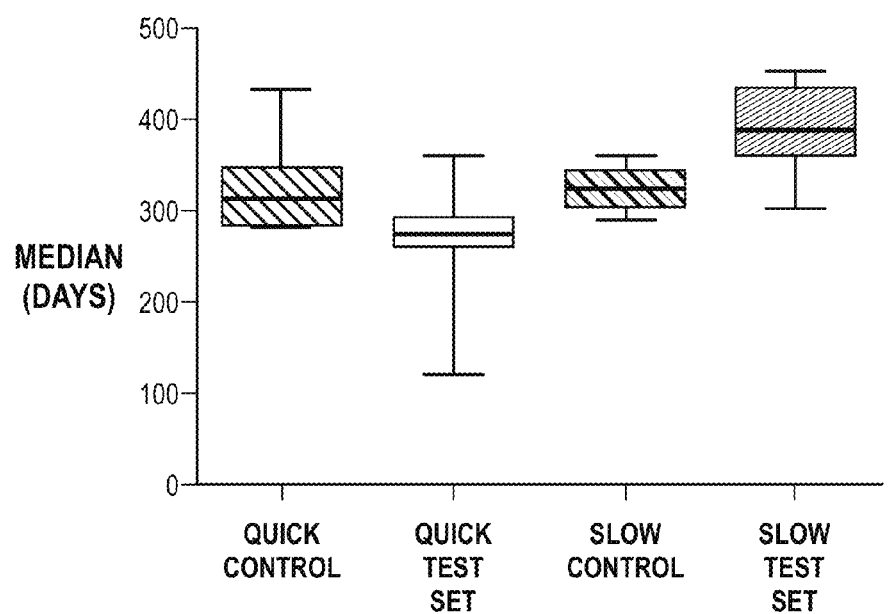
FIG. 8 is a plot of the distribution of medians of "Quick" and "Slow" groups in the Control Arm and the Test Set in the cross-validation analysis of the "dilute-and-shoot" classifier of FIGS. 3E-3F.

FIGS. 7A and 7B show the distributions of median RFS in "Quick" and "Slow" groups in the test set in the cross-validation analysis. In FIG. 7A, the median for the "Slow" group is centered around 382 days, while the median for the "Quick" group is centered around 274 days. FIG. 7B shows the distribution of the difference in medians between "Quick" and "Slow" groups in the test set. The difference between medians is centered around 111 days, a clinically meaningful difference, with very few realizations showing a smaller median for the "Slow" group than the "Quick" group. Although comparison of test set and control arm is complicated by the imbalance in distribution of recurrence times between the two groups, observation of the medians in the "Quick" and "Slow" groups within the control group and the test set show that that of the "Slow" Test Set lies predominantly above those of the "Quick" and "Slow" control groups, which in turn lie above that of the "Quick" Test Set. See FIG. 8, which is a plot of the distribution of medians of "Quick" and "Slow" groups in the Control Arm and the Test Set in the cross-validation analysis.

Figure 9:
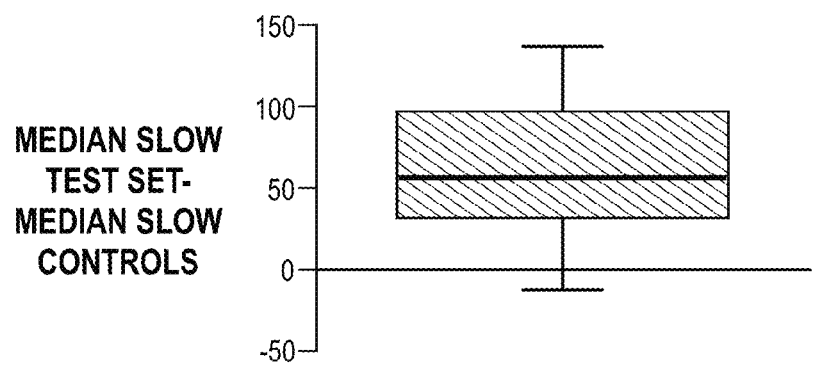
FIG. 9 is a plot of the distribution of difference in medians between the Test Set and Control Arm for the "Slow" group in the cross-validation analysis of the "dilute-and-shoot" classifier of FIGS. 3E-3F.

In addition, the distribution of difference in medians between the test set and control arm for the "Slow" group, indicates that in nearly all realizations, the median RFS for the test set was greater than that of the control arm, despite the imbalance in the populations, see FIG. 9, which is a plot of the distribution of difference in medians between test set and control arm for the "Slow" group. The median difference in median RFS was around 60 days, again a meaningful clinical difference.

Cross-validation analysis for OS was hampered by having data censored in over a third of the total cohort in the clinical data initially available.

Figure 10A:
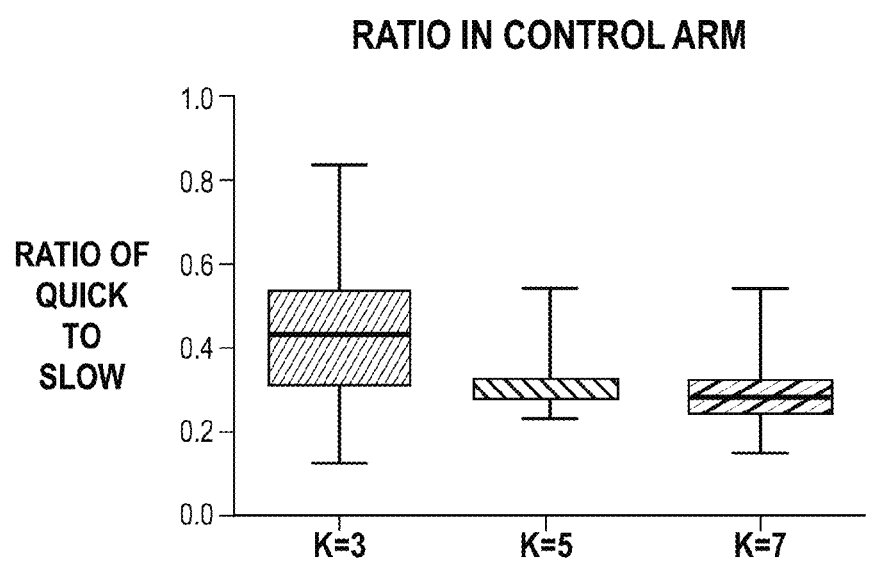
FIG. 10A is a plot of the distribution of the ratio of Slow to Quick classifications in the control arm for different values of K used in the classifier in the cross-validation analysis of the "dilute-and-shoot" classifier of FIGS. 3E-3F.

Another result of cross-validation analysis was the determination of the dependence of the ratio of Slow to Quick classifications on the choice of K used in the K-nearest neighbor classifier. See FIG. 10A, which is a plot of the distribution of the ratio of Slow to Quick classifications in the control arm for different values of K used in classifier. FIG. 10B is a plot of the distributions of hazard ratios calculated for the test set of the cross-validation analyses for various values of K. When we did the cross-validation, we chose a K of 3, 5, or 7 in each of the 70 iterations (FIG. 5, step 105). We had roughly ⅓ of each, so there at least 20 values in each of the distributions K=3, 5, and 7. To see what happened for K=1, we also re-ran 19 iterations of the cross-validation using K=1. The hazard ratio of Slow to Quick was found to be largest in the test set for K=5. FIG. 10B also plots the distribution of hazard ratios obtained for the control arm for all 70 iterations of the cross-validation analysis. FIG. 10B demonstrates that it does not make much difference what value of K is used within the control arm, and the distribution is quite narrow. FIG. 10B, when considered together with FIG. 10A, demonstrates that multiple choices of K are possible in a K-nearest neighbor classification algorithm, but that K=5 is a probably a preferred choice.

B. Cross-Validation of 150,000 Shot DeepMALDI Spectra-Based Classifiers

Figure 14:
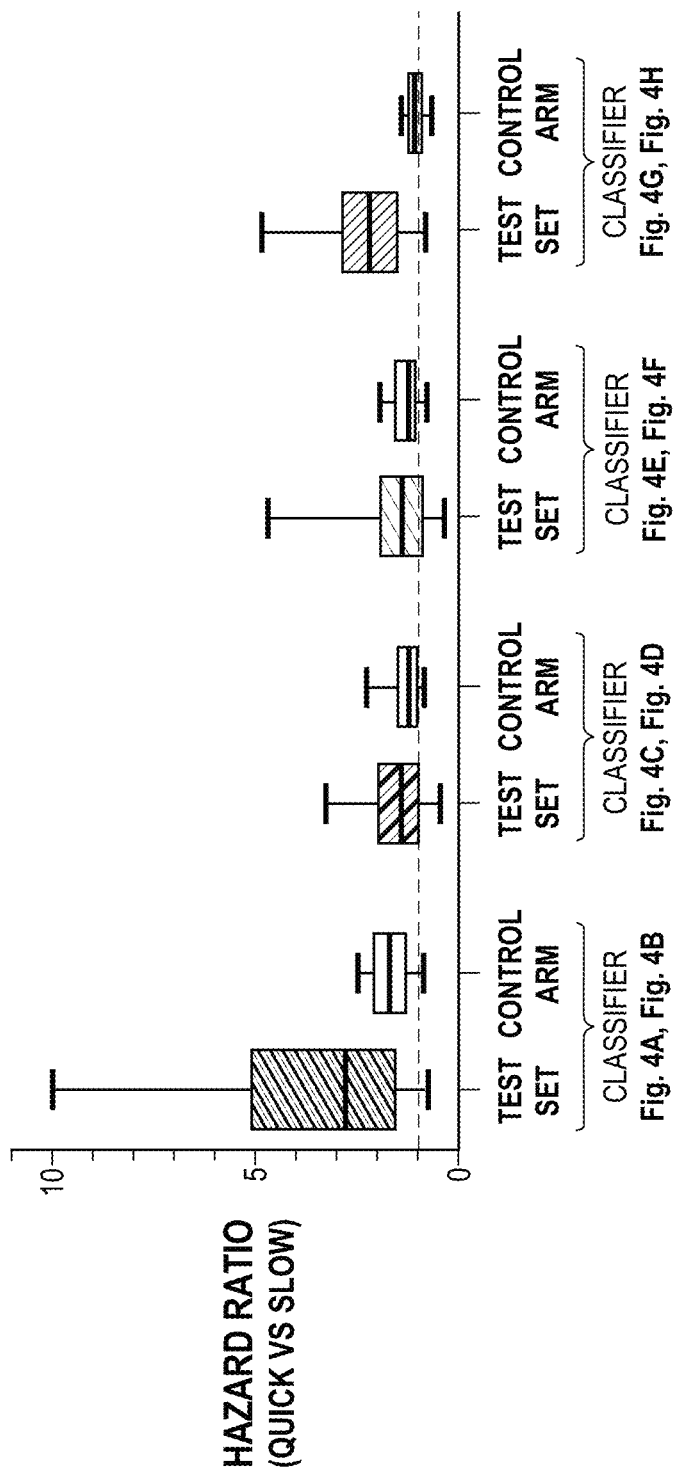
FIG. 14 is a plot of the distribution of hazard ratios between "Quick" and "Slow" groups for RFS from cross-validation analysis on the classifiers of FIGS. 4A-4H developed using spectra obtained from the DeepMALDI method using 150,000 shots.

Application of the same cross-validation methods to the four 150,000 shot DeepMALDI spectra-based classifiers presented earlier show that two of them had superior performance, in terms of ability to predict relative treatment benefit from the addition of GI-4000. FIG. 14 shows the distribution of hazard ratios between patients classified as 'Quick' and 'Slow' for RFS for the four classifiers from FIGS. 4A-4H in both the control arm and the test set of the cross-validation. While the median hazard ratios observed for the classifiers from FIGS. 4C-4F are similar in test set and control arms, those observed for the other 2 classifiers are greater in the test set than in the control arm, supporting the performance evaluation from the Kaplan-Meier plots showing greater separation between 'Quick' and 'Slow' groups in RFS within the treatment arm than the control arm, and supporting the predictive power of the classifiers for the addition of GI-4000 to the gemcitabine control regimen.

C. Cross-Validation of 500,000 Shot DeepMALDI Spectra-Based Classifiers

Figure 15:
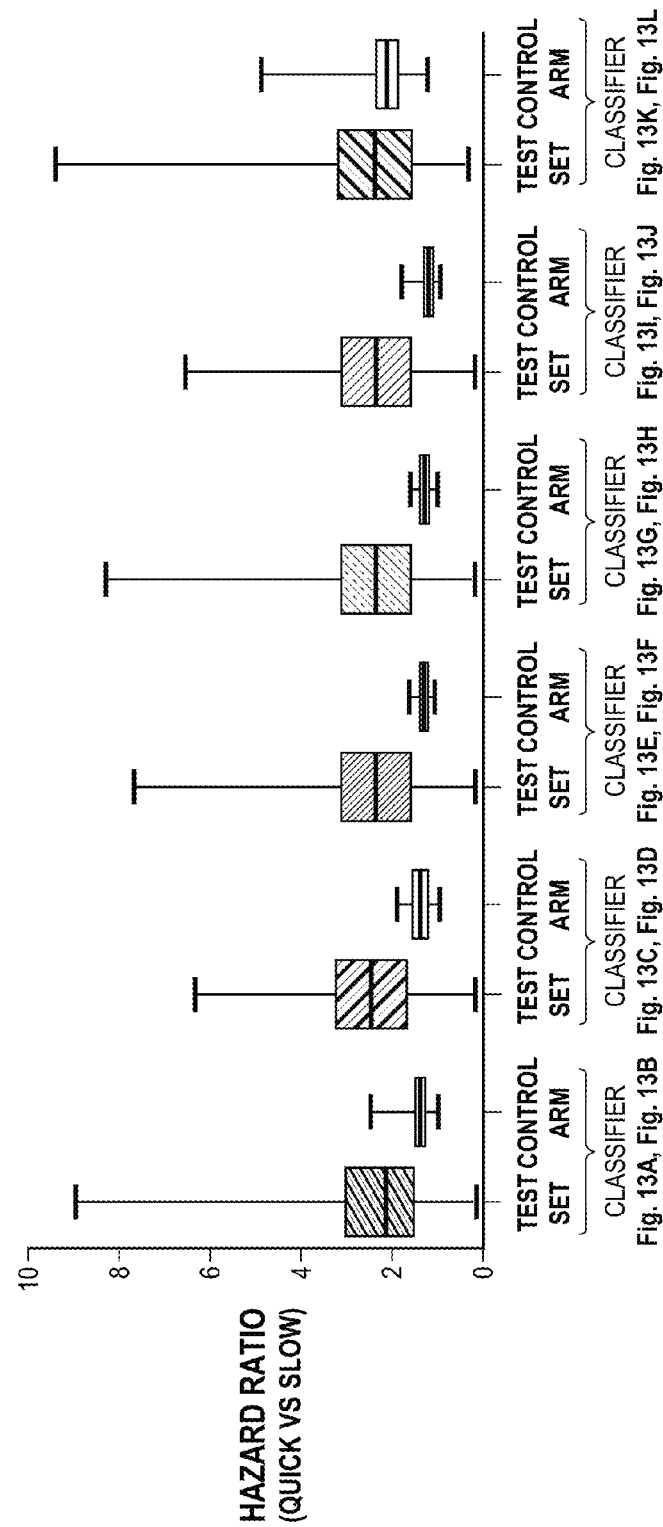
FIG. 15 is a plot of the distribution of hazard ratios between "Quick" and "Slow" groups for RFS from cross-validation analysis on the classifiers of FIGS. 13A-13L developed using spectra obtained from the DeepMALDI method using 500,000 shots.

The identical cross-validation method was also applied to the six 500,000 shot DeepMALDI spectra-based classifiers presented earlier and assessed in FIGS. 13A-M. The distributions of the hazard ratios for each classifier in both the control arm and the test set of the cross-validation are shown in FIG. 15. This shows that apparent differences in performance in Kaplan-Meier plots showing the whole treatment and control arms are not always maintained when performance is assessed by cross-validation methods. In addition, it is further evidence that it is possible to construct many different classifiers, using different sets of features, which have similar performance characteristics, even in cross-validation.

Note that the training set may have unequal numbers of members of the "Quick" and "Slow" classes. To address the question of unequal group sizes, the relative reference group sizes we selected were partially a result of the distribution of recurrence times that we had in the treatment arm. There happened to be many patients with recurrence times between 250 and 275 days, probably because it coincided with a planned MRI/CT assessment. So, there did not seem to be an appropriate place to split the group between those times. However, we decided that it was better take a larger early recurrence group anyway and so we preferred to have more in this group. A K-nearest neighbor classification algorithm can be adjusted to take into account different group sizes in the reference set, so it is not, in principle, a problem to have unequal group sizes in the training set.

Practical, Useful Tests

As noted throughout this disclosure, practical useful tests follow from the discoveries of this disclosure. One aspect is that the testing method of the invention identifies whether a particular cancer patient is a member of a group of cancer patients that are likely, or not likely, to benefit from administration of a yeast-based immune response generating therapy either alone or in addition to other therapies. Yet another aspect is that the testing method of the invention identifies whether a particular cancer patient is a member of a group of cancer patients that are likely, or not likely, to benefit from administration of yeast-based immunotherapy for mutated Ras-positive cancer, such as GI-4000, either alone or in addition to other therapies. This identification can be made in advance of treatment.

In one example the method includes the steps of: a) obtaining a blood-derived sample from the patient; b) obtaining a mass-spectrum of the blood-based sample with the aid of a mass spectrometer; c) in a programmed computer, performing predefined pre-processing steps on the mass spectrum, obtaining integrated intensity values of selected features in the spectrum over predefined m/z ranges after the pre-processing steps are performed, and comparing the integrated intensity values with a training set comprising class-labeled spectra from other cancer patients and classifying the mass spectrum with a class label. The class label assigned to the spectrum is used to predict whether the patient is likely or not likely to benefit from treatment in the form of administration of a yeast-based immune response generating therapy either alone or in addition to other therapies.

In another example the method includes the steps of: a) obtaining a blood-derived sample from the patient; b) obtaining a mass-spectrum of the blood-based sample with the aid of a mass spectrometer; c) in a programmed computer, performing predefined pre-processing steps on the mass spectrum, obtaining integrated intensity values of selected features in the spectrum over predefined m/z ranges after the pre-processing steps are performed, and comparing the integrated intensity values with a training set comprising class-labeled spectra from other cancer patients and classifying the mass spectrum with a class label. The class label assigned to the spectrum is used to predict whether the patient is likely or not likely to benefit from treatment in the form of administration of a yeast-based immunotherapy for mutated Ras-positive cancer, either alone or in addition to other therapies.

The test is illustrated in flow chart form in FIG. 11 as a process 300.

At step 302, a blood-derived sample is obtained from the patient. The sample in this example is plasma, after some processing steps on the sample (e.g., plasma obtained from whole blood by a prior density-separation method). In one embodiment, the blood-derived samples are separated into three aliquots and the mass spectrometry and subsequent steps 304, 306 (including sub-steps 308, 310 and 312), 314, 316 and 318 are performed independently on each of the aliquots. The number of aliquots can vary, for example there may be 4, 5 or 10 aliquots, and each aliquot is subject to the subsequent processing steps.

At step 304, the sample (aliquot) is subject to mass spectrometry. A preferred method of mass spectrometry is matrix assisted laser desorption ionization (MALDI) time of flight (TOF) mass spectrometry, but other methods are possible, including the so-called "DeepMALDI" method of mass spectrometry disclosed in pending U.S. patent provisional application 61/652,394 filed May 29, 2012, the content of which is incorporated by reference herein (see description below). Mass spectrometry produces mass spectra consisting of data points that represent intensity values at a multitude of mass/charge (m/z) values, as is conventional in the art. In one example embodiment, the samples are thawed and centrifuged at 1500 rpm for five minutes at four degrees Celsius. Further, the samples may be diluted 1:10, or 1:5, in MilliQ water. Diluted samples may be spotted in randomly allocated positions on a MALDI plate in triplicate (i.e., on three different MALDI targets or "spots" as they are known in the art). After 0.75 ul of diluted sample is spotted on a MALDI plate, 0.75 ul of 35 mg/ml sinapinic acid (in 50% acetonitrile and 0.1% trifluoroacetic acid (TFA)) may be added and mixed by pipetting up and down five times. Plates may be allowed to dry at room temperature. It should be understood that other techniques and procedures may be utilized for preparing and processing samples in accordance with the principles of the present invention.

Mass spectra may be acquired for positive ions in linear mode using a Voyager DE-PRO or DE-STR MALDI TOF mass spectrometer with automated or manual collection of the spectra. (Of course, other MALDI TOF instruments could be used, e.g., instruments of Bruker Corporation). Seventy five or one hundred spectra are collected from seven or five positions within each MALDI spot in order to generate an average of 2,000 spectra for each sample specimen. Spectra are externally calibrated using a mixture of protein standards (Insulin (bovine), thioredoxin (*E. coli*), and Apomyglobin (equine)).

Note that the DeepMALDI methods may be used in step 304, see description below, either over one MALDI plate spot or over several MALDI plate spots.

At step 306, the spectra obtained in step 304 are subject to one or more pre-defined pre-processing steps. The pre-processing steps 306 are implemented in a general purpose computer using software instructions that operate on the mass spectral data obtained in step 304. The pre-processing steps 306 include background subtraction (step 308), normalization (step 310) and alignment (step 312). The step of background subtraction preferably involves generating a robust, asymmetrical estimate of background in the spectrum and subtracts the background from the spectrum. Step 308 uses the background subtraction techniques described in U.S. Pat. No. 7,736,905, which is incorporated by reference herein. The normalization step 310 involves a normalization of the background subtracted spectrum. The normalization can take the form of a partial ion current normalization, or a total ion current normalization, as described in U.S. Pat. No. 7,736,905. Step 312 as described in U.S. Pat. No. 7,736,905 aligns the normalized, background subtracted spectrum to a predefined mass scale, which can be obtained from investigation of the spectra in the training set used by the classifier. The preprocessing steps are also described in some detail in the above discussion of the GI-4000+gemcitabine clinical study. However, the specifics of the pre-processing, e.g., features or spectral regions used for partial ion current normalization and alignment, may vary.

Once the pre-processing steps 306 are performed, the process 300 proceeds to step 314 of obtaining integrated intensities in the spectrum over predefined m/z ranges. The normalized and background subtracted intensity values may be integrated over these m/z ranges. This integrated value (i.e., the sum of intensities within the corresponding pre-defined m/z range) is assigned to a feature. Predefined m/z ranges may be defined as the interval around the average m/z position of the corresponding feature with a width corresponding to the peak width at this m/z position. This step is also disclosed in further detail in U.S. Pat. No. 7,736,905.

At step 314, in one possible embodiment the integrated values of intensities in the spectrum are obtained at one or more of the following m/z ranges:

TABLE 3

| |
|---|
| 5732 to 5795 |
| 5811 to 5875 |
| 6398 to 6469 |
| 11376 to 11515 |
| 11459 to 11599 |
| 11614 to 11756 |
| 11687 to 11831 |
| 11830 to 11976 |
| 12375 to 12529 |
| 12502 to 12656 |
| 23183 to 23525 |
| 23279 to 23622 and |
| 65902 to 67502. |

In one embodiment, values are obtained up to eight m/z ranges centered at or encompassing the peaks listed in Table 4 below. The significance, and methods of discovery of these peaks, is explained in the U.S. Pat. No. 7,736,905, and in U.S. application Ser. No. 12/932,295 filed Feb. 22, 2011, published as US 2011/0208433, the contents of which are incorporated by reference herein. In practice the above widths (ranges) or peak positions in Tables 3 and 4 may vary slightly, e.g., due to variation in how spectral alignment is performed. It has been further noted that using the "Deep-MALDI" technique (see description below) many features are revealed in the spectrum which could be used for classification. For dilute and shoot mass spectrometry one or more of the peaks of Table 1 could be used for classification, or combinations of the features of Table 1 and Tables 3 and 4. It has been further noted that using the "DeepMALDI" technique many features are revealed in the spectrum, combinations of which could be used for classification, see Tables 2, 5 and 6 and the examples of FIGS. 4A-4H described above.

At step 316, the values obtained at step 314 are supplied to a classifier, which in the illustrated embodiment is a K-nearest neighbor (KNN) classifier. The classifier makes use of a training set of class labeled spectra from a multitude of other patients. The training set will include class-labeled spectra from patients that either benefitted or did not benefit from immune response generating therapies, such as yeast-based immunotherapy for cancer, which may be yeast-based immunotherapy for mutated Ras-positive cancer, either alone or in combination with other anti-cancer therapy. For example, the training set in the GI-4000 study described in the working example above included class-labeled spectra that were in the "Quick" and "Slow" time to recurrence groups. The class labels assigned to such spectra would take the form of "Quick", "Slow", or the equivalent, such as for example "benefitted", "non-responder", "good", "poor", etc. The application of the KNN classification algorithm to the values at 314 and the training set is essentially a distance calculation and majority vote algorithm from comparison of integrated intensity values with predefined spectral features in a multidimensional feature space, as explained in U.S. Pat. No. 7,736,905. Other classifiers can be used, including a probabilistic KNN classifier, support vector machine, or other classifier.

At step 318, the classifier produces a label for the spectrum, e.g., "Quick" or "Slow". The method can be performed with a single aliquot, or with the sample separated into three aliquots, in which steps 304-318 are performed in parallel on the three separate aliquots from a given patient sample (or whatever number of aliquots is used). At step 320, a check is made to determine whether all the aliquots produce the same class label. If not, an undefined (or Indeterminate) result is returned as indicated at step 322. If all aliquots produce the same label, the label is reported as indicated at step 324.

As described in this document, the class label reported at step 324 is then used to guide the treatment of the patient. For example, those pancreatic cancer patients labeled "Quick" in accordance with the classification step are predicted as being unlikely to benefit from treatment from immune response generating therapies, such as yeast-based immunotherapy for cancer, which may be yeast-based immunotherapy for mutated Ras-positive cancer, either alone or in combination with other anti-cancer agents including gemcitabine. As another example, if the class label for the spectrum of the pancreatic cancer patient after classification is identified as "Slow" in accordance with the test, then the patient is predicted as likely to benefit from immune response generating therapies, such as yeast-based immunotherapy for cancer, which may be yeast-based immunotherapy for mutated Ras-positive cancer, either alone or in combination with gemcitabine, and the patient proceeds to be treated by administration with the immune response generating therapy, such as yeast-based immunotherapy for cancer, which may be yeast-based immunotherapy for mutated Ras-positive cancer, alone or in combination with gemcitabine.

It will be understood that steps 306, 314, 316 and 318 are typically performed in a programmed general purpose computer using software coding the pre-processing steps 306, the obtaining of integrated intensity values in step 314, the application of the KNN classification algorithm in step 316 and the generation of the class label in step 318. The training set of class labeled spectra used in step 316 is stored in memory in the computer or in a memory accessible to the computer.

The method and programmed computer may be advantageously implemented at a laboratory test processing center as described in U.S. Pat. No. 7,736,905.

TABLE 4

| Peaks used in classification. | |
|---|---|
| Peak number | m/z |
| 1 | 5843 |
| 2 | 11445 |
| 3 | 11529 |
| 4 | 11685 |
| 5 | 11759 |
| 6 | 11903 |
| 7 | 12452 |
| 8 | 12579 |

Note: the m/z values of the peaks identified in Table 4 may be subject to slight shifting to higher or lower m/z values depending on the spectral alignment process which is used to align all the spectra used in the training set, and in aligning the test spectrum in pre-processing.

Figure 12:
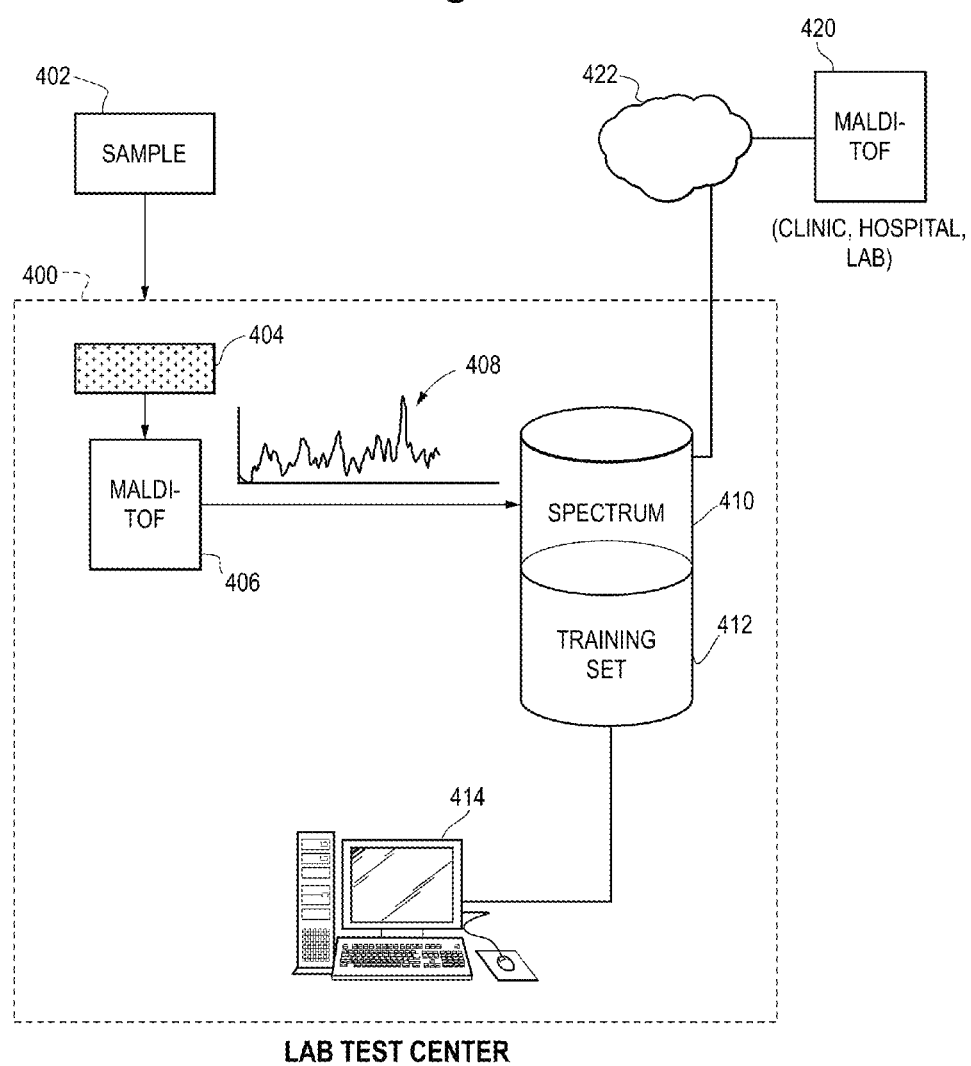
FIG. 12 is an illustration of a system for performing testing of a blood-derived patient sample and predicting whether the patient is likely to benefit from an immune response generating therapy either alone or in combination with another anti-cancer agent.

FIG. 12 is a schematic block diagram of a laboratory test processing system 400 which may be used to practice the methods of this disclosure. The system 400 may be implemented in a laboratory functioning as a laboratory test processing center for a multitude of patient samples, e.g., in a test service provider business. The system 400 receives a blood-derived sample 402, which may be whole blood, plasma, serum, or plasma after performance of other processing steps, e.g. plasma obtained from whole blood by a prior density-based separation method. The sample is diluted and aliquoted using procedures described above onto one or more spots of a MALDI-TOF pate 404 which is then inserted into a MALDI-TOF mass spectrometer 406. The mass spectrometer generates a mass spectrum 408, which is in the form of data pairs (m/z position, intensity) as is conventional. The mass spectral data is then stored in digital form in a database or machine readable memory 410. The memory 410 is accessible a general purpose computer 414, e.g., via a local area network, the details of which are not important. The memory 410 further stores the class-labeled spectra of a training set 412. The computer 410 implements software instructions for performing the pre-processing steps on the spectrum 408 (background subtraction, normalization and alignment) and code for executing a classification algorithm (e.g. K-nearest neighbor) with respect to the spectrum after pre-processing and using the training set data 412. The computer then generates a class label for the spectrum 408 as explained in FIG. 11, which is used to guide treatment as disclosed herein.

The test system 400 can receive mass spectral data from a remote MALDI-TOF instrument 420 via a computer network 422 and perform steps 304-324 of FIG. 11. The MALDI-TOF instrument could be associated with a remote clinic, hospital, or laboratory, which may or may not be affiliated with the entity that is implementing the classification computer 414, however to ensure standardization and reproducibility normally the same entity that performs classification and generation of the class label will also be performing the mass spectrometry of the patient sample.

"DeepMALDI" Methods for Obtaining Mass Spectra

In MALDI (matrix assisted laser desorption ionization) TOF (time-of-flight) mass spectrometry, a sample/matrix mixture is placed on a defined location ("spot", or "sample spot" herein) on a metal plate, known as a MALDI plate. A laser beam is directed onto a location on the spot for a very brief instant (known as a "shot"), causing desorption and ionization of molecules or other components of the sample. The sample components "fly" to an ion detector. The instrument measures mass to charge ratio (m/z) and relative intensity of the components (molecules) in the sample in the form of a mass spectrum.

Typically, in a MALDI-TOF measurement, there are several hundred shots applied to each spot on the MALDI plate and the resulting spectra (one per shot) are summed or averaged to produce an overall mass spectrum for each spot.

The conventional wisdom, at least in the area of MALDI-TOF mass spectrometry of complex biological samples such as serum and plasma, is that there is no need to subject the sample to more than roughly 1,000 shots, otherwise the protein content is depleted, the laser and detector in the instrument are subject to undue wear, and furthermore that additional shots would not reveal a significant amount of additional information regarding the sample. Hence, it is common to use 500-1000 shots per sample spot when obtaining mass spectrometry data from complex biological samples, e.g., during biomarker discovery research.

In recent exploratory studies, we have discovered that collecting and averaging many (more than 20,000, and typically 100,000 to 500,000) shots from the same MALDI spot or from the combination of accumulated spectra from multiple spots of the same sample, leads to a reduction in the relative level of noise vs. signal and that significant amount of additional spectral information from mass spectrometry of complex biological samples is revealed. Moreover, a variety of standard paradigms using MALDI TOF MS appear to be plain wrong. First, it is possible to run hundreds of thousands of shots on a single spot before the protein content on the spot is completely depleted. Second, the reduction of noise via averaging many shots leads to the appearance of previously invisible peaks (i.e., peaks not apparent at 1,000 shots). Third, even previously visible peaks become better defined and allow for more reliable measurements of peak intensity and comparisons between samples when the sample is subject to a very large number of shots (much more than 1,000).

As one example, it has been discovered that subjecting a complex biological sample such as a blood-based sample to a large number of shots on a single spot (>20,000 and even 100,000 and 500,000 shots) in MALDI-TOF mass spectrometry leads to a reduction in the noise level and the revealing of previously invisible peaks (i.e., peaks not apparent at 2,000 shots). Moreover, this can be done without depletion of the protein content of the sample. Additionally, previously visible peaks become better defined and allow for more reliable comparisons between samples. In standard spectra of blood-based samples (~1,000 shots), typically 60-80 peaks are visible, whereas with 200,000 shots typically ~200-220 peaks are visible, with 500,000 shots typically ~450-480 peaks are visible, and with 2,800,000 shots typically ~760 peaks are visible. It should be understood that the number of peaks reported here is related to MALDI-TOF instrument settings and these numbers are only a rough guide; depending on instrument settings and also on particular peak detection algorithms (and of course the actual sample) more or fewer peaks will be visible. It also must be noted that the quality of peaks and the quantification of intensity (related to abundance) is also better at least under some measure, as is illustrated in FIGS. 16A-16D discussed below.

The peaks revealed at, for example, 200,000 shots are believed to correspond to minute quantities of intact (undigested) proteins present in the serum sample. Using the techniques described herein and what is referred to herein as the "DeepMALDI" approach (i.e., greater than 20,000 shots per spot, and preferably roughly 250,000 to 750,000 or more shots from the same spot or from the combination of multiple spots), it is believed that a very large number of proteins, and possibly at least half of all the proteins present in a serum sample, can be detected in a semi-quantitative and reproducible fashion. The detection in a semi-quantitative fashion means that the measurements of intensity (peak height, area under the peak) are related to the absolute abundance or concentration of the proteins in the sample. The detection in a reproducible fashion means that one can measure the same sample many times and one obtains the same results within some acceptable coefficient of variation.

Obtaining more than 20,000 shots from a single MALDI spot can exceed the parameters of a modern MALDI-TOF machine; however we describe in this document several methods of working around this limitation. Ideally, the MALDI-TOF instrument is designed to accommodate the "DeepMALDI" approach described in this document, and several specific proposals for such a machine are offered in the following description, including automated raster scanning features and capability of performing vastly more shots on a single spot.

The most pressing issue using many hundreds of thousands of shots from a MALDI sample spot is that in common spot preparation only some shot locations within a spot yield sufficient ion current to contribute substantially to signal in a combined spectrum. While initial results have been obtained using a labor intensive manual process to visually select high ion yield locations within a given spot on a MALDI plate for laser shots, and it is possible to proceed with this approach, automation of the process to select locations for laser shots is possible and preferred for a high throughput implementation of the invention (if not for the simple reason to not waste too many laser shots and degrade the laser life time substantially). An alternative approach is to improve the quality of MALDI spots in such a way that most randomly selected locations yield a high ion current. Both approaches are useful in the generation of Deep-MALDI spectra.

Several methods for automation of spectral acquisition are described in this section of this document. Automation of the acquisition may include defining optimal movement patterns of the laser scanning of the spot in a raster fashion, and generation of a specified sequence for multiple raster scans at discrete X/Y coordinate locations within a spot to result in say 750,000 or 3,000,000 shots from one or more spots. For example, spectra acquired from 250,000 shots per each of four sample spots can be combined into a 1,000,000 shot spectrum. As mentioned previously, hundreds of thousands of shots to millions of shots collected on multiple spots containing the same sample can be averaged together to create one spectrum. One method of automation involves the generation of raster files for non-contiguous X/Y raster scanning of a sample spot. Another method involves dividing the spot into a grid of sub-spots (e.g., a 3×3 or 5×5 grid) and generating raster files for raster scanning at discrete X/Y coordinate locations of the sub-spots. A third method is disclosed using image analysis techniques to identify areas of interest containing relatively high concentrations of sample material for spectral acquisition (multiple shots) and/or those areas where the protein concentration is relatively low, and performing spectral acquisition in the areas with relatively high protein concentration.

An optimizing the process of sample application to the MALDI plate ("spotting") to produce uniform, homogeneous crystals of the sample/matrix within a single spot is described below. This process facilitates obtaining hundreds of thousands of shots from a single spot on the MALDI plate using automated methods.

This discovery and methods of this disclosure has many applications, including biomarker discovery, test development, substance testing, validation of existing tests, and hypothesis generation, e.g., in biomarker discovery efforts. It is specifically contemplated that the methods are applicable to the predictive tests described elsewhere in this document. The methods further enhance the potential of "dilute and shoot" methods in mass spectrometry research by its ability to reproducibly quantify the amount of many more proteins in a complex sample in a high throughput fashion, as compared to current methodologies.

Terminology used in this section of this document:

1. The term "transient spectrum" refers to the spectrum obtained from a single packet of laser shots directed to a single location or x/y position (each packet consists of a defined number of shots, e.g., 100, 500, 800 shots, etc.) in a MALDI spot.

2. The term "location spectrum" refers to the cumulative sum of one or more transient spectra while the laser shoots x times at the same location in a MALDI spot.

3. The term "spot spectrum" refers to the sum of all the location spectra acquired during shooting over an entire, single MALDI spot. The spot spectrum can be obtained using solely a summing operation to sum the location spectra, or obtained using a summing operation after performing alignment and/or normalization operations (e.g., total ion current normalization) on the location spectra. The spot spectrum can be typically obtained from 100,000 to 500,000 shots on the MALDI spot. Other options for obtaining the spot spectrum are possible, including a) performing background subtraction and normalization on the location spectra and then summing; b) performing background subtraction and alignment on the location spectra and then summing; c) performing background subtraction, alignment, and normalization of the location spectra and then summing. We have found that the best dynamic range is achieved by total ion current normalization (for details see U.S. Pat. No. 7,736,905) of location spectra and then summing; any background subtraction would be done in the spot spectrum.

4. The term "shot location" refers to a given location where the laser beam intercepts a MALDI spot for shooting. In order to obtain 200,000 or 500,000 shots per MALDI spot the laser beam is directed over the MALDI spot to a multitude (e.g., hundreds) of individual shot locations, e.g., manually, or more preferably in an automated fashion using raster scanning of the laser beam over the spot. As explained below, the raster pattern design is important as it is generally undesirable to shoot immediately adjacent spot locations sequentially. Hence, the raster pattern design sequentially selects shot locations that have some spatial separation and repeats the scanning over the entire MALDI spot in a spatially shifted manner to avoid sequential shooting of immediately adjacent locations in the spot.

5. The term "transient spectrum filtering" refers to a filtering or selection process that is used to either accept or reject a transient spectrum. As an example, in transient spectrum filtering, in order for a transient spectrum to be accepted a minimum number (e.g., 5) of peaks within a predetermined m/z range must be present in the transient spectrum, and the signal to noise ratio in the transient spectrum must be above a specified threshold. Other filtering criteria can also be used, such as the total ion current of a spectrum needs to exceed a certain predefined threshold, or by using exclusion lists or inclusion lists as explained below. The spectrum filtering either accepts or rejects the transient spectrum in whole.

6. As used herein, the term "complex biological samples" is defined as samples containing hundreds or thousands of analytes, e.g., intact proteins, whose abundance is spread over a large dynamic range, typically many orders of magnitude. Examples of such complex biological samples include blood or components thereof (serum or plasma), lymph, ductal fluids, cerebrospinal fluid, and expressed prostate serum. Such complex biological samples could also consist of environmental or food samples.

Figure 16A:
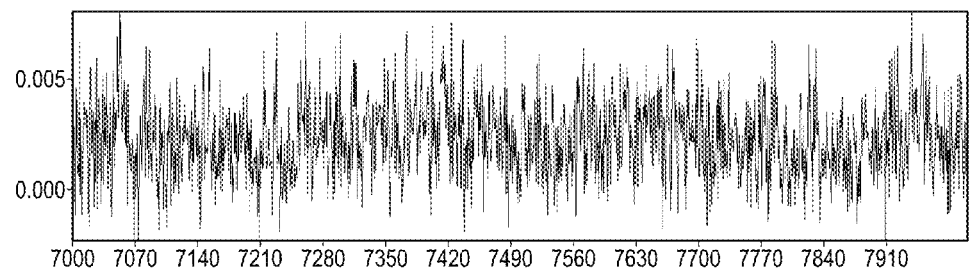
FIGS. 16A-16C are an illustration of three MALDI mass spectra of the same sample in a selected mass/charge range (m/z ratio 7,000 to 8,000), illustrating the increase in detectable peak content with increasing number of shots. The spectrum of FIG. 16A resulted from 2,000 shots, the spectrum of FIG. 16B resulted from 100,000 shots, and the spectrum of FIG. 16C resulted from 500,000 shots. Note how the spectra of FIGS. 16B and 16C, resulting from our methods, reveal a wealth of spectral information on the sample which was not present in the spectrum of FIG. 16A, which appears essentially as noise.
Figure 16B:
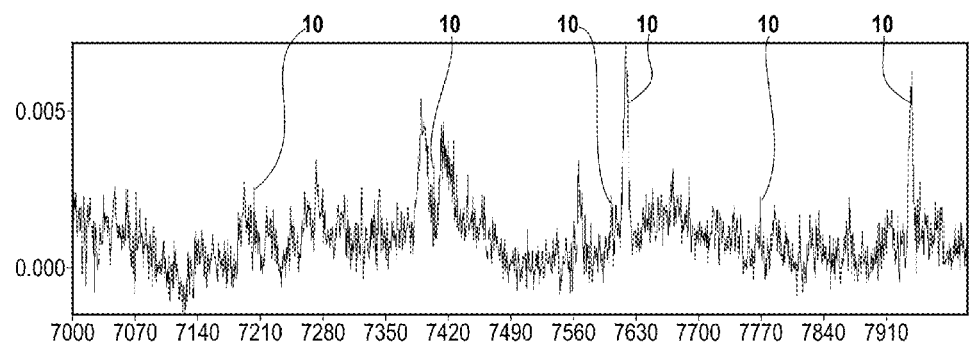
Figure 16C:
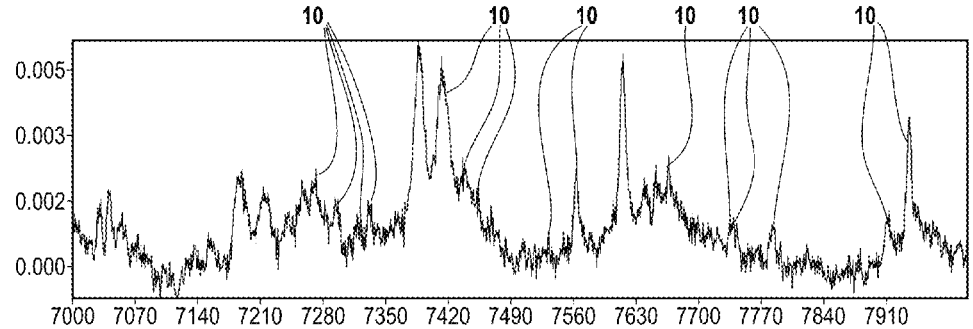

An example of the spectral information revealed in the "DeepMALDI" method is shown in FIGS. 16A-16E. FIGS. 16A-16C are the plots of a selected mass/charge range (m/z ratio 7,000 to 8,000) showing three spectra of the same sample (serum) illustrating the increase in detectable peak content with increasing number of shots. The spectrum of FIG. 16A resulted from 2,000 shots, the spectrum of FIG. 16B resulted from 100,000 shots, and the spectrum of FIG. 16C resulted from 500,000 shots. Note particularly how the spectrum of FIG. 16A appears essentially as noise and appears to contain little or no discernible spectral information of interest. Contrast FIG. 16A with 16B in which the spectrum of FIG. 16B (spectrum obtained from 100,000 shots) contains many individual peaks, e.g., the peaks identified at 10), that are not present in the spectrum of FIG. 16A. In the spectrum of FIG. 16C, there are many peaks shown in the spectrum that are not shown in the other spectra, or which might have been deemed as noise in the bottom spectrum. Comparing FIGS. 16C and 16B to FIG. 16A it is apparent that a wealth of spectral information is revealed at 100,000 shots and 500,000 shots that is not present in the spectrum of FIG. 16A (2,000 shots), and that the noise level is reduced by the DeepMALDI method as demonstrated in FIGS. 16B and 16C.

The spectra of FIGS. 16B are 16C increase the sensitivity of the spectra to a dynamic range that can be specified and can allow one to correlate peak intensity to abundance. It is possible to use peak intensity to analyze a complex biological sample for presence of a molecule at a given concentration. For example, in this method one would define the molecule of interest (of known mass) in the sample, dope the specimen to a target abundance level (molar concentrations, or ppm) and apply to a MALDI plate; perform a number of shots on the plate (e.g., more than 100,000) until the molecule is reliably present in the spectrum (a peak at a known m/z position) at a particular abundance (intensity), and record the number of shots ("x"). This procedure to generate what is referred to as a "reference spectrum" would be subject to routine qualification and standardization methods to ensure reliability, as would be apparent to persons skilled in the art. Then, a sample of interest for testing would be subject to MALDI-TOF and x number of shots. If the resulting spectrum revealed that the intensity of the peak at the known position corresponding to the molecule of interest was less than the intensity of the peak in the reference spectrum then the concentration of the molecule of interest in the sample is less than the concentration of the molecule in the sample used in generation of the reference spectrum. This approach could be used for multiple analytes simultaneously. Furthermore, multiple reference spectra could be obtained for the molecule of interest over a range of known concentrations at x shots and the test spectrum could be compared to the reference spectra to determine an approximate concentration of the molecule of interest in the test sample. This method can be used for many purposes, e.g., drug testing, e.g., of an athlete, testing of metabolite concentration, environmental sample testing, etc. The molecule of interest could be a protein, e.g., metabolite, Cancer Antigen (CA) 125, prostate-specific antigen (PSA), C-reactive protein, etc., in a mass range of approximately 1K Daltons to 50 K Daltons.

Figure 16D:
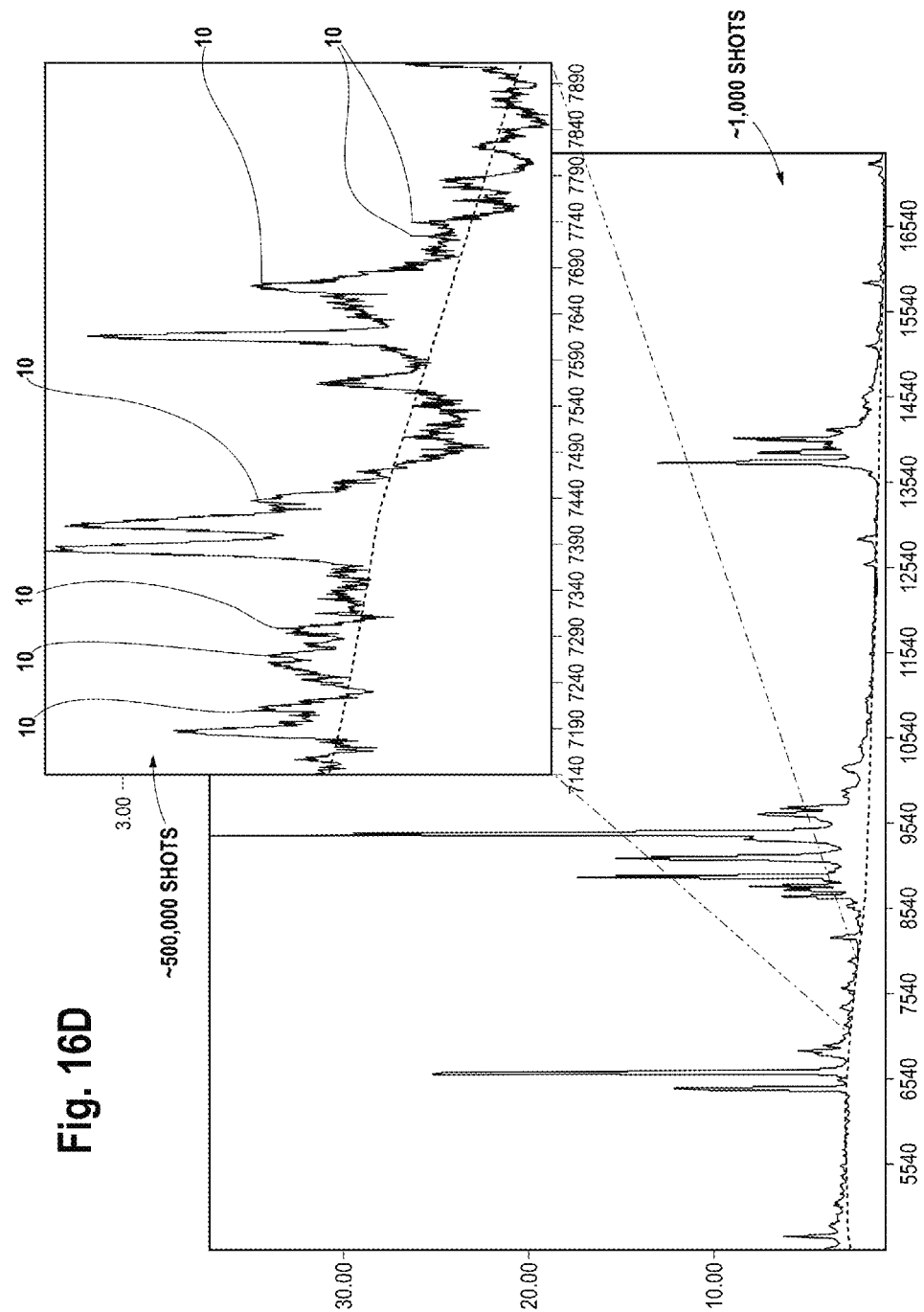
FIGS. 16D and 16E are further examples of mass spectra showing the enormous dynamic range of spectra obtained in our DeepMALDI method.
Figure 16E:
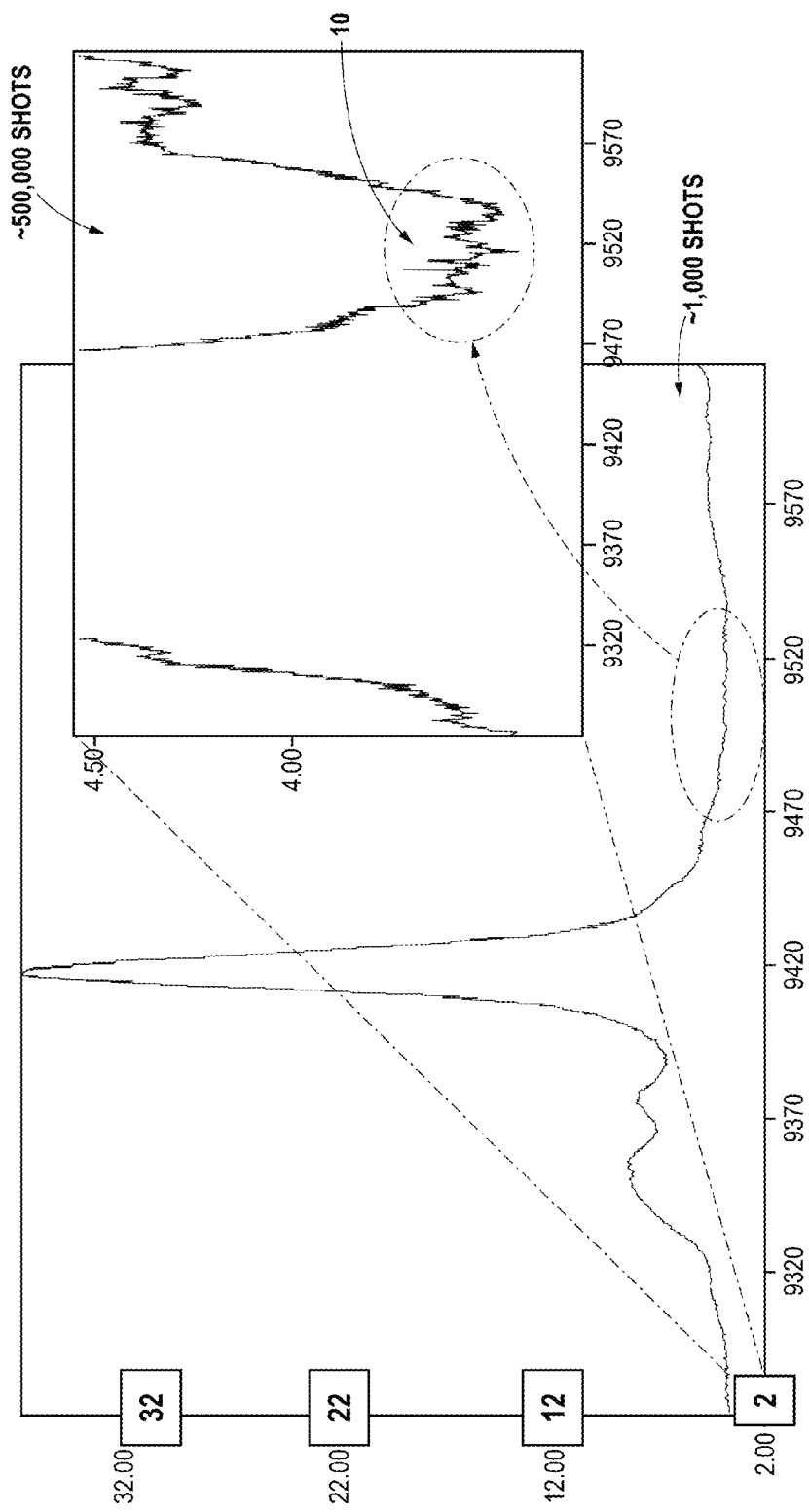

FIG. 16D is an illustration of the enormous dynamic range in a spectrum that is revealed in the DeepMALDI approach. The inset in FIG. 16D is a portion of a spectrum in the m/z range between 7140 kDa and 7890 kDa showing the spectrum, and multitude of peaks 10, obtained at about ~500,000 shots. A background estimate (dashed line) is superimposed over the spectra, which could be subtracted out to produce a background subtracted spectrum. Note that the spectrum information in the inset and in particular many of the peaks 10 are not visible in the main portion of FIG. 16D. In FIG. 16E, the spectrum is shown in the inset with the Y axis amplified in order to show the additional spectral information and in particular intensity information for peaks in the region of m/z around 9520 which are revealed with the DeepMALDI method but which are not visible in a typical ~1,000 shot spectrum.

FIG. 16A is a plan view of a MALDI-TOF target plate 12 containing 384 sample spots or "spots" 14 arranged in a rectangular array. The spots are identified by column numbers 1 . . . 24 and rows A . . . P, e.g., the upper left spot is identified as A1. FIG. 16B is an enlarged view of an individual sample spot P1 (14) on which is superimposed an X/Y coordinate system 16 having an origin (0,0). The sample spot 14 is shown divided into a 5×5 rectangular grid 25 individual sub-spots 18. The rectangular grids 18 and location coordinate system 16 are used in an automated raster scanning approach to acquire 100,000 or more shots from the spot as described in detail below.

It was initially noted that automated generation of a large number of shots (>20,000) is not absolutely necessary and existing features in currently available MALDI-TOF instruments could be used. In general, in the present DeepMALDI technique, it is important to select locations on a MALDI spot that produce a high protein yield when exposed to a laser shot. The standard software in existing mass spectrometry instruments allows for moving over a spot using regular pre-defined paths, i.e. square pattern, hexagonal pattern, spiral pattern (from the center of a spot). Shot locations on a MALDI plate are defined in a process called 'teaching', a part of the FlexControl™ (Bruker) mass spec control software present in an existing MALDI-TOF instrument of Bruker Corporation. (While mention is made herein occasionally to features of a Bruker Corporation instrument, the inventive methods are of course not limited to any particular instrument or instruments of a particular manufacturer.)

Figure 18:
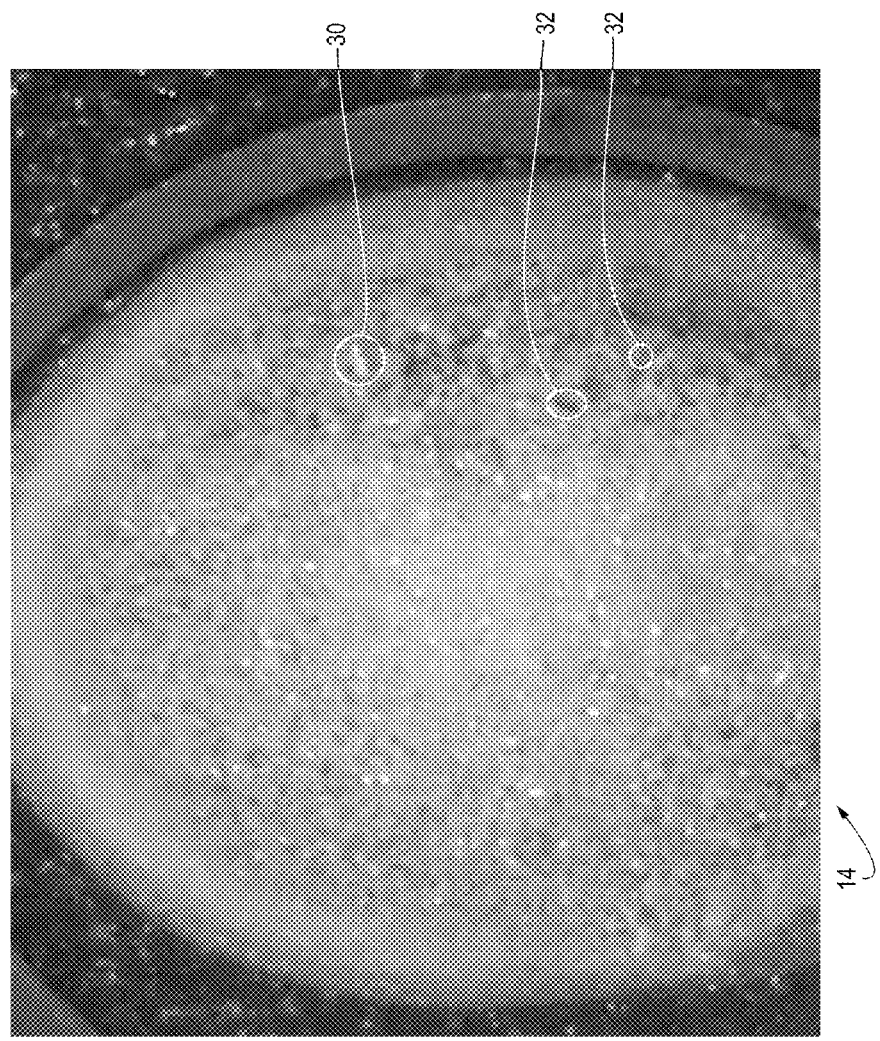
FIG. 18 is a photograph of a biological sample/matrix mixture deposited in a single spot in the MALDI plate of FIG. 17A. Ideally, the spot contains a uniform, homogenous crystallized sample within the spot, as shown in FIG. 18.

An example of a MALDI spot containing a specimen/matrix mixture evenly distributed within the spot is shown in FIG. 18. Mass spectrometry instruments from Bruker Corporation include a built-in camera that shows areas of a MALDI spot; in manual selection one would pick bright locations 30 to aim the laser at. Dark locations 32 should be avoided. Sometimes bright locations do not produce good yields, which may be related to the presence of salt crystals. Over the process of shooting, areas in a spot can become depleted; hence dark areas (depleted areas with low yield) need to be avoided. The manual approach would continue to acquire and display images of the spot over the course of shooting.

In the course of our preliminary experiments we found that it was becoming increasingly harder to find good locations as more and more shots were used. This effect was also seen when the same spot was used repeatedly, e.g. adding a second half million shots following a previous half million shots. The second run did not result in as much a reduction of noise level in mass spectra as was expected. In fact, the resulting averaged spectra may be of worse overall quality, possibly arising from averaging shots from too many empty locations. This might result in an acquisition bias towards early locations if using the eye alone to select shot locations and accept or reject spectra and not using transient spectrum filtering, and such bias needs to be controlled. If one uses automated raster scanning and location spectrum filtering this bias is eliminated.

However, to increase throughput, it is desirable to automate the process of location selection and obtain high numbers of shots from a given spot. Several methods are described in the following section. Methods described below are capable of acquiring 750,000 shots from a sample located on three spots (250,000 shots per spot) in a MALDI plate in 13-15 minutes, with the sample requirement of 3 microliters of serum.

Automation of Spectra Collection

While results have been obtained using a labor intensive manual process to visually select locations within a given spot on a MALDI plate for multiple shots to yield 100,000 or 500,000 shots per spot, and it is possible to proceed with this approach, automation of the process to select locations for laser shots is possible and several methods are described in this document.

Automation of the acquisition may include defining optimal movement patterns of the laser scanning of the spot in a raster fashion, and sequence generation for multiple raster scans at discrete X/Y locations within a spot to result in, for example, 100,000, 250,000 or 500,000 shots from the sample spot. One method of automation involves the generation of raster files for non-contiguous X/Y raster scanning of a sample spot. The raster pattern design is important, as it is generally undesirable to shoot immediately adjacent spot locations sequentially. Hence the raster pattern design sequentially selects shot locations that have some spatial separation and repeats the scanning over the entire MALDI spot in a spatially shifted manner to avoid sequential shooting of immediately adjacent locations in the spot and to select new shot locations.

Another method involves dividing the spot into a grid of sub-spots (e.g., a 3×3 or 5×5 grid) (see FIG. 17B) and generating of raster scanning files for raster scanning at discrete X/Y locations of the sub-spots.

A third method is disclosed using image analysis techniques to identify areas of interest containing relatively high concentrations of sample material for spectral acquisition (multiple shots) and/or those areas where the sample (e.g., protein) concentration is relatively low, and avoiding spectral acquisition in areas of relatively low sample (e.g., protein) concentration.

A. Raster Scanning of Non-Contiguous X-Y Coordinates

One method of automation of the process of obtaining a large number of shots from a spot involves the generation of raster files for non-contiguous X/Y raster scanning of a sample spot. This will be described in conjunction with FIGS. 19 and 20.

Figure 19:
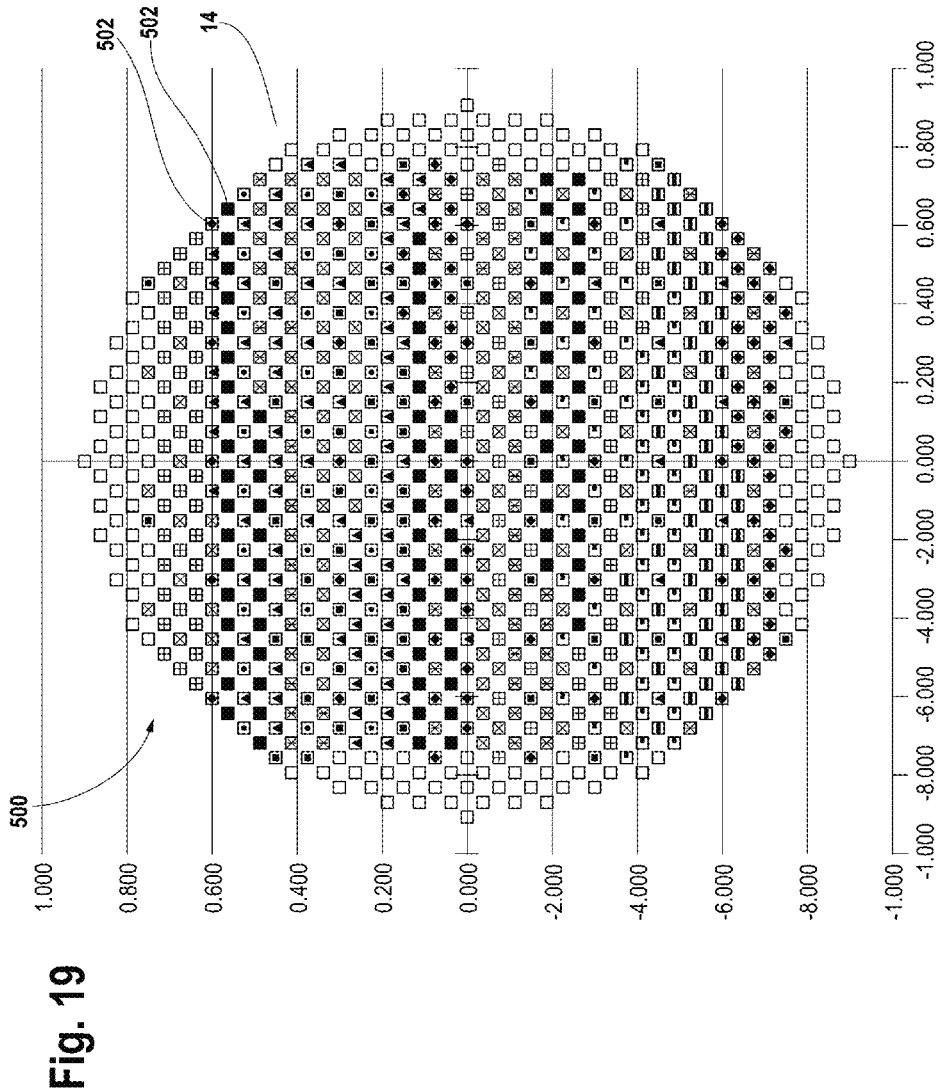
FIG. 19 is an illustration of one possible raster scanning pattern for use in obtaining 100,000 or more shots from the spot of FIG. 18. The spot is raster scanned multiple times, e.g., 25 times. Each symbol set (triangle, square, X, etc.) shown in FIG. 19 depicts a set of individual, discrete X/Y locations where the spot is scanned (shot) in a single raster scan. At each location, the spot can be subject to multiple shots, e.g., 700 or 800 shots.
Figure 20:
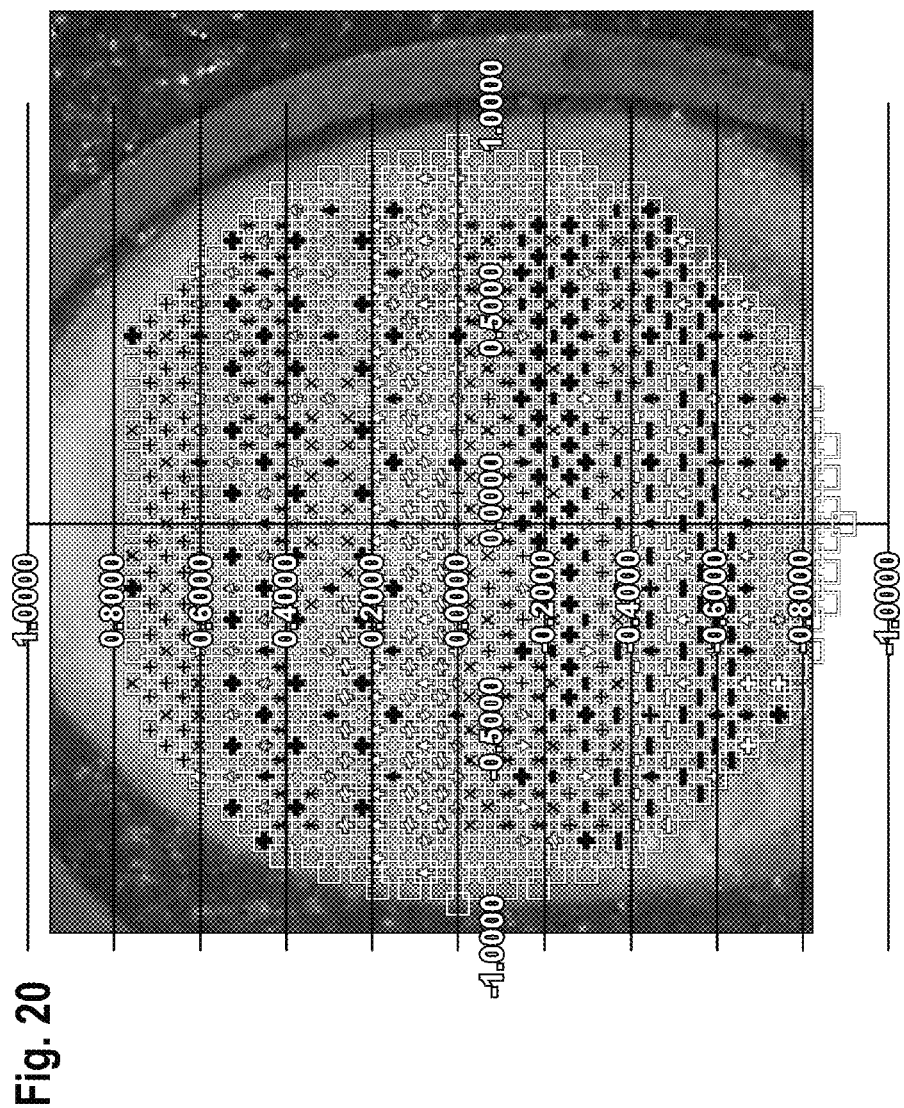
FIG. 20 is an illustration showing the superposition of the raster scanning pattern of FIG. 19 on the sample spot of FIG. 18.

FIG. 19 is an illustration of a raster scanning pattern 500 for use in obtaining 100,000 or more shots from the spot 14 of FIG. 18. The spot 14 is raster scanned multiple times, e.g., 25 times in a sequential fashion. The symbol sets 502 shown in FIG. 19 depict individual, discrete X/Y locations where the spot is scanned (shot) in a single raster scan. The X/Y locations are defined according to a coordinate system shown in the Figure having an origin at the center (position 0,0). During scanning, when the laser is directed to each location, the sample at that location can be subject to a great many shots, e.g., 700 or 800 shots per position/location. One will note from the pattern shown in FIG. 19 that each raster scan consists of shooting at individual, discrete locations within the spot. The individual raster scans are implemented sequentially thereby avoiding shooting immediately adjacent locations in the spot. FIG. 20 shows the superposition of the raster patterns of FIG. 19 over the spot of FIG. 18.

A procedure for generation of 25 raster files with non-contiguous X/Y coordinates for raster scanning as shown in FIG. 19 is described in the appendix to U.S. Provisional Application 61/652,394 filed May 29, 2012 and the interested reader is directed to that document for further reference.

B. Use of Grids to Separate a Spot into Sub-Spots and Raster Scanning of Sub-Spots An objective of this method is to automate the process of manually selecting locations/rasters on a sample spot (i.e. spot A1, spot A2, etc.) that result in "acceptable" spectra during data acquisition and to do this until several hundred thousand spectra have been added to the sum buffer. Summing up/averaging several hundred thousand spectra increases the signal to noise ratio, and therefore allows for the detection of significantly more peaks, as described previously.

As is the case with non-contiguous raster scanning described above, the use of grids as described in this section works best when the sample/matrix mixture is substantially evenly and homogeneously distributed over the entire spot, as shown in FIG. 18. A presently preferred method for achieving this is described later in this document for dilute-and-shoot serum and sinapinic acid (matrix). Because of this even distribution, we can therefore acquire spectra from virtually all locations/rasters on the sample spot, which eliminates the need for a precursory evaluation of all locations/rasters for "acceptable" spectra.

Figure 21:
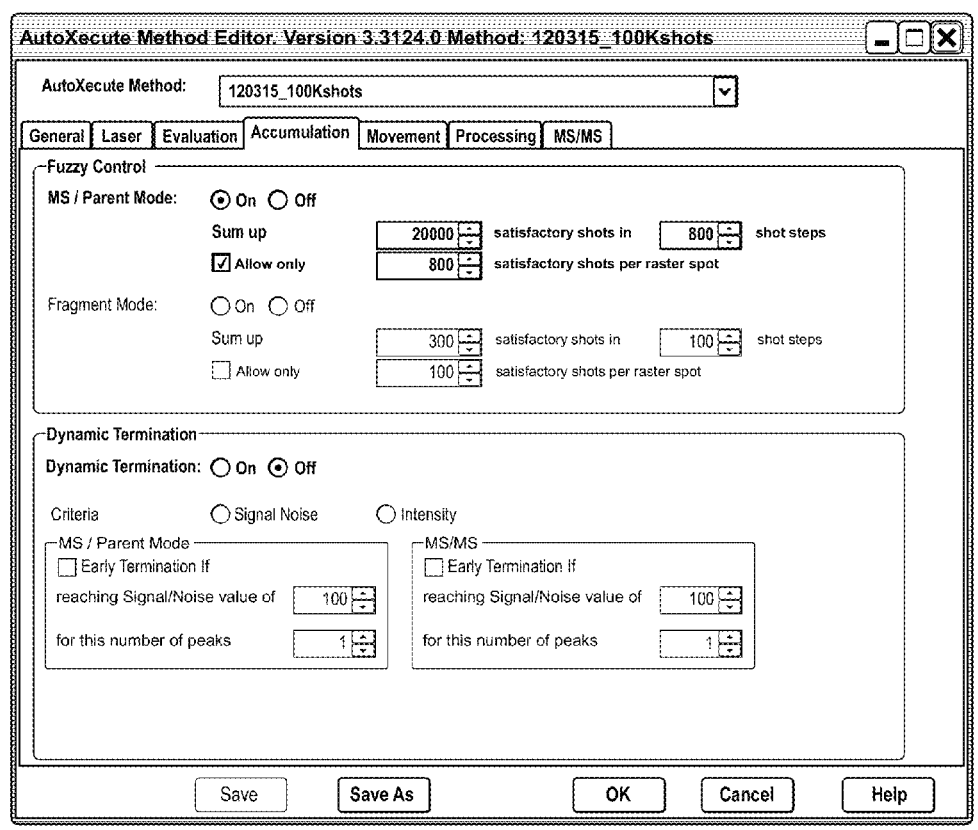
FIG. 21 is a screen shot from a MALDI-TOF instrument user interface showing commands for summing accumulated spectra from 800 laser shots per location/raster, e.g., in the raster scanning of FIG. 17B or 20.

Collecting several hundred thousand spectra on a sample spot can be achieved by defining a grid (FIG. 17B) that subdivides the spot 14 into sub-spots or grid elements 18, that covers the sample spot, and collecting a defined number of spectra from each location/grid point/raster within each sub-spot 18 until the desired number of spectra have been added to the sum buffer. Previous versions of the Bruker software only allowed for the summation of a maximum of 20,000 total spectra per sample spot in automatic mode (FIG. 21).

Figure 17A:
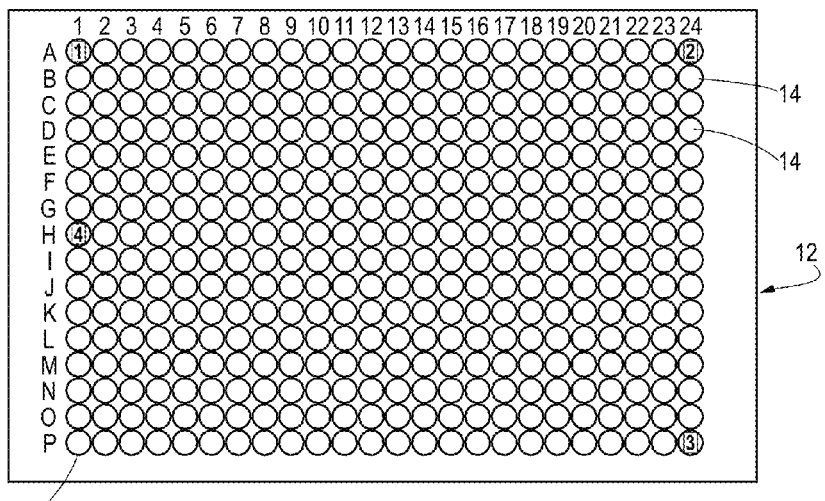
FIG. 17A is a plan view of a MALDI-TOF target plate containing 384 sample spots or "spots" arranged in a rectangular array. The spots are identified by column numbers 1 . . . 24 and rows A . . . P, e.g., the upper left spot is identified as A1.
Figure 17B:
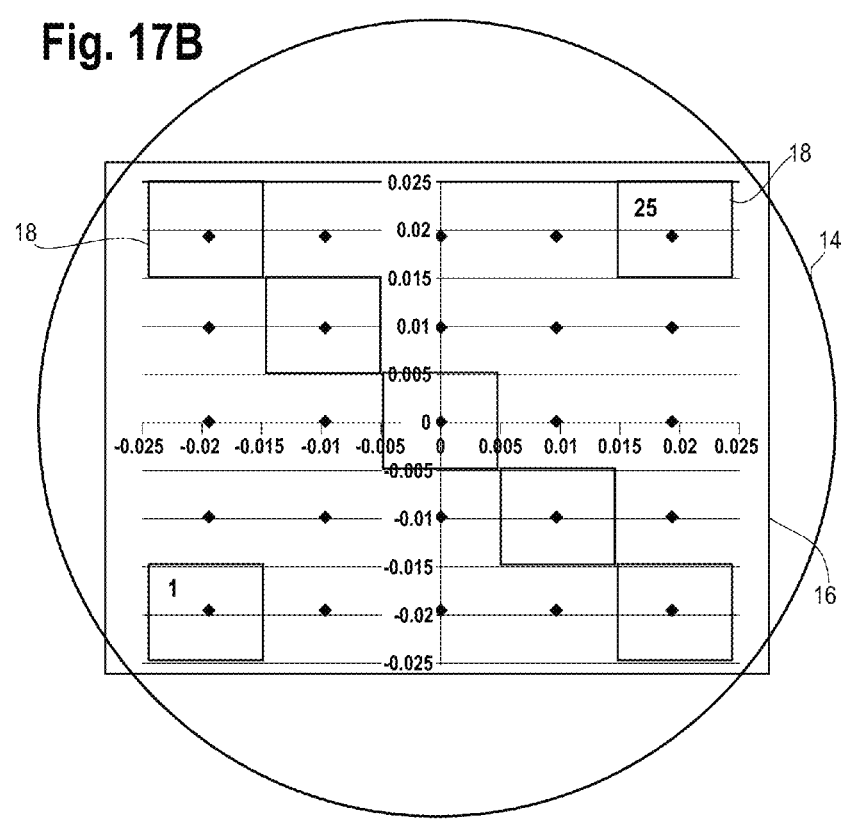
FIG. 17B is an enlarged view of an individual sample spot P1 which is shown divided into a 5×5 rectangular grid having X/Y location coordinates and an origin (0,0) at the center of the spot. The rectangular grid and location coordinates are used in an automated raster scanning approach to acquire spectra from 100,000 or more shots from the spot as described in detail herein.

To circumvent this limitation we initially defined a 5 by 5 grid area (FIGS. 17B, 16) that divides each sample spot into twenty-five 8×8 grids or sub-spots 18 (FIG. 17B). A separate raster file is generated for each grid or sub-spot 18. The instrument is instructed to acquire 800 spectra (shots) at each location/raster within a grid 18 until 20,000 spectra have been added to the (spectrum) sum buffer. At that time, the automatic method will instruct the instrument to move to the next grid or sub-spot 18 and use the next raster file and generate another 20,000 spectra. In practice, one designs 25 raster files, one for each sub-spot 18, each of which is attached to a separate AutoExecute™ (Bruker) method that acquires data according to evaluation criteria setup within the method.

This procedure permits acquisition of 500,000 shot spectra (20,000 shot spectra per grid×25 grids) in batches of 20,000 shots each using Bruker's Flexcontrol™ software tools without having to use imaging applications such as flexImaging™ (Bruker). The result of this procedure is 25 spectra files for one sample spot each containing one summed spectrum composed of 20,000 shot spectra. These 25 spectra files can then be summed to produce an overall spectrum for a single spot on a MALDI plate obtained from 500,000 shots, e.g., as shown in FIGS. 16C, 16D and 16E.

The most recent version of Flexcontrol™ (Bruker) allows one to accumulate a summed spectra from up to 500,000 shots. For example, in FIG. 21 the AutoExecute™ (Bruker) method editor allows the summation of 20,000 shots in 800 shot steps (800 shots per location/raster).

However, one can only collect one summed spectra (sum of x transient spectra) per sample spot. To acquire several batches of summed spectra from a single sample spot, we had to make adjustments to existing software features in the MS instrument. With these adjustments we can acquire spectra from one or several rasters that makes up a grid such as the ones described above, and save each transient or location spectrum individually. For instance, the instrument can be instructed to collect and save each 800 shot location spectra acquired at each raster (x,y position) in the grid or sub-spot 18 in FIG. 17B without having to add to the sum buffer. The same process is repeated for all the sub-spots within the sample spots A1, A2, A3 etc. (e.g. 800 shot spectra can be acquired from 250 rasters per sample spot=200,000 shots per sample spot). The location spectra can be acquired with or without applying spectrum filtering in AutoExecute™ (Bruker).

C. Image Analysis

One option for automation of spectral acquisition is image processing techniques to identify spatial locations on a spot with high protein yield/high sample concentration particularly in the situation where the sample is not spatially evenly distributed over the spot and instead is concentrated in discrete areas. In one possible embodiment, the camera included in the instrument is used to acquire an optical image of a training spot. Then, mass spectra are acquired from a raster of locations on the training spot. Resulting mass spectra are used, in combination with the optical image of the spot, to generate a classification mechanism to detect, from the optical image, high yield locations of further spots prepared from a given sample preparation. This classification would then be applied to the actual sample spots. While this is an elegant solution, we encountered issues with capturing the camera feed, and the repeatable calibration of locations from camera images to laser shot locations.

An alternative method is to investigate a spot using the mass spectrometer directly in the form of a mass spectral imaging approach. The idea is to first run a preliminary scan and shoot a low number of shots (dozens) at each location of a fine scale (square) pattern on a spot. Spectra will be collected for each of these raster locations, and the total ion current, or ion current within some predefined range of m/z, will be recorded for each location. A new raster file will be generated based on the N highest intensity locations from the preliminary scan run, and used in the final acquisition of mass spectra. This approach utilizes the Bruker FlexImaging™ software as the most feasible solution to generate multiple spectra in the mass spec imaging run. Software analyzes these spectra, and generates a final raster scan pattern. While this method will likely be useful for standard dilute and shoot processes using sinapinic acid as a matrix, it might be suboptimal for other matrices and for pre-fractionated sample sets (e.g. CLCCA, see Leszyk, J. D. Evaluation of the new MALDI Matrix 4-Chloro-a-Cyanocinnamic Acid, J. Biomolecular Techniques, 21:81-91 (2010)), and other methods like NOG precipitation (Zhang N. et al., Effects of common surfactants on protein digestion and matrix-assisted laser desorption/ionization mass spectrometric analysis of the digested peptides using two-layer sample preparation. Rapid Commun. Mass Spectrom. 18:889-896 (2004)). An important aspect of this alternative method is to find acquisition settings in the MS imaging part so as to not generate too large files. A standard acquisition file is of the order of one megabyte, and for a 400 by 400 raster scan (400 locations, 400 shots per location) we generate 16,000 spectra. As the requirements for these spectra are not onerous at all, and we only need to estimate the total ion current, we can work with low resolution settings. It may be possible to directly obtain a list of usable locations from automatic spectral acquisition settings, i.e. getting a list of successful or failed acquisitions. From our investigations it appears that it may be possible to use mass filtering as part of the MS imaging package to generate a list of locations (recognized via a file list) that pass certain criteria. While this will greatly help with the generation of a prototype workflow, it will need to be optimized via specialized software to avoid a semi-manual process.

Figure 22:
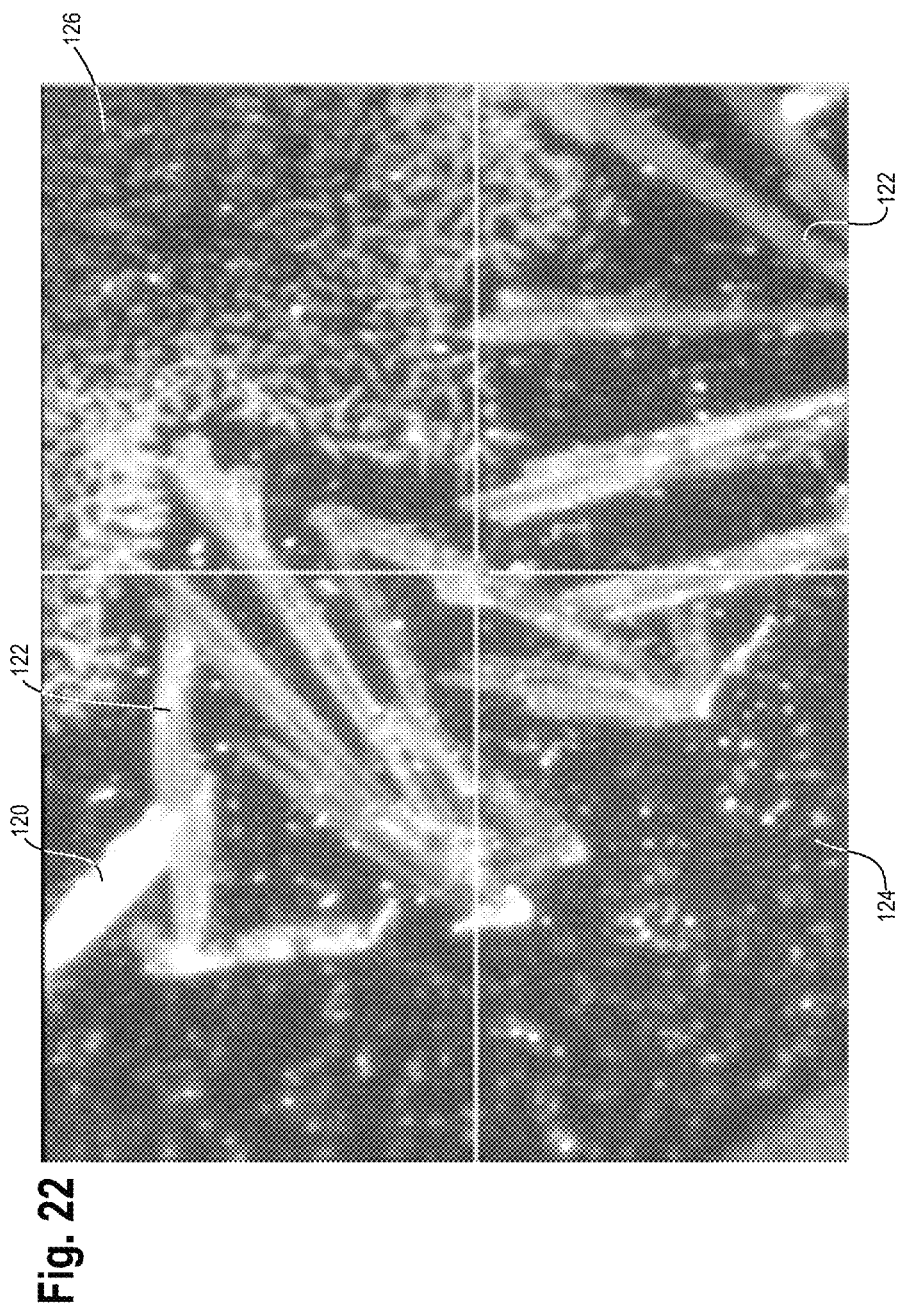
FIG. 22 is an image of a portion of a sample spot showing areas where the sample/matrix mixture does not crystallize in a spatially uniform manner.

FIG. 22 shows a region of a MALDI spot using CLCCA as a matrix, where the high yield areas consist of linear structures and areas of low yield are shown as dark areas. For these cases, where the matrix sample crystallizes very unevenly, like shown in FIG. 20, the image analysis approach seems most sensible. The image analysis identifies the relatively high yield areas (120, 122). The relatively low yield areas, such as the areas 124 on the lower left and the matrix area 126 are identified by the image analysis software and are ignored during shooting.

The image analysis software to identify high and low yield areas on a spot could take a variety of forms, and can be developed by persons skilled in the art. For example, the black and white image of the spot (FIG. 19) consists of an array of pixels, each having an 8 bit quantized value, with 0 being black (no signal) and 255 being white (saturated). The filtering can be used to identify areas of relatively high yield, such as by identifying pixels with a pixel value greater than say 100 being identified as "high yield" and pixels having a pixel value lower than 40 being identified as relatively "low yield". The scanning then proceeds to those areas of the sample spot in which the corresponding pixel has a value of 100 or more. It may also be possible to filter out spot locations in which the pixel value is 240-255 as such areas may be determined to have salt crystals or other properties that result in low yield. Referring again to FIG. 22, the pixels for the crystalline structures 120, 122 have pixel values falling in the range of 100-240 and thus would be scanned whereas the black areas 124 and 126 would not be. Morphological processing techniques could also be used to identify structures such as the crystals 120 of FIG. 22. The image analysis software could include both morphological processing and filtering to determine areas to scan. Additionally, the spot can change during the course of scanning (due to depletion of the sample) and the image processing can be run during the scanning to optimize the shooting over the course of generating 100,000 or more shots from a spot, and those locations of low sample concentration avoided during shooting.

Figure 23:
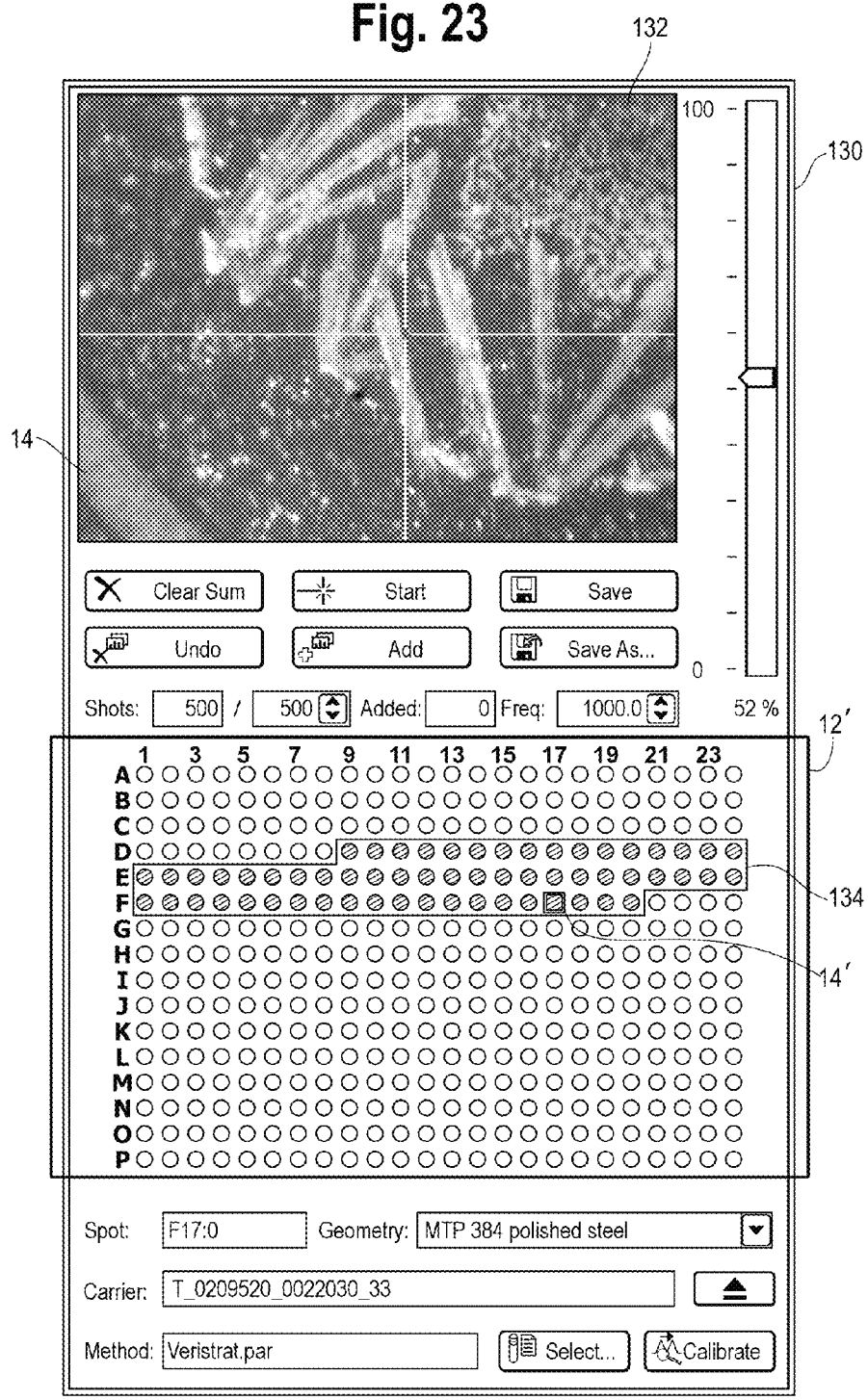
FIG. 23 is a screen shot from a MALDI-TOF instrument user interface showing an image of a portion of a spot captured by a camera in the instrument, and the selection of a group of spots for automated raster scanning of the spots.

FIG. 23 is a screen shot from a MALDI-TOF instrument showing the display of the instrument workstation 130, including an image 132 of a spot 14, in this case spot F17 of the plate. The layout of the plate is shown at 12', with the spot F17 indicated at 14'. A group of spots 134 (D9 to F20) are selected for running in an automatic mode using the image analysis method described above.

Figure 24:
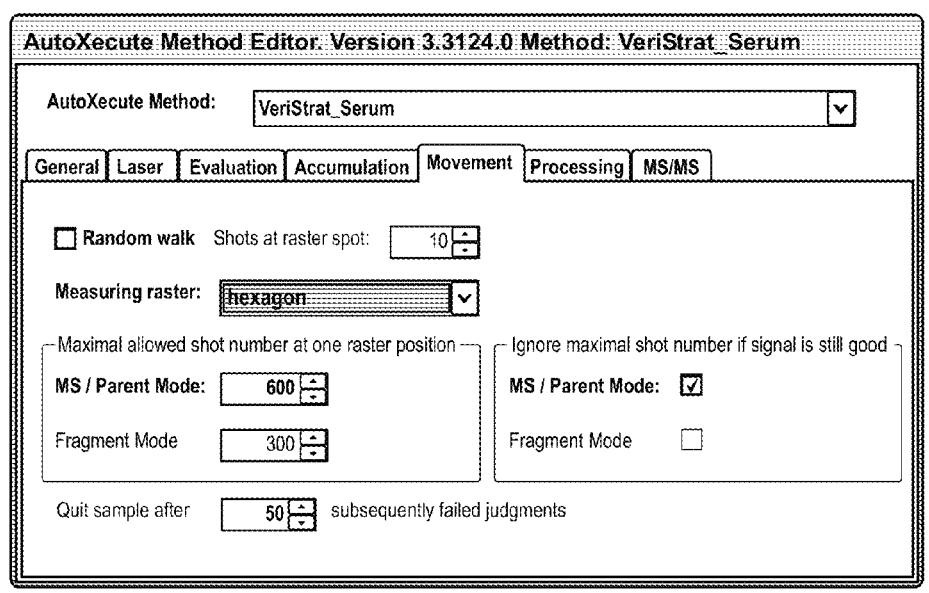
FIG. 24 is another screen shot from a MALDI-TOF instrument user interface showing tools for evaluation of spectra, accumulation of spectra, and movement of a laser across a spot for firing in different patterns.

FIG. 24 is another screen shot from the instrument. Current instruments allow the user to set evaluation regions to accept or reject transient spectra (using the Evaluation tab), set how many spectra to accumulate per spot (using the Accumulation tab) and "move" across the spot so that the laser can fire in a certain pattern (using the "Movement" tab, shown). The options include random walk or movement in pattern, e.g., hexagon or spiral. The software also allows the user to keep firing the laser and acquiring and adding to the total spectra according to such parameters until spectra from 750 shots are collected from a shot location, and then move to the next shot location. One can set the number of tries before the shot location is considered a failed spot. The image analysis methods in which likely areas of low yield are identified, and shooting in those areas avoided, helps in considerably reducing or eliminating those failed judgments.

Figure 25:
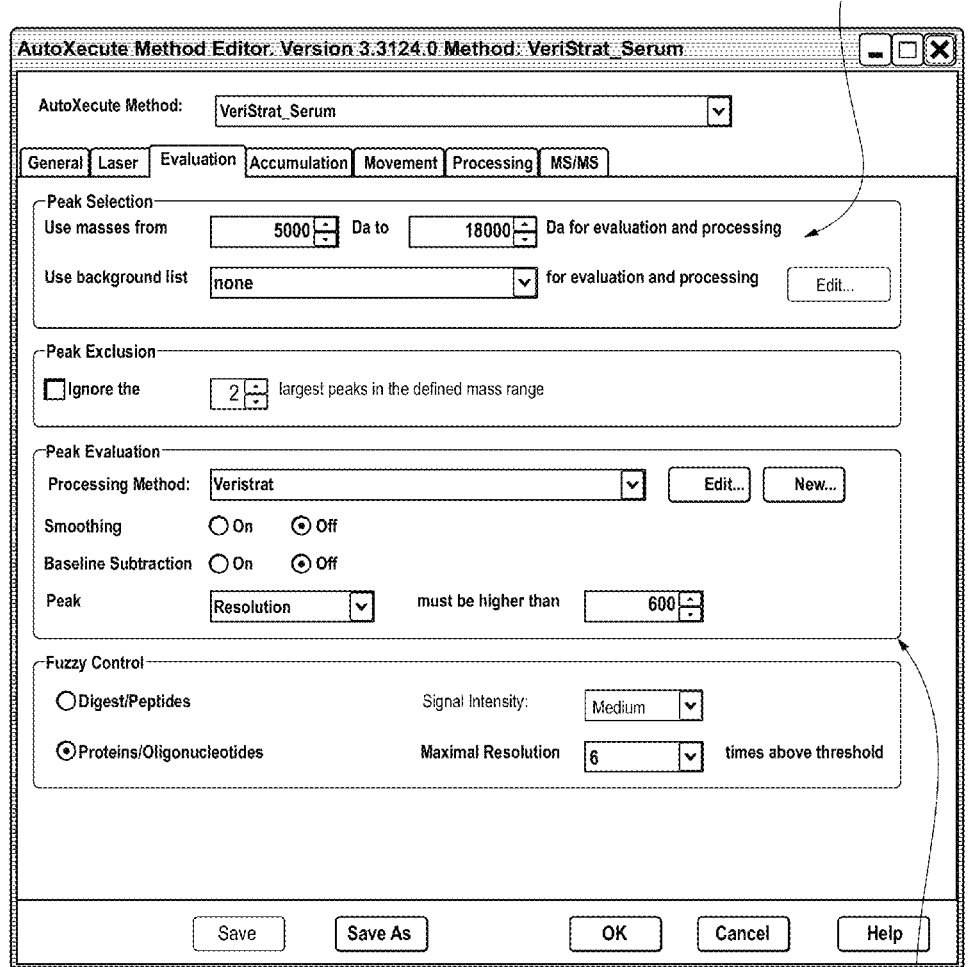
FIG. 25 is a screen shot of an evaluation page for accepting or rejecting transient spectra during data acquisition.

FIG. 25 shows an evaluation page where a mass range for accepting or rejecting transient spectra is selected, as indicated at 150. During acquisition, if a transient spectra does not have peaks in the predefined range—in this case 5,000 to 18,000 Da, that pass the threshold set (based on resolution, signal intensity or other factors), then it will be rejected. That is, the transient spectra will not be added to the sum buffer to form the location spectrum (summing the spectra from all of the shots).

Figure 26:
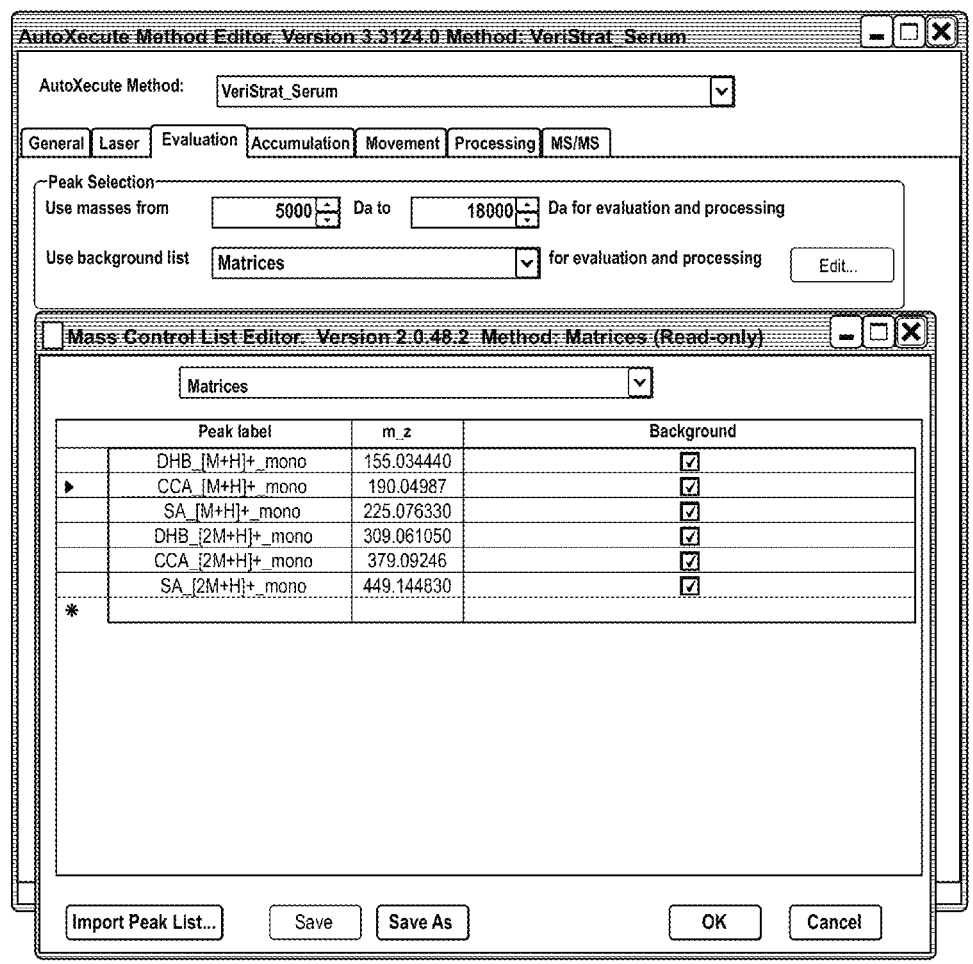
FIG. 26 is a screen shot showing exclusion lists for eliminating background peaks.

FIG. 26 shows an evaluation page where if there are specific peaks that one does not want included in the evaluation one can make an exclusion list and tag these peaks as "background peaks." The software has predefined "control lists" for matrices which define background peaks, or one can import a peak list.

Collection of Spectra from Multiple Spots

In general, one can extend the DeepMALDI technique to combining spectra from multiple spots. For example, one can obtain 500,000 shots of a sample from each of the spots A1, A2, A3, A4 and A5 on a standard MALDI plate (See FIG. 17A), and combine (sum) the resulting spectra into one overall spectrum consisting of a sum of 2,500,000 spectra (shots). A priori, there is no reason to believe that one could not combine spectra from multiple spots to reach extremely high number of shots, i.e., 100 spots×1 million shots each could give us results from 100 million shots. There may be practical limits to this procedure, e.g., the laser may fail too often.

Example of Collection of Spectra from Multiple Spots in DeepMALDI

In one example of this method, it is possible to collect spectra from 5 million shots from multiple spots of the same serum on a MALDI plate, using manually or automatically generated rasters for scanning the multiple spots using the techniques described previously. In this method, it is preferred to obtain reproducibly homogenous spots of a single sample on the MALDI plate. This can be achieved using the methods described herein.

1. Spotting Diluted Serum onto MALDI Target Plate.
Procedure:
Dilute serum 1:10 with HPLC grade water and vortex. Mix sample with matrix (20 mg/ml sinapinic acid in 50% ACN/0.1% TFA) 1:1 (v/v) in a 0.5 ml microfuge tube and vortex. Spot 4 µl of the matrix/sample mixture onto one or more spots on the MALDI target.
Thirty Six Spots (Locations) in the MALDI Plate were Used in this Example:
Tube 1: spotted on locations E13, E14, and E15 of MALDI plate (See FIG. 2A)
Tube 2: spotted on locations E16, E17, and E18
Tube 3: spotted on locations E19, E20, and E21
Tube 4: spotted on locations E22, E23, and E24
Tube 5: spotted on locations F1, F2, and F3
Tube 6: spotted on locations F4, F5, and F6
Tube 7: spotted on locations F7, F8, and F9
Tube 8: spotted on locations F10, F11, and F12
Tube 9: spotted on locations F13, F14, and F15
Tube 10: spotted on locations F16, F17, and F18
Tube 11: spotted on locations F19, F20, and F21
Tube 12: spotted on locations F22, F23, and F24
Sample spots E13 to F18 (Tubes 1-10) were directly applied after vortexing using the same pipette tip 3 times (3×4 ul of 15 ul in each tube; while the last six samples spots F19-F24 (Tubes 11 and 12) were applied as in spots E13-F18, but also pipetted up and down on plate.
Spots on MALDI plate were allowed to dry at ambient temperature by placing target plate on bench-top.
Result:
For spots E13 to F17 (which were directly applied to plate with no further on-plate mixing) the third spot from each tube was clearly more homogenous than the first two. Homogeneity was assessed visually: third spot is best, second spot is second best, first spot is the least homogenous, with the exception of E23 which is from second of three spots from tube 4, but looked more like the third spotting from each tube than the second spottings.
Sample spots F18, F19, F20, F21, F23 and F24, which were mixed by vortexing in tube and pipetted up and down on plate, were fairly similar and had the same uniform appearance as the third spot in the set from E13 to F17. F22 looked about the same as E23.

2. Acquisition of Spectrum from 5 Million Shots

Mass spectral data from approximately 312,500 shots per spot was obtained from sixteen MALDI spots after the above procedure was performed:
E15, E18, E21, E23, E24, F3, F6, F9, F12, F15, F18, F19, F20, F21, F23 and F24.
Using raster scanning files as described above, the spectra from the each of the spots was summed to produce an overall spectra of the sample obtained from approximately 5,000,000 shots.

Optimization of Sample Application to MALDI Plate (Spotting)

The sample application to the MALDI plate is optimized to provide homogenous and even distribution of the crystallized sample to each sample spot on a MALDI plate, an example of which is shown in FIG. 15. Several experiments were performed as described below to find an optimum procedure for supplying the sample mixture to a spot on the MALDI plate ("spotting"). These experiments are described in this section.

Initially, several different preparations with serum were prepared. 2 µl of matrix was spotted unless otherwise noted. Diluted sample and matrix medium were mixed in a sample prep tube unless otherwise noted. We did not spot more than 1 spot from a single prep tube unless otherwise noted as taking multiple aliquots out of the sample prep tube affects crystallization.

Ground Steel Plate experiments were conducted which produced homogeneous spots. The procedures were as follows:

1. Diluted sample 1:10 (2 µl sample+18 µl of water), then mixed 1:1 (v/v) with matrix (sinapinic acid 25 mg/ml) in 50% ACN/0.1% TFA and spotted 2 µl of matrix. This procedure did not produce good, homogeneous crystals.

2. Primed matrix tip. Pipetted 2 µl of matrix into spotting tip and let it sit for 30 seconds. Diluted sample 1:10 (2 µl sample+18 µl of water), then mixed 1:1 (v/v) with matrix (sinapinic acid 25 mg/ml) in 50% ACN/0.1% TFA. Ejected excess matrix from pipette tip. Placed pipette tip in sample matrix mixture and pipetted up and down 3 times. Spotted 2 µl of sample matrix mixture without changing the tip. This procedure formed good crystals that were homogeneous. Because this is a ground steel plate the sample matrix mixture doesn't spread out as much as on the polished steel plate. The dried crystals that are left in the pipette tip might improve crystallization by acting as a seed for further crystal formation.

3. The effect of temperature on crystallization was studied. Diluted sample 1:10 (2 µl sample+18 µl of water), then mixed 1:1 (v/v) with matrix (sinapinic acid 25 mg/ml) in 50% ACN/0.1% TFA. Place sample in 37° C. water bath for 5 minutes. Removed sample from water bath and spotted immediately. This procedure didn't produce good, homogeneous crystals.

4. Repeated experiment 2. above but spotted 4 µl of sample mixture instead of 2 µl. This procedure formed good crystals that were homogeneous. Spotting 4 µl fully covered the spot diameter and produce good crystals and data. This is the procedure currently considered optimal.

The procedures for spotting here are offered by way of example and not limitation, and variation from the disclosed methods are of course possible. For example, one may mix the matrix and sample material in the tube and let it set for several minutes before spotting. It has been noted that one gets more homogeneous crystals the more spots are made from the same tube using the same pipette tip. For example, one could spot 10 spots from the same tube using the same tip and only collect data on the last 5 or so spots; or alternatively one could discard the first five 4 μl aliquots from the tube before commencing spotting on a MALDI plate.

We have also found that following the procedure in 1 but using the same pipette tip to spot the same sample tube 10 times (2.5 μl per spot) onto a polished steel target plate yields similar results (spectral quality).

Further Considerations

Technical Reproducibility

Technical reproducibility studies can be done, e.g. to run 1,000 technical replicates in batches of 100 each day. One can study dependence on sample (spot) preparations (on or off plate), in particular to see whether there are preparation methods that yield more uniform ion-current yields, e.g. variations in sample dilution. One can also monitor how the number of high-yield locations changes from spot to spot, and how to minimize variations in this. Monitoring and logging all acquisitions and preparations at a high level of granularity is good practice.

Sample to Sample Reproducibility

Similar issues of sample to sample reproducibility can be studied with respect to sample to sample variations. New phenomena might occur: It may be that some samples are protein rich, and result in spots with more high-yield locations. It may be possible to obtain measures from some manner of sample attributes (optical density and color), or standardize sample acquisition devices (e.g., for serum) to generate more reproducible procedures. One may use a combined sample set with as heterogeneous a source as possible to attempt to cover most variations. Such a set should be obtained from studying existing sets and matching according to known sample collection and conditions, which makes strong use of existing sample databases.

Sensitivity

Observing more peaks in the spectra raises the question what abundance range we can see in this method, and what protein types are actually visible. This deals with the 'conventional wisdom' that in MALDI MS of complex samples one cannot observe lower abundance ions due to 'ion suppression', the idea that ions from more abundant proteins suppress the ion signal from less abundant proteins, therefore rendering the less abundant proteins undetectable. This idea appears to be solely based on the lack of observation of lower abundance ions. Indeed, our observation of an increase in peak content (see e.g., FIG. 16C) casts some doubt over this interpretation. Rather, it appears that one has to take seriously the (semi) quantitative nature of MALDI MS. If one agrees that protein abundance spans a wide range over many orders of magnitude, then one would expect that corresponding mass spectra would mimic this behavior by exhibiting a vast difference in peak height (or rather the area under a peak). One would not expect to observe low abundance proteins in MALDI spectra, not because they do not ionize, but rather because the amplitude of peaks corresponding to low abundance proteins should be very low. As it is common practice in mass spectrometry to focus on large peaks, and because lower abundance peaks would be orders of magnitude smaller, it is not surprising that these peaks have not been observed before. This is not to say that phenomena like ion suppression do not occur, or that ionization probability does not play a role, but to say that these phenomena do not entirely suppress peaks originating from low-abundance proteins, and that, if one looks for low abundance protein peaks in the low intensity region of spectra, they do indeed become observable. The quest for covering a significant percentage of the serum proteome can thus be viewed as a quest for extending the dynamic range of mass spectra. As with any other counting based technique the simple solution to this problem is to increase statistics by increasing the number of detected ions (per time-of-flight bin).

In order to get more confidence in this simple interpretation, which runs counter to conventional wisdom, one may wish to establish the dynamic range of mass spectra and link it to abundance of proteins. This should be done both from an analytical chemistry point of view, establishing sensitivity curves (as a function of m/z), as well as through the identification of proteins corresponding to some peaks and comparative abundance measurements of these proteins via orthogonal techniques like ELISAs.

Using Pre-Fractionated Samples

The methods of this disclosure can be used in combination with precipitation methods for fractionating a sample, e.g. NOG precipitation, de-lipidifying, and so on. The methods can also be used with other matrices like CLCCA. It is likely that these methods could also benefit greatly from the DeepMALDI approach. Our preliminary data using sample pre-fractionation indicate that one does indeed see different peaks, but the peak content was far from optimal. This might be expected as one purpose is to get rid of high abundance proteins.

In the past we attempted to use depletion and/or mass filtering to reduce the content of unwanted proteins like albumin and hemoglobin, but none of these methods led to a total removal, and remnants of these peaks were still visible. Using the DeepMALDI approach described here on depleted or mass filtered samples should yield better results, as reducing large peaks will also reduce the dynamic range necessary to see lower abundance proteins.

Obtain Sensible Choices of Spectral Acquisition Settings

In the autoExecute™ (Bruker) method, it is possible to define filtering settings in order to only collect transient spectra that pass certain criteria; in our case we want to only add those transient spectra (arising from <xx> number of shots) that have a total ion current larger than an externally defined threshold. While this does not seem possible in a simple manner, there are filter criteria in the processing method tab that might be used for similar purposes. Alternatively, there might be parameters in the peak evaluation methods that we could tune for this purpose. While this will not reduce the number of shots, it may overcome the problem of shot bias towards earlier shots, i.e. not to acquire transients consisting only of noise. The use of automated filtering operations in summing transient spectra to generate location spectra avoids the problem of bias.

Increase Spot Size

Given the limitations arising from the size of the laser illumination as well as from the minimal grid size for the pre-rastering step, it may well be that there are not enough shot locations with sufficient ion-yield on a standard spot. A simple way to address this would be to increase the spot size. The FlexImaging™ (Bruker) software would support this very easily. There are also options of rectangular spotting areas used in MS imaging application that might be suitable for this purpose. An additional benefit of using larger spots would be that one does not have to worry whether one can locate a similar number of decent shot locations and generate spectra of similar quality from spot to spot. Sample volume does not appear to present an issue. If larger spots are possible, it would reduce the logistics to deal with multiple spots for the same acquisition, which may be necessary for high numbers of shots.

Still further considerations for "DeepMALDI" methodology are described in U.S. provisional application Ser. No. 61/652,394 filed May 29, 2012 and the interested reader is directed to that document.

Yeast-Based Immunotherapy and Therapeutic Methods of the Invention

One embodiment of this disclosure is directed to the use of yeast-based immunotherapy compositions designed to stimulate therapeutic immune responses against cancer antigens expressed by a tumor cell in a patient with cancer. The method includes a step of administering a yeast-based immunotherapy composition for cancer (i.e., comprising a cancer antigen) to a subject that has a cancer expressing the cancer antigen, and who has been identified or selected as likely to benefit from administration of the composition by a test performed in accordance with any of the mass spectral predictive methods of the invention as described herein.

More specifically, in one aspect, a method of treating a cancer patient with yeast-based immunotherapy for cancer is described. The method includes the steps of: (a) conducting a test in accordance with any of the methods of predicting described herein, and if the class label for the spectra indicates the patient is likely to benefit from yeast-based immunotherapy for cancer, (b) administering the yeast-based immunotherapy for cancer. In one aspect, the patient is additionally treated with one or more additional anti-cancer therapies, either prior to, concurrently with, or after, treatment with the yeast-based immunotherapy for cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof.

In another aspect, this disclosure relates to a method of treating a cancer patient with yeast-based immunotherapy for cancer. The method includes the step of administering yeast-based immunotherapy for cancer to a cancer patient that has been selected by a test in accordance with any of the predictive methods of the invention as described herein, in which the class label for the spectra indicates the patient is likely to benefit from the yeast-based immunotherapy for cancer. In one aspect, the patient is additionally treated with one or more additional anti-cancer therapies, either prior to, concurrently with, or after, treatment with the yeast-based immunotherapy for cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof.

In yet another aspect of this disclosure, a method of treating a cancer patient with yeast-based immunotherapy for mutated Ras-positive cancer is described. This method includes the steps of: (a) conducting a test in accordance with any of the methods of predicting described above, and if the class label for the spectra indicates the patient is likely to benefit from yeast-based immunotherapy for mutated Ras-positive cancer, (b) administering the yeast-based immunotherapy for mutated Ras-positive cancer. In one aspect, the patient is additionally treated with one or more additional anti-cancer therapies, either prior to, concurrently with, or after, treatment with the yeast-based immunotherapy for mutated Ras-positive cancer. In one embodiment, the yeast-based immunotherapy for mutated Ras-positive cancer is a product in the series of yeast-based immunotherapy products known as GI-4000, or the equivalent. In one aspect of this embodiment of the invention, the mutated Ras-positive cancer can include, but is not limited to, pancreas cancer, non-small cell lung cancer (NSCLC), colorectal cancer (CRC), endometrial cancers, ovarian cancers, melanoma and multiple myeloma. In one aspect, the cancer is pancreas cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof. In one aspect, the yeast-based immunotherapy for mutated Ras-positive cancer is administered to the patient in conjunction with gemcitabine or the equivalent. In one embodiment, the patient is a pancreas cancer patient and the therapy comprises a product in the series of yeast-based immunotherapy products known as GI-4000 or the equivalent, either alone or in combination with gemcitabine. In one aspect, the cancer patient's tumor has been surgically resected prior to treatment with the yeast-based immunotherapy composition.

In yet another aspect of this disclosure, a method of treating a cancer patient with yeast-based immunotherapy for cancer is described. The method includes the step of administering a yeast-based immunotherapy for mutated Ras-positive cancer to a cancer patient selected by a test in accordance with any of the predictive methods of the invention as described herein in which the class label for the spectra indicates the patient is likely to benefit from the yeast-based immunotherapy for mutated Ras-positive cancer. In one aspect, the patient is additionally treated with one or more additional anti-cancer therapies, either prior to, concurrently with, or after, treatment with the yeast-based immunotherapy for mutated Ras-positive cancer. In one embodiment, the yeast-based immunotherapy for mutated Ras-positive cancer is a product in the series of yeast-based immunotherapy products known as GI-4000, or the equivalent. In one aspect of this embodiment of the invention, the mutated Ras-positive cancer can include, but is not limited to, pancreas cancer, non-small cell lung cancer (NSCLC), colorectal cancer (CRC), endometrial cancers, ovarian cancers, melanoma and multiple myeloma. In one aspect, the cancer is pancreas cancer. In one embodiment, the additional anti-cancer therapies include, but are not limited to, surgery (e.g., surgical resection of a tumor), chemotherapy, radiation therapy, targeted cancer therapies (e.g., small molecule drugs or monoclonal antibody therapies that specifically target molecules involved in tumor growth and progression), and palliative care, or any combination thereof. In one aspect, the yeast-based immunotherapy for mutated Ras-positive cancer is administered to the patient in conjunction with gemcitabine or the equivalent. In one embodiment, the patient is a pancreas cancer patient and the therapy comprises a product in the series of yeast-based immunotherapy products known as GI-4000 or the equivalent, either alone or in combination with gemcitabine. In one aspect, the cancer patient's tumor has been surgically resected prior to treatment with the yeast-based immunotherapy composition.

This disclosure uses of the term "yeast-based immunotherapy", which phrase may be used interchangeably with a "yeast-based immunotherapeutic composition", "yeast-based immunotherapy product", "yeast-based immunotherapy composition", "yeast-based composition", "yeast-based immunotherapeutic", "yeast-based vaccine", or derivatives of these phrases). As used herein, a yeast-based immunotherapeutic composition refers to a composition that includes a yeast vehicle component and an antigen component that targets a disease or condition in a subject (i.e., a yeast-based immunotherapeutic composition for cancer includes a yeast vehicle component and a cancer antigen component that targets the cancer in a patient). A yeast-based immunotherapeutic composition comprising a mutated Ras antigen useful in the present invention targets mutated Ras-positive tumors in a patient. This composition can be referred to as a "yeast-Ras immunotherapy composition", or a "yeast-based immunotherapeutic composition expressing Ras antigen", or "yeast-based immunotherapy for mutated Ras-positive cancer". A yeast-based immunotherapy for mutated Ras-positive cancer includes, but is not limited to the series of yeast based immunotherapy products known as "GI-4000".

In conjunction with the yeast vehicle, the cancer antigens (e.g., mutated Ras antigens) included in a yeast-based immunotherapy product are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more such cancer antigens are loaded into a yeast vehicle or are otherwise complexed with, attached to, mixed with or administered with a yeast vehicle, to form a composition useful in the present invention.

In one aspect of the invention, antigens useful in one or more yeast-based immunotherapy compositions of the invention include any cancer or tumor-associated antigen. In one aspect, the antigen includes an antigen associated with a preneoplastic or hyperplastic state. The antigen may also be associated with, or causative of cancer. Such an antigen may be a tumor-specific antigen, a tumor-associated antigen (TAA) or tissue-specific antigen, an epitope thereof, or an epitope agonist thereof. Cancer antigens include, but are not limited to, antigens from any tumor or cancer, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, leukemias, lymphomas, primary hepatic cancers, lung cancers, pancreatic cancers, gastrointestinal cancers (including colorectal cancers), renal cell carcinomas, hematopoietic neoplasias and metastatic cancers thereof.

Suitable cancer antigens include but are not limited to mutated Ras oncoprotein (see, e.g., U.S. Pat. Nos. 7,465,454 and 7,563,447), carcinoembryonic antigen (CEA) and epitopes thereof such as CAP-1, CAP-1-6D (GenBank Accession No. M29540 or Zaremba et al., 1997, *Cancer Research* 57:4570-4577), MART-1 (Kawakami et al, *J. Exp. Med.* 180:347-352, 1994), MAGE-1 (U.S. Pat. No. 5,750, 395), MAGE-3, GAGE (U.S. Pat. No. 5,648,226), GP-100 (Kawakami et al., *Proc. Nat'l Acad. Sci. USA* 91:6458-6462, 1992), MUC-1 (e.g., Jerome et al., *J. Immunol.*, 151:1654-1662 (1993)), MUC-2, normal and mutated p53 oncoproteins (Hollstein et al *Nucleic Acids Res.* 22:3551-3555, 1994), PSMA (prostate specific membrane antigen; Israeli et al., *Cancer Res.* 53:227-230, 1993), tyrosinase (Kwon et al *PNAS* 84:7473-7477, 1987), TRP-1 (gp75) (Cohen et al *Nucleic Acid Res.* 18:2807-2808, 1990; U.S. Pat. No. 5,840, 839), NY-ESO-1 (Chen et al *PNAS* 94: 1914-1918, 1997), TRP-2 (Jackson et al., *EMBO J,* 11:527-535, 1992), TAG72, KSA, CA-125, PSA (prostate specific antigen; Xue et al., *The Prostate*, 30:73-78 (1997)), HER-2/neu/c-erb/B2, (U.S. Pat. No. 5,550,214), EGFR (epidermal growth factor receptor; Harris et al., *Breast Cancer Res. Treat*, 29:1-2 (1994)), hTERT, p'73, B-RAF (B-Raf proto-oncogene serine/threonine-protein kinase; Sithanandam et al., (1990), *Oncogene* 5(12):1775-80), adenomatous polyposis coli (APC), Myc, von Hippel-Lindau protein (VHL), Rb-1, Rb-2, androgen receptor (AR), Smad4, MDR1 (also known as P-glycoprotein), Flt-3, BRCA-1 (breast cancer 1; U.S. Pat. No. 5,747, 282), BRCA-2 (breast cancer 2; U.S. Pat. No. 5,747,282)), Bcr-Abl, pax3-fkhr, ews-fli-1, Brachyury (GenBank Accession Nos. NP_003172.1 or NM_003181.2; Edwards et al., 1996, *Genome Res.* 6:226-233), HERV-H (human endogenous retrovirus H), HERV-K (human endogenous retrovirus K), TWIST (GenBank Accession Nos. NM_000474 and NP_000465), Mesothelin (Kojima et al., 1995, *J. Biol. Chem.* 270(37):21984-90; Chang and Pastan, 1996, *Proc. Natl. Acad. Sci. U.S.A.* 93(1):136-40), NGEP (New Gene Expressed in Prostate; Bera et al., 2004, *Proc. Natl. Acad. Sci. U.S.A.* 101(9):3059-3064; Cereda et al., 2010, *Cancer Immunol. Immunother.* 59(1):63-71; GenBank Accession Nos. AAT40139 or AAT40140), modifications of such antigens and tissue specific antigens, splice variants of such antigens, and/or epitope agonists of such antigens. Other cancer antigens are known in the art. Other cancer antigens may also be identified, isolated and cloned by methods known in the art such as those disclosed in U.S. Pat. No. 4,514,506. Cancer antigens may also include one or more growth factors and splice variants of each.

In one aspect of the invention, the cancer antigen is carcinoembryonic antigen (CEA), a polypeptide comprising or consisting of epitopes thereof such as CAP-1, CAP-1-6D (GenBank Accession No. M29540 or Zaremba et al., 1997, *Cancer Research* 57:4570-4577), a modified CEA, a splice variant of CEA, an epitope agonist of such CEA proteins, and/or a fusion protein comprising at least one immunogenic domain of CEA or an agonist epitope thereof. In one aspect, the CEA is a modified CEA corresponding to the modified CEA having an amino acid sequence represented by SEQ ID NO:46 in U.S. Patent Publication No. US 2007_0048860, published Mar. 1, 2007, which is encoded by a nucleic acid sequence of SEQ ID NO:45 in that publication.

In one aspect of the invention, the yeast-based immunotherapy composition targets human Brachyury. Brachyury antigens and yeast-based immunotherapy compositions targeting brachyury have been described in PCT Publication No. 2012/125998, published Sep. 20, 2012.

In one aspect of the invention, the yeast-based immunotherapy composition targets mucin-1 (MUC-1). MUC-1 antigens and yeast-based immunotherapy compositions targeting MUC-1 have been described in PCT Publication No. 2013/025972, published Feb. 21, 2013.

In one aspect of the invention, a yeast-based immunotherapy composition targets mutated Ras-positive cancers. ras is an oncogene in which several mutations are known to occur at particular positions and be associated with the development of one or more types of cancer. Therefore, a yeast-based immunotherapy product for mutated Ras-positive cancers includes at least one immunogenic domain of Ras containing an amino acid residue that is known to be mutated in certain cancers. Such cancers include, but are not limited to, pancreas cancer, NSCLC, colorectal, endometrial and ovarian cancers, as well as melanoma and multiple myeloma. In one aspect, a yeast-based immunotherapy product for mutated Ras-positive cancers contains two, three, or more immunogenic domains of Ras, wherein each domain contains one or more different Ras mutations known to occur in certain cancers, in order to cover several or all known mutations that occur in Ras proteins. For example, in one aspect of the invention, the Ras antigen used in the yeast-based immunotherapeutic composition comprises at least 5-9 contiguous amino acid residues of a wild-type Ras protein containing amino acid positions 12, 13, 59, 61, 73, 74, 75, 76, 77 and/or 78 relative to the wild-type Ras protein, wherein the amino acid residues at positions 12, 13, 59, 61, 73, 74, 75, 76, 77 and/or 78 are mutated with respect to the wild-type Ras protein. In one aspect, the cancer antigen includes: (a) a protein comprising at least from positions 4-20 or at least from positions 8-16 of a wild-type Ras protein, except that the amino acid residue at position 12 with respect to the wild-type Ras protein is mutated; (b) a protein comprising at least from positions 5-21 or at least from positions 9-17 of a wild-type Ras protein, except that the amino acid residue at position 13 with respect to the wild-type Ras protein is mutated; (c) a protein comprising at least from positions 51-67 or at least from positions 55-63 of a wild-type Ras protein, except that the amino acid residue at position 59 with respect to the wild-type Ras protein is mutated; (d) a protein comprising at least from positions 53-69 or at least from positions 57-65 of a wild-type Ras protein, except that the amino acid residue at position 61 with respect to the wild-type Ras protein is mutated; (e) a protein comprising at least from positions 65-81 or at least from positions 69-77 of a wild-type Ras protein, except that the amino acid residue at position 73 with respect to the wild-type Ras protein is mutated; (f) a protein comprising at least from positions 66-82 or at least from positions 70-78 of a wild-type Ras protein, except that the amino acid residue at position 74 with respect to the wild-type Ras protein is mutated; (g) a protein comprising at least from positions 67-83 or at least from positions 71-79 of a wild-type Ras protein, except that the amino acid residue at position 75 with respect to the wild-type Ras protein is mutated; (h) a protein comprising at least from positions 69-84 or at least from positions 73-81 of a wild-type Ras protein, except that the amino acid residue at position 77 with respect to the wild-type Ras protein is mutated; (i) a protein comprising at least from positions 70-85 or at least from positions 74-82 of a wild-type Ras protein, except that the amino acid residue at position 78 with respect to the wild-type Ras protein is mutated; and/or (j) a protein comprising at least from positions 68-84 or at least from positions 72-80 of a wild-type Ras protein, except that the amino acid residue at position 76 with respect to the wild-type Ras protein is mutated. It is noted that these positions correspond generally to K-Ras, N-Ras and H-Ras proteins, and to human and mouse sequences, as well as others, since human and mouse sequences are identical in these regions of the Ras protein and since K-Ras, H-Ras and N-Ras are identical in these regions of the Ras protein.

As used herein, the term "GI-4000" generally refers to a series of yeast-based immunotherapy compositions (TARMOGEN® products), where each yeast-based immunotherapy composition expresses one or more Ras mutations that target Ras mutations observed in human cancers. Such mutations are associated with the development of tumors. GI-4000 as used in the clinic and described in the Examples herein presently consists of a series of four yeast-based immunotherapy product versions, denoted individually as GI-4014, GI-4015, GI-4016 and GI-4020. Each version is a heat-inactivated, whole (intact) *Saccharomyces cerevisiae* yeast recombinantly expressing a fusion protein containing a unique combination of three Ras mutations (one mutation at position 12 with respect to the native Ras protein and two different mutations at position 61 with respect to the native Ras protein), collectively targeting seven of the most common Ras mutations observed in human cancers (four different position 12 mutations and 3 different position 61 mutations). In the GI-4000 clinical studies, each patient's tumor is sequenced to identify the specific Ras mutation contained in the patient's tumor and the corresponding yeast-Ras immunotherapy product containing the identified mutated protein is then administered. Each product in the GI-4000 series is manufactured and vialed separately.

More particularly, each fusion protein expressed by a yeast-based immunotherapeutic composition in the series of GI-4000 products presently used in the clinic (denoted individually as GI-4014, GI-4015, GI-4016 and GI-4020) has an amino acid sequence generally having the following overall structure, from N- to C-terminus: (1) a two amino acid N-terminal peptide sequence (M-V), (2) an amino acid sequence corresponding to positions 56-67 of Ras having a single amino acid substitution corresponding to position 61 of the native Ras protein, and (3) an amino acid sequence corresponding to positions 2-165 of Ras having two single amino acid substitutions corresponding to positions 12 and 61, respectively, of the native Ras protein. The specific combination of the three amino acid substitutions in each fusion protein distinguishes one fusion protein from the other. Other structures and organization of immunogenic domains within yeast-based immunotherapy products targeting mutated Ras-positive cancers are possible, and are described in detail in, e.g., U.S. Pat. No. 7,465,454.

The nucleotide and translated amino acid sequence for the construct encoding GI-4014 are represented by SEQ ID Nos:1 and 2, respectively. GI-4014 comprises the following Ras mutations: Q61L-G12V-Q61R. The nucleotide and translated amino acid sequence for the construct encoding GI-4015 are represented by SEQ ID Nos:3 and 4, respectively. GI-4015 comprises the following Ras mutations: Q61L-G12C-Q61R. The nucleotide and translated amino acid sequence for the construct encoding GI-4016 are represented by SEQ ID Nos:5 and 6, respectively. GI-4016 comprises the following Ras mutations: Q61L-G12D-Q61R. The nucleotide and translated amino acid sequence for the construct encoding GI-4020 are represented by SEQ ID Nos:7 and 8, respectively. GI-4020 comprises the following Ras mutations: Q61L-G12R-Q61H.

The invention also includes the use of homologues of any of the above-described Ras antigens. In one aspect, the invention includes the use of Ras antigens, having amino acid sequences that are at least 85%, 86%, 87%, 88%, 89%, 90%, 91%, 92%, 93%, 94%, 95%, 96%, 97%, 98%, or 99% identical to the amino acid sequence of any one of the Ras antigens described herein, including any of the Ras antigens referenced by a specific sequence identifier herein, over the full length of the protein or fusion protein, or with respect to a defined segment in the fusion protein or a defined protein or domain thereof (immunogenic domain or functional domain (i.e., a domain with at least one biological activity)) that forms part of the fusion protein. As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schaeffer, A. A., Zhang, J., Zhang, Z., Miller, W. &Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition useful in the invention. The yeast vehicle can therefore include, but is not limited to, a live intact (whole) yeast microorganism (i.e., a yeast cell having all its components including a cell wall), a killed (dead) or inactivated intact yeast microorganism, or derivatives of intact/whole yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation. These yeast vehicles are described in detail in, e.g., U.S. Pat. Nos. 5,830,463, 7,083, 787, and U.S. Pat. No. 7,736,642, the disclosures of which are incorporated by reference herein.

Any yeast strain can be used to produce a yeast-based immunotherapy product useful in the present invention. Genera of yeast strains that may be used in the invention include but are not limited to *Saccharomyces, Candida, Cryptococcus, Hansenula, Kluyveromyces, Pichia, Rhodotorula, Schizosaccharomyces* and *Yarrowia*. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorphs, Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*. It is to be appreciated that a number of these species include a variety of subspecies, types, subtypes, etc. that are intended to be included within the aforementioned species.

Methods for producing yeast-based immunotherapy products useful in the invention have been previously described in, e.g. U.S. Pat. Nos. 5,830,463, 7,083,787, and U.S. Pat. No. 7,736,642, the disclosures of which are incorporated herein by reference. Typically, yeast-based immunotherapy products useful in the invention have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods.

Yeast vehicles can be formulated into yeast-based immunotherapy compositions or products of the present invention, including preparations to be administered to a subject, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration. The composition should be formulated to be suitable for administration to a human subject (e.g., the manufacturing conditions should be suitable for use in humans, and any excipients or formulations used to finish the composition and/or prepare the dose of the immunotherapeutic for administration should be suitable for use in humans). In one aspect of the invention, yeast-based immunotherapeutic compositions are formulated for administration by injection of the patient or subject, such as by a parenteral route (e.g., by subcutaneous, intraperitoneal, intramuscular or intradermal injection, or another suitable parenteral route).

The therapeutic methods include the delivery (administration, immunization) of a yeast-based immunotherapeutic composition to a subject or individual. The administration process can be performed ex vivo or in vivo, but is typically performed in vivo. Administration of a yeast-based immunotherapy composition can be systemic, mucosal and/or proximal to the location of the target site (e.g., near a site of a tumor). Suitable routes of administration will be apparent to those of skill in the art, depending on the type of cancer to be prevented or treated and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., Proc. Natl. Acad. Sci. USA 189:11277-11281, 1992). In one aspect, a yeast-based immunotherapeutic composition of the invention is administered subcutaneously. In one aspect, the yeast-based immunotherapeutic composition is administered directly into a tumor milieu.

In general, a suitable single dose of a yeast-based immunotherapeutic composition is a dose that is capable of effectively providing a yeast vehicle and the cancer antigen to a given cell type, tissue, or region of the patient body in an amount effective to elicit an antigen-specific immune response against one or more cancer antigens or epitopes, when administered one or more times over a suitable time period. For example, in one embodiment, a single dose of a yeast-based immunotherapeutic useful in the present invention is from about $1\times10^5$ to about $5\times10^7$ yeast cell equivalents per kilogram body weight of the organism being administered the composition. In one aspect, a single dose of a yeast-based immunotherapeutic useful in the present invention is from about 0.1 Y.U. ($1\times10^6$ cells) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). As used herein, the term "Y.U." is a "Yeast Unit" or "yeast cell equivalent, where one Y.U.=10 million yeast cells. In one embodiment, doses include doses between 1 Y.U and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60 Y.U., 70 Y.U., or 80 Y.U. In one embodiment, the doses are administered at different sites on the individual but during the same dosing period. For example, a 40 Y.U. dose may be administered via by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose.

"Boosters" or "boosts" of yeast-based immunotherapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which a single dose is administered at least 1, 2, 3, 4, 5, 6, 7, 8, 9, 10, or more times over a time period of from weeks, to months, to years. In one embodiment, the doses are administered weekly for 1, 2, 3, 4, 5, 6, 7, 8, 9, 10 or more doses, followed by monthly doses as needed to achieve the desired therapeutic result. Additional doses can be administered even if the patient's tumor recurs, or after the patient is deemed to be in remission.

In one aspect, the individual is additionally treated with at least one other therapeutic compound or therapeutic protocol useful for the treatment of cancer (anti-cancer therapy). Additional agents, compositions or protocols (e.g., therapeutic protocols) that are useful for the treatment of cancer include, but are not limited to, chemotherapy, surgical resection of a tumor, radiation therapy, allogeneic or autologous stem cell transplantation, cytokine therapy, adoptive T cell transfer, and/or administration of a second immunotherapeutic composition (e.g., additional yeast-based immunotherapy, recombinant virus-based immunotherapy (viral vectors), cytokine therapy, immunostimulant therapy (including chemotherapy with immunostimulating properties), DNA vaccines, and other immunotherapy compositions and/or targeted cancer therapies (e.g., small molecule drugs, biologics, or monoclonal antibody therapies that specifically target molecules involved in tumor growth and progression, including, but not limited to, selective estrogen receptor modulators (SERMs), aromatase inhibitors, tyrosine kinase inhibitors, serine/threonine kinase inhibitors, histone deacetylase (HDAC) inhibitors, retinoid receptor activators, apoptosis stimulators, angiogenesis inhibitors, poly (ADP-ribose) polymerase (PARP) inhibitors, or immunostimulators).Any of these additional therapeutic agents and/or therapeutic protocols may be administered before, concurrently with, alternating with, or after the immunotherapy compositions of the invention, or at different time points. For example, when given to an individual in conjunction with chemotherapy or a targeted cancer therapy, it may be desirable to administer the yeast-based immunotherapy compositions during the "holiday" between doses of chemotherapy or targeted cancer therapy, in order to maximize the efficacy of the immunotherapy compositions. Surgical resection of a tumor may frequently precede administration of a yeast-based immunotherapy composition, but additional or primary surgery may occur during or after administration of a yeast-based immunotherapy composition.

For example, in any of the embodiments regarding therapeutic methods of the invention described herein, in one aspect, when the individual has cancer, the individual is being treated or has been treated with another therapy for cancer. Such therapy can include any of the therapeutic protocols or use of any therapeutic compound or agent described previously herein, including, but not limited to, chemotherapy, radiation therapy, targeted cancer therapy, surgical resection of a tumor, stem cell transfer, cytokine therapy, adoptive T cell transfer, and/or administration of a second immunotherapeutic composition. In the case of administration of a second immunotherapeutic composition, such compositions may include, but are not limited to, additional yeast-based immunotherapy, recombinant virus-based immunotherapy (viral vectors), immunostimulant therapy (including chemotherapy with immunostimulating properties), DNA vaccines, and other immunotherapy compositions).

As used herein, to "treat" a cancer, or any permutation thereof (e.g., "treated for cancer", etc.) generally refers to administering a yeast-based immunotherapy composition of the invention once the cancer has occurred (e.g., once the cancer has been diagnosed or detected in an individual), with at least one therapeutic goal of the treatment (as compared to in the absence of this treatment) including: reduction in tumor burden, inhibition of tumor growth, increase in recurrence free survival of the individual, increase in overall survival of the individual, delaying, inhibiting, arresting or preventing the onset or development of metastatic cancer (such as by delaying, inhibiting, arresting or preventing the onset of development of tumor migration and/or tumor invasion of tissues outside of primary cancer and/or other processes associated with metastatic progression of cancer), delaying or arresting cancer progression, improvement of immune responses against the tumor, improvement of long term memory immune responses against the tumor antigens, and/or improved general health of the individual. To "prevent" or "protect" from a cancer, or any permutation thereof (e.g., "prevention of cancer", etc.), generally refers to administering a composition of the invention before a cancer has occurred, or before a specific stage of cancer or tumor antigen expression in a cancer has occurred, with at least one goal of the treatment (as compared to in the absence of this treatment) including: preventing or delaying the onset or development of a cancer, or, should the cancer occur after the treatment, at least reducing the severity of the cancer (e.g., reducing the level of tumor growth, arresting cancer progression, improving the immune response against the cancer, inhibiting metastatic processes) or improving outcomes in the individual (e.g., improving recurrence-free survival and/or overall survival).

In the therapeutic methods of the present invention, yeast-based immunotherapy compositions and other anti-cancer therapies can be administered to any animal, including any vertebrate, and particularly to any member of the Vertebrate class, Mammalia, including, without limitation, primates, rodents, livestock and domestic pets. An "individual" is a vertebrate, such as a mammal, including without limitation a human. The term "individual" can be used interchangeably with the term "animal", "subject" or "patient".

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-12 amino acids (i.e., a peptide) and as large as: a full length protein, a multimer, a fusion protein, a chimeric protein, a whole cell, a whole microorganism, or any portions thereof (e.g., lysates of whole cells or extracts of microorganisms). In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism.

When the antigen is to be expressed in yeast, an antigen is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or is at least 25-50 amino acids in length, at least 30-50 amino acids in length, or at least 35-50 amino acids in length, or at least 40-50 amino acids in length, or at least 45-50 amino acids in length. Smaller proteins may be expressed, and considerably larger proteins (e.g., hundreds of amino acids in length or even a few thousand amino acids in length) may be expressed. In one aspect, a full-length protein, or a structural or functional domain thereof, or an immunogenic domain thereof, that is lacking one or more amino acids from the N- and/or the C-terminus may be expressed (e.g., lacking between about 1 and about 20 amino acids from the N- and/or the C-terminus). Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). For example, a "Ras antigen" is an antigen derived, designed, or produced from one or more Ras proteins such that targeting the antigen also targets the corresponding Ras protein expressed by a tumor. A "mutated Ras antigen" refers specifically to a Ras antigen that contains one or more amino acid mutations. For use in the present invention, such mutations correspond to mutations found in the Ras protein in tumors and are associated with the development of the tumor and/or the progression of the tumor.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, an immunogen contained in a yeast-based immunotherapy composition elicits a cell-mediated immune response, including a CD4+ T cell response (e.g., TH1, TH2 and/or TH17) and/or a CD8+ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is actually recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be from 8 amino acids up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

While various embodiments of the present invention have been described in detail, it is apparent that modification and adaptations from those embodiments will occur to those skilled in the art. It will be expressly understood, however, that such modifications and adaptations are within the scope of the present invention, as set forth in the appended claims.

We claim:

1. A method of predicting whether a cancer patient is likely to benefit from administration of a yeast-based immune response generating therapy for cancer, either alone or in addition to another anti-cancer therapy, comprising the steps of:
   (a) obtaining a blood-derived sample of the patient;
   (b) conducting mass-spectrometry on the sample and obtaining a mass spectrum from the sample, wherein the mass spectrometry comprises conducting MALDI-TOF mass spectrometry in which the blood-derived sample is subject to more than 20,000 laser shots;
   (c) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients and classifying the mass spectrum with a class label;
   wherein the class label predicts whether the patient is likely to benefit from the yeast-based immune response generating therapy, either alone or in addition to other anti-cancer therapies.

2. The method of claim 1, wherein the yeast-based immune response generating therapy comprises a yeast-based immunotherapy for mutated Ras-positive cancer.

3. The method of claim 2, wherein the yeast-based immunotherapy for mutated Ras-positive cancer comprises GI-4000 or the equivalent.

4. The method of claim 2, wherein the yeast-based immunotherapy for mutated Ras-positive cancer therapy is administered to the patient in conjunction with gemcitabine or the equivalent.

5. The method of claim 1, wherein the cancer patient comprises a pancreatic cancer patient.

6. The method of claim 1, wherein the training set comprises class-labeled spectra from other cancer patients who obtained benefit or did not obtain benefit from administration of the yeast-based immune response generating therapy or immunotherapy either alone or in combination with another anti-cancer therapy.

7. The method of claim 1, wherein the selected features include one or more features listed in Tables 1, 2, 3, 4, 5, or 6.

8. A method of predicting whether a cancer patient is likely to benefit from administration of a yeast-based immune response generating therapy for cancer, either alone or in addition to another anti-cancer therapy, comprising the steps of:
   (a) obtaining a blood-derived sample of the patient;
   (b) conducting mass-spectrometry on the sample and obtaining a mass spectrum from the sample;
   (c) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients and classifying the mass spectrum with a class label; wherein the predefined m/z regions are obtained from investigation of a plurality of mass spectra of blood-derived samples of cancer patients, each of the mass spectra obtained by MALDI-TOF mass spectrometry in which the blood-derived samples are subject to more than 20,000 laser shots,
   wherein the class label predicts whether the patient is likely to benefit from the yeast-based immune response generating therapy, either alone or in addition to other anti-cancer therapies.

9. The method of claim 8, wherein the yeast-based immune response generating therapy comprises a yeast-based immunotherapy for mutated Ras-positive cancer.

10. The method of claim 9, wherein the yeast-based immunotherapy for mutated Ras-positive cancer comprises GI-4000 or the equivalent.

11. The method of claim 10, wherein the yeast-based immunotherapy for mutated Ras-positive cancer therapy is administered to the patient in conjunction with gemcitabine or the equivalent.

12. The method of claim 8, wherein the cancer patient comprises a pancreatic cancer patient.

13. The method of claim 8, wherein the training set comprises class-labeled spectra from other cancer patients who obtained benefit or did not obtain benefit from administration of the yeast-based immune response generating therapy either alone or in combination with another anti-cancer therapy.

14. The method of claim 8, wherein the selected features include one or more features listed in Tables 1, 2, 3, 4, 5, or 6.

15. A system for predicting whether a cancer patient is likely to benefit from administration of a yeast-based immune response generating therapy either alone or in combination with another anti-cancer therapy, comprising, in combination:
- a mass spectrometer generating a mass spectrum from a blood-derived sample from the cancer patient, wherein the mass spectrometer comprises a MALDI-TOF mass spectrometer configured to obtain spectra by subjecting the blood-derived sample to more than 20,000 laser shots;
- a machine readable memory storing a training set of class-labeled spectra from other cancer patients, the training set including class-labeled spectra from a plurality of patients that did not benefit from the yeast-based immune response generating therapy either alone or in combination with the another anti-cancer therapy and class-labeled spectra from a plurality of patients that did benefit from the immune response generating therapy either alone or in combination with the another anti-cancer therapy; and
- a computer system configured to operate on the mass spectrum and classify the mass spectrum using the training set, producing a class label for the mass spectrum, wherein the class label predicts whether the patient is likely to benefit from administration of the yeast-based immune response generating therapy either alone or in combination with another anti-cancer agent.

16. The system of claim 15, wherein the class label predicts whether the patient is likely to benefit from administration of a yeast-based immune response generating therapy for mutated Ras-positive cancer.

17. The system of claim 16, wherein the yeast-based immune response generating therapy for mutated Ras-positive cancers comprises GI-4000 or the equivalent.

18. The system of claim 17, wherein the class label predicts whether patient is likely to benefit from administration of GI-4000 and gemcitabine to the patient.

19. The system of claim 15, wherein the cancer patient comprises a pancreatic cancer patient.

20. The system of claim 15, wherein the computer is configured to obtain integrated intensity values of features in the spectrum in m/z ranges which include one or more of the features listed in Tables 1, 2, 3, 4, 5 or 6.

21. A method of creating a classifier for predicting, in advance of treatment, whether a cancer patient is likely to benefit from a yeast-based immune response generating therapy, either alone or in combination with another anti-cancer therapy, comprising the steps of:
a) performing mass spectrometry on a multitude of patient samples obtained after treatment by the yeast-based immune response generating therapy either alone or in combination with another anti-cancer therapy and generating a corresponding set of mass spectra, wherein the mass spectrometry comprises mass spectrometry in a MALDI-TOF mass spectrometer in which the sample is subject to more than 20,000 laser shots, b) creating a training set for a classifier by separating the patients from which the samples in step a) were obtained into two groups corresponding to whether or not such patients obtained benefit from the treatment and assigning a class label to the respective spectra;
c) analyzing the spectra from the two groups to identify distinguishing features in the spectra characteristic of the patients in the two groups; and
d) testing the ability of such distinguishing features to predict patient benefit from the treatment by applying a classification algorithm using the class labeled spectra and distinguishing features identified in step c) to a test set of spectra from other patients that were administered the yeast-based immune response generating therapy, either alone or in combination with another anti-cancer therapy, and evaluating the performance of the classification algorithm.

22. The method of claim 21, wherein the distinguishing features comprise one or more features listed in Tables 1, 2, 3, 4, 5 or 6.

23. The method of claim 21, further comprising performing a partial ion current normalization of the spectra based on features in the spectra in the training set.

24. The method of claim 21, wherein the class labels are determined by investigation of clinical data for the patients in the training set.

25. A method for treating a cancer, comprising administering yeast-based immunotherapy for cancer to a cancer patient,
wherein the patient has been selected by a mass spectrometry and classification test, the test comprising the steps of:
(a) conducting mass-spectrometry on a blood-derived sample from the patient and obtaining a mass spectrum from the sample, wherein the mass spectrometry comprises conducting MALDI-TOF mass spectrometry in which the blood-derived sample is subject to more than 20,000 laser shots;
(b) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients treated with the yeast-based immunotherapy and classifying the mass spectrum with a class label;
and wherein the class label for the mass spectrum indicates that the patient is likely to benefit from the yeast-based immunotherapy for cancer.

26. The method of claim 25, wherein the patient is additionally treated with one or more additional anti-cancer therapies, either prior to, concurrently with, or after, treatment with the yeast-based immunotherapy for cancer.

27. The method of claim 26, wherein the additional anti-cancer therapies are selected from: surgery, chemotherapy, radiation therapy, targeted cancer therapy, palliative care, or any combination thereof.

28. The method of claim 26, wherein the cancer patient's tumor has been surgically resected prior to treatment with the yeast-based immunotherapy.

29. The method of claim 25, wherein the yeast-based immunotherapy is a whole, heat-inactivated recombinant yeast that has expressed one or more cancer antigens from the patient's cancer.

30. The method of claim 29, wherein the yeast is from *Saccharomyces cerevisiae*.

31. The method of claim 25, wherein the patient has mutated Ras-positive cancer and wherein the patient is administered a yeast-based immunotherapy for mutated Ras-positive cancer.

32. The method of claim 31, wherein the patient is additionally treated with one or more additional anti-cancer therapies, either prior to, concurrently with, or after, treatment with the yeast-based immunotherapy for mutated Ras-positive cancer.

33. The method of claim 32, wherein the additional anti-cancer therapies are selected from: surgery, chemotherapy, radiation therapy, targeted cancer therapy, palliative care, or any combination thereof.

34. The method of claim 31, wherein the mutated Ras-positive cancer is selected from: pancreas cancer, non-small cell lung cancer (NSCLC), colorectal cancer (CRC), endometrial cancers, ovarian cancers, melanoma or multiple myeloma.

35. The method of claim 31, wherein the mutated Ras-positive cancer is pancreas cancer.

36. The method of claim 31, wherein the yeast-based immunotherapy for mutated Ras-positive cancer is a whole, heat-inactivated recombinant yeast that has expressed a mutated Ras antigen.

37. The method of claim 36, wherein the yeast-based immunotherapy for mutated Ras-positive cancer is a product in the GI-4000 series of yeast-based immunotherapy products, or the equivalent.

38. The method of claim 37, wherein the product is selected from GI-4014, GI-4015, GI-4016 or GI-4020.

39. The method of claim 25, wherein the yeast-based immunotherapy is administered in conjunction with gemcitabine or the equivalent.

40. The method of claim 25, wherein the training set comprises class-labeled spectra from other cancer patients who obtained benefit or did not obtain benefit from administration of the yeast-based immunotherapy either alone or in combination with another anti-cancer therapy.

41. The method of claim 25, wherein the selected features include one or more features listed in Tables 1, 2, 3, 4, 5 or 6.

42. A method for treating a cancer, comprising administering yeast-based immunotherapy for cancer to a cancer patient,
wherein the patient has been selected by a mass spectrometry and classification test, the test comprising the steps of:
(a) conducting mass-spectrometry on a blood-derived sample from the patient and obtaining a mass spectrum from the sample;
(b) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients treated with the yeast-based immunotherapy and classifying the mass spectrum with a class label, wherein the predefined m/z regions are obtained from investigation of a plurality of mass spectra of cancer patients obtained by MALDI-TOF mass spectrometry in which blood-derived samples of such cancer patients are subject to more than 20,000 laser shots,
and wherein the class label for the mass spectrum indicates that the patient is likely to benefit from the yeast-based immunotherapy for cancer.

43. The method of claim 42, wherein the patient is additionally treated with one or more additional anti-cancer therapies, either prior to, concurrently with, or after, treatment with the yeast-based immunotherapy for cancer.

44. The method of claim 43, wherein the additional anti-cancer therapies are selected from: surgery, chemotherapy, radiation therapy, targeted cancer therapy, palliative care, or any combination thereof.

45. The method of claim 42, wherein the yeast-based immunotherapy is a whole, heat-inactivated recombinant yeast that has expressed one or more cancer antigens from the patient's cancer.

46. The method of claim 45, wherein the yeast is from *Saccharomyces cerevisiae*.

47. The method of claim 42, wherein the patient has mutated Ras-positive cancer and wherein the patient is administered a yeast-based immunotherapy for mutated Ras-positive cancer.

48. The method of claim 47, wherein the patient is additionally treated with one or more additional anti-cancer therapies, either prior to, concurrently with, or after, treatment with the yeast-based immunotherapy for mutated Ras-positive cancer.

49. The method of claim 48, wherein the additional anti-cancer therapies are selected from: surgery, chemotherapy, radiation therapy, targeted cancer therapy, palliative care, or any combination thereof.

50. The method of claim 48, wherein the yeast-based immunotherapy is administered in conjunction with gemcitabine or the equivalent.

51. The method of claim 48, wherein the cancer patient's tumor has been surgically resected prior to treatment with the yeast-based immunotherapy.

52. The method of claim 47, wherein the mutated Ras-positive cancer is selected from: pancreas cancer, non-small cell lung cancer (NSCLC), colorectal cancer (CRC), endometrial cancers, ovarian cancers, melanoma or multiple myeloma.

53. The method of claim 47, wherein the mutated Ras-positive cancer is pancreas cancer.

54. The method of claim 47, wherein the yeast-based immunotherapy for mutated Ras-positive cancer is a whole, heat-inactivated recombinant yeast that has expressed a mutated Ras antigen.

55. The method of claim 47, wherein the yeast-based immunotherapy for mutated Ras-positive cancer is a product in the GI-4000 series of yeast-based immunotherapy products, or the equivalent.

56. The method of claim 55, wherein the product is selected from GI-4014, GI-4015, GI-4016 or GI-4020.

57. The method of claim 42, wherein the training set comprises class-labeled spectra from other cancer patients who obtained benefit or did not obtain benefit from administration of the yeast-based immunotherapy either alone or in combination with another anti-cancer therapy.

58. The method of claim 42, wherein the selected features include one or more features listed in Tables 1, 2, 3, 4, 5 or 6.

59. A method for treating a cancer with yeast-based immunotherapy, comprising:
a) conducting mass-spectrometry on a blood-derived sample from a cancer patient and obtaining a mass spectrum from the sample, wherein the mass spectrometry comprises conducting MALDI-TOF multi-shot mass spectrometry in which the blood-derived sample is subject to more than 20,000 laser shots, b) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients treated with the yeast-based immunotherapy and classifying the mass spectrum with a class label; and
c) administering the yeast-based immunotherapy for cancer to the cancer patient when the class label for the mass spectrum indicates that the patient is likely to benefit from the yeast-based immunotherapy for cancer.

60. The method of claim 59, wherein the patient is additionally treated with one or more additional anti-cancer therapies, either prior to, concurrently with, or after, treatment with the yeast-based immunotherapy for cancer.

61. The method of claim 59, wherein the yeast-based immunotherapy is a whole, heat-inactivated recombinant yeast from *Saccharomyces cerevisiae* that has expressed one or more cancer antigens from the patient's cancer.

62. The method of claim 59, wherein the patient has mutated Ras-positive cancer and wherein the patient is administered a yeast-based immunotherapy for mutated Ras-positive cancer.

63. The method of claim 62, wherein the yeast-based immunotherapy for mutated Ras-positive cancer is selected from GI-4014, GI-4015, GI-4016 or GI-4020.

64. The method of claim 59, wherein the training set comprises class-labeled spectra from other cancer patients who obtained benefit or did not obtain benefit from administration of the yeast-based immunotherapy either alone or in combination with another anti-cancer therapy.

65. The method of claim 59, wherein the selected features include one or more features listed in Tables 1, 2, 3, 4, 5 or 6.

66. A method for treating a cancer with yeast-based immunotherapy, comprising:
a) conducting mass-spectrometry on a blood-derived sample from a cancer patient and obtaining a mass spectrum from the sample;
b) in a programmed computer, performing one or more predefined pre-processing steps on the mass spectrum, obtaining integrated intensity values of selected features in the mass spectrum over predefined m/z ranges after the pre-processing steps are performed, and comparing the integrated intensity values with a training set comprising class-labeled spectra from other cancer patients treated with the yeast-based immunotherapy and classifying the mass spectrum with a class label;
wherein the predefined m/z regions are obtained from investigation of a plurality of mass spectra of cancer patients obtained by multi-shot mass spectrometry in which blood-derived samples of such cancer patients are subject to more than 20,000 laser shots, and
c) administering the yeast-based immunotherapy for cancer to the cancer patient when the class label for the mass spectrum indicates that the patient is likely to benefit from the yeast-based immunotherapy for cancer.

67. The method of claim 66, wherein the patient is additionally treated with one or more additional anti-cancer therapies, either prior to, concurrently with, or after, treatment with the yeast-based immunotherapy for cancer.

68. The method of claim 66, wherein the yeast-based immunotherapy is a whole, heat-inactivated recombinant yeast from *Saccharomyces cerevisiae* that has expressed one or more cancer antigens from the patient's cancer.

69. The method of claim 66, wherein the patient has mutated Ras-positive cancer and wherein the patient is administered a yeast-based immunotherapy for mutated Ras-positive cancer.

70. The method of claim 69, wherein the yeast-based immunotherapy for mutated Ras-positive cancer is selected from GI-4014, GI-4015, GI-4016 or GI-4020.

71. The method of claim 66, wherein the training set comprises class-labeled spectra from other cancer patients who obtained benefit or did not obtain benefit from administration of the yeast based immunotherapy either alone or in combination with another anti-cancer therapy.

72. The method of claim 66, wherein the selected features include one or more features listed in Tables 1, 2, 3, 4, 5 or 6.

* * * * *

```
                              SEQUENCE LISTING

<160> NUMBER OF SEQ ID NOS: 8

<210> SEQ ID NO 1
<211> LENGTH: 537
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(537)

<400> SEQUENCE: 1 atg gtc ctc gac aca gca ggt ttg gag gag tac agt gca atg act gag        48
Met Val Leu Asp Thr Ala Gly Leu Glu Glu Tyr Ser Ala Met Thr Glu
1               5                  10                  15 tat aaa ctt gtg gtg gtt gga gct gtt ggc gta ggc aag agc gcc ttg        96
Tyr Lys Leu Val Val Val Gly Ala Val Gly Val Gly Lys Ser Ala Leu
                20                  25                  30 acg ata cag cta att cag aat cac ttt gtg gat gag tac gac cct acg       144
Thr Ile Gln Leu Ile Gln Asn His Phe Val Asp Glu Tyr Asp Pro Thr
            35                  40                  45 ata gag gac tcc tac agg aaa caa gta gta att gat gga gaa acc tgt       192
Ile Glu Asp Ser Tyr Arg Lys Gln Val Val Ile Asp Gly Glu Thr Cys
        50                  55                  60 ctc ttg gat att ctc gac aca gca ggt cga gag gag tac agt gca atg       240
Leu Leu Asp Ile Leu Asp Thr Ala Gly Arg Glu Glu Tyr Ser Ala Met
65                  70                  75                  80 agg gac cag tac atg aga act ggg gag ggc ttt ctt tgt gta ttt gcc       288
Arg Asp Gln Tyr Met Arg Thr Gly Glu Gly Phe Leu Cys Val Phe Ala
                85                  90                  95 ata aat aat act aaa tca ttt gaa gat att cac cat tat aga gaa caa       336
Ile Asn Asn Thr Lys Ser Phe Glu Asp Ile His His Tyr Arg Glu Gln
                100                 105                 110 att aaa aga gta aag gac tct gaa gat gtg cct atg gtc ctg gta ggg       384
Ile Lys Arg Val Lys Asp Ser Glu Asp Val Pro Met Val Leu Val Gly
            115                 120                 125 aat aag tgt gat ttg cct tct aga aca gta gac acg aaa cag gct cag       432
Asn Lys Cys Asp Leu Pro Ser Arg Thr Val Asp Thr Lys Gln Ala Gln
        130                 135                 140 gag tta gca agg agt tac ggg att ccg ttc att gag acc tca gca aag       480
Glu Leu Ala Arg Ser Tyr Gly Ile Pro Phe Ile Glu Thr Ser Ala Lys
145                 150                 155                 160 aca aga cag ggt gtt gac gat gcc ttc tat aca tta gtc cga gaa att       528
Thr Arg Gln Gly Val Asp Asp Ala Phe Tyr Thr Leu Val Arg Glu Ile
                165                 170                 175 cga aaa tag                                                            537
Arg Lys <210> SEQ ID NO 2
<211> LENGTH: 178
<212> TYPE: PRT
<213> ORGANISM: Artificial
<220> FEATURE:
<223> OTHER INFORMATION: Synthetic Construct

<400> SEQUENCE: 2

Met Val Leu Asp Thr Ala Gly Leu Glu Glu Tyr Ser Ala Met Thr Glu
```

```
  1               5                  10                 15
Tyr Lys Leu Val Val Val Gly Ala Val Gly Val Gly Lys Ser Ala Leu
                20                 25                 30

Thr Ile Gln Leu Ile Gln Asn His Phe Val Asp Glu Tyr Asp Pro Thr
                35                 40                 45

Ile Glu Asp Ser Tyr Arg Lys Gln Val Val Ile Asp Gly Glu Thr Cys
 50                 55                 60

Leu Leu Asp Ile Leu Asp Thr Ala Gly Arg Glu Glu Tyr Ser Ala Met
 65                 70                 75                 80

Arg Asp Gln Tyr Met Arg Thr Gly Glu Gly Phe Leu Cys Val Phe Ala
                85                 90                 95

Ile Asn Asn Thr Lys Ser Phe Glu Asp Ile His His Tyr Arg Glu Gln
                100                105                110

Ile Lys Arg Val Lys Asp Ser Glu Asp Val Pro Met Val Leu Val Gly
                115                120                125

Asn Lys Cys Asp Leu Pro Ser Arg Thr Val Asp Thr Lys Gln Ala Gln
130                 135                140

Glu Leu Ala Arg Ser Tyr Gly Ile Pro Phe Ile Glu Thr Ser Ala Lys
145                 150                155                160

Thr Arg Gln Gly Val Asp Asp Ala Phe Tyr Thr Leu Val Arg Glu Ile
                165                170                175

Arg Lys

<210> SEQ ID NO 3
<211> LENGTH: 537
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(537)

<400> SEQUENCE: 3 atg gtc ctc gac aca gca ggt ttg gag gag tac agt gca atg act gag    48
Met Val Leu Asp Thr Ala Gly Leu Glu Glu Tyr Ser Ala Met Thr Glu
 1               5                  10                 15 tat aaa ctt gtg gtg gtt gga gct tgt ggc gta ggc aag agc gcc ttg    96
Tyr Lys Leu Val Val Val Gly Ala Cys Gly Val Gly Lys Ser Ala Leu
                20                 25                 30 acg ata cag cta att cag aat cac ttt gtg gat gag tac gac cct acg   144
Thr Ile Gln Leu Ile Gln Asn His Phe Val Asp Glu Tyr Asp Pro Thr
                35                 40                 45 ata gag gac tcc tac agg aaa caa gta gta att gat gga gaa acc tgt   192
Ile Glu Asp Ser Tyr Arg Lys Gln Val Val Ile Asp Gly Glu Thr Cys
 50                 55                 60 ctc ttg gat att ctc gac aca gca ggt cga gag gag tac agt gca atg   240
Leu Leu Asp Ile Leu Asp Thr Ala Gly Arg Glu Glu Tyr Ser Ala Met
 65                 70                 75                 80 agg gac cag tac atg aga act ggg gag ggc ttc ctt tgt gta ttt gcc   288
Arg Asp Gln Tyr Met Arg Thr Gly Glu Gly Phe Leu Cys Val Phe Ala
                85                 90                 95 ata aat aat act aaa tca ttt gaa gat att cac cat tat aga gaa caa   336
Ile Asn Asn Thr Lys Ser Phe Glu Asp Ile His His Tyr Arg Glu Gln
                100                105                110 att aaa aga gta aag gac tct gaa gat gtg cct atg gtc ctg gta ggg   384
Ile Lys Arg Val Lys Asp Ser Glu Asp Val Pro Met Val Leu Val Gly
                115                120                125
```

```
aat aag tgt gat ttg cct tct aga aca gta gac acg aaa cag gct cag        432
Asn Lys Cys Asp Leu Pro Ser Arg Thr Val Asp Thr Lys Gln Ala Gln
        130                 135                 140 gag tta gca agg agt tac ggg att ccg ttc att gag acc tca gca aag        480
Glu Leu Ala Arg Ser Tyr Gly Ile Pro Phe Ile Glu Thr Ser Ala Lys
145                 150                 155                 160 aca aga cag ggt gtt gac gat gcc ttc tat aca tta gtc cga gaa att        528
Thr Arg Gln Gly Val Asp Asp Ala Phe Tyr Thr Leu Val Arg Glu Ile
                165                 170                 175 cga aaa tag                                                            537
Arg Lys <210> SEQ ID NO 4
<211> LENGTH: 178
<212> TYPE: PRT
<213> ORGANISM: Artificial
<220> FEATURE:
<223> OTHER INFORMATION: Synthetic Construct

<400> SEQUENCE: 4

Met Val Leu Asp Thr Ala Gly Leu Glu Glu Tyr Ser Ala Met Thr Glu
1               5                   10                  15

Tyr Lys Leu Val Val Gly Ala Cys Gly Val Gly Lys Ser Ala Leu
            20                  25                  30

Thr Ile Gln Leu Ile Gln Asn His Phe Val Asp Glu Tyr Asp Pro Thr
        35                  40                  45

Ile Glu Asp Ser Tyr Arg Lys Gln Val Val Ile Asp Gly Glu Thr Cys
    50                  55                  60

Leu Leu Asp Ile Leu Asp Thr Ala Gly Arg Glu Glu Tyr Ser Ala Met
65                  70                  75                  80

Arg Asp Gln Tyr Met Arg Thr Gly Glu Gly Phe Leu Cys Val Phe Ala
                85                  90                  95

Ile Asn Asn Thr Lys Ser Phe Glu Asp Ile His His Tyr Arg Glu Gln
            100                 105                 110

Ile Lys Arg Val Lys Asp Ser Glu Asp Val Pro Met Val Leu Val Gly
        115                 120                 125

Asn Lys Cys Asp Leu Pro Ser Arg Thr Val Asp Thr Lys Gln Ala Gln
    130                 135                 140

Glu Leu Ala Arg Ser Tyr Gly Ile Pro Phe Ile Glu Thr Ser Ala Lys
145                 150                 155                 160

Thr Arg Gln Gly Val Asp Asp Ala Phe Tyr Thr Leu Val Arg Glu Ile
                165                 170                 175

Arg Lys

<210> SEQ ID NO 5
<211> LENGTH: 537
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(537)

<400> SEQUENCE: 5 atg gtc ctc gac aca gca ggt ttg gag gag tac agt gca atg act gag         48
Met Val Leu Asp Thr Ala Gly Leu Glu Glu Tyr Ser Ala Met Thr Glu
1               5                   10                  15 tat aaa ctt gtg gtg gtt gga gct gat ggc gta ggc aag agc gcc ttg         96
Tyr Lys Leu Val Val Val Gly Ala Asp Gly Val Gly Lys Ser Ala Leu
```

```
                    20                  25                  30
acg ata cag cta att cag aat cac ttt gtg gat gag tac gac cct acg    144
Thr Ile Gln Leu Ile Gln Asn His Phe Val Asp Glu Tyr Asp Pro Thr
            35                  40                  45 ata gag gac tcc tac agg aaa caa gta gta att gat gga gaa acc tgt    192
Ile Glu Asp Ser Tyr Arg Lys Gln Val Val Ile Asp Gly Glu Thr Cys
 50                  55                  60 ctc ttg gat att ctc gac aca gca ggt cga gag gag tac agt gca atg    240
Leu Leu Asp Ile Leu Asp Thr Ala Gly Arg Glu Glu Tyr Ser Ala Met
 65                  70                  75                  80 agg gac cag tac atg aga act ggg gag ggc ttt ctt tgt gta ttt gcc    288
Arg Asp Gln Tyr Met Arg Thr Gly Glu Gly Phe Leu Cys Val Phe Ala
                85                  90                  95 ata aat aat act aaa tca ttt gaa gat att cac cat tat aga gaa caa    336
Ile Asn Asn Thr Lys Ser Phe Glu Asp Ile His His Tyr Arg Glu Gln
            100                 105                 110 att aaa aga gta aag gac tct gaa gat gtg cct atg gtc ctg gta ggg    384
Ile Lys Arg Val Lys Asp Ser Glu Asp Val Pro Met Val Leu Val Gly
        115                 120                 125 aat aag tgt gat ttg cct tct aga aca gta gac acg aaa cag gct cag    432
Asn Lys Cys Asp Leu Pro Ser Arg Thr Val Asp Thr Lys Gln Ala Gln
130                 135                 140 gag tta gca agg agt tac ggg att ccg ttc att gag acc tca gca aag    480
Glu Leu Ala Arg Ser Tyr Gly Ile Pro Phe Ile Glu Thr Ser Ala Lys
145                 150                 155                 160 aca aga cag ggt gtt gac gat gcc ttc tat aca tta gtc cga gaa att    528
Thr Arg Gln Gly Val Asp Asp Ala Phe Tyr Thr Leu Val Arg Glu Ile
                165                 170                 175 cga aaa tag                                                        537
Arg Lys

<210> SEQ ID NO 6
<211> LENGTH: 178
<212> TYPE: PRT
<213> ORGANISM: Artificial
<220> FEATURE:
<223> OTHER INFORMATION: Synthetic Construct

<400> SEQUENCE: 6

Met Val Leu Asp Thr Ala Gly Leu Glu Glu Tyr Ser Ala Met Thr Glu
1               5                   10                  15

Tyr Lys Leu Val Val Gly Ala Asp Gly Val Gly Lys Ser Ala Leu
                20                  25                  30

Thr Ile Gln Leu Ile Gln Asn His Phe Val Asp Glu Tyr Asp Pro Thr
            35                  40                  45

Ile Glu Asp Ser Tyr Arg Lys Gln Val Val Ile Asp Gly Glu Thr Cys
 50                  55                  60

Leu Leu Asp Ile Leu Asp Thr Ala Gly Arg Glu Glu Tyr Ser Ala Met
 65                  70                  75                  80

Arg Asp Gln Tyr Met Arg Thr Gly Glu Gly Phe Leu Cys Val Phe Ala
                85                  90                  95

Ile Asn Asn Thr Lys Ser Phe Glu Asp Ile His His Tyr Arg Glu Gln
            100                 105                 110

Ile Lys Arg Val Lys Asp Ser Glu Asp Val Pro Met Val Leu Val Gly
        115                 120                 125

Asn Lys Cys Asp Leu Pro Ser Arg Thr Val Asp Thr Lys Gln Ala Gln
130                 135                 140

Glu Leu Ala Arg Ser Tyr Gly Ile Pro Phe Ile Glu Thr Ser Ala Lys
```

145                 150                 155                 160
Thr Arg Gln Gly Val Asp Asp Ala Phe Tyr Thr Leu Val Arg Glu Ile
                165                 170                 175
Arg Lys

<210> SEQ ID NO 7
<211> LENGTH: 537
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(537)

<400> SEQUENCE: 7

| atg | gtc | ctc | gac | aca | gca | ggt | ttg | gag | gag | tac | agt | gca | atg | act | gag | 48 |
| Met | Val | Leu | Asp | Thr | Ala | Gly | Leu | Glu | Glu | Tyr | Ser | Ala | Met | Thr | Glu |  |
| 1 |  |  |  | 5 |  |  |  |  | 10 |  |  |  |  | 15 |  |  |

| tat | aaa | ctt | gtg | gtg | gtt | gga | gct | cgt | ggc | gta | ggc | aag | agc | gcc | ttg | 96 |
| Tyr | Lys | Leu | Val | Val | Val | Gly | Ala | Arg | Gly | Val | Gly | Lys | Ser | Ala | Leu |  |
|  |  |  |  | 20 |  |  |  |  | 25 |  |  |  |  | 30 |  |  |

| acg | ata | cag | cta | att | cag | aat | cac | ttt | gtg | gat | gag | tac | gac | cct | acg | 144 |
| Thr | Ile | Gln | Leu | Ile | Gln | Asn | His | Phe | Val | Asp | Glu | Tyr | Asp | Pro | Thr |  |
|  |  |  | 35 |  |  |  |  | 40 |  |  |  |  | 45 |  |  |  |

| ata | gag | gac | tcc | tac | agg | aaa | caa | gta | gta | att | gat | gga | gaa | acc | tgt | 192 |
| Ile | Glu | Asp | Ser | Tyr | Arg | Lys | Gln | Val | Val | Ile | Asp | Gly | Glu | Thr | Cys |  |
|  | 50 |  |  |  |  | 55 |  |  |  |  | 60 |  |  |  |  |  |

| ctc | ttg | gat | att | ctc | gac | aca | gca | ggt | cac | gag | gag | tac | agt | gca | atg | 240 |
| Leu | Leu | Asp | Ile | Leu | Asp | Thr | Ala | Gly | His | Glu | Glu | Tyr | Ser | Ala | Met |  |
| 65 |  |  |  |  | 70 |  |  |  |  | 75 |  |  |  |  | 80 |  |

| agg | gac | cag | tac | atg | aga | act | ggg | gag | ggc | ttt | ctt | tgt | gta | ttt | gcc | 288 |
| Arg | Asp | Gln | Tyr | Met | Arg | Thr | Gly | Glu | Gly | Phe | Leu | Cys | Val | Phe | Ala |  |
|  |  |  |  | 85 |  |  |  |  | 90 |  |  |  |  | 95 |  |  |

| ata | aat | aat | act | aaa | tca | ttt | gaa | gat | att | cac | cat | tat | aga | gaa | caa | 336 |
| Ile | Asn | Asn | Thr | Lys | Ser | Phe | Glu | Asp | Ile | His | His | Tyr | Arg | Glu | Gln |  |
|  |  |  | 100 |  |  |  |  | 105 |  |  |  |  | 110 |  |  |  |

| att | aaa | aga | gta | aag | gac | tct | gaa | gat | gtg | cct | atg | gtc | ctg | gta | ggg | 384 |
| Ile | Lys | Arg | Val | Lys | Asp | Ser | Glu | Asp | Val | Pro | Met | Val | Leu | Val | Gly |  |
|  |  | 115 |  |  |  |  | 120 |  |  |  |  | 125 |  |  |  |  |

| aat | aag | tgt | gat | ttg | cct | tct | aga | aca | gta | gac | acg | aaa | cag | gct | cag | 432 |
| Asn | Lys | Cys | Asp | Leu | Pro | Ser | Arg | Thr | Val | Asp | Thr | Lys | Gln | Ala | Gln |  |
| 130 |  |  |  |  | 135 |  |  |  |  | 140 |  |  |  |  |  |  |

| gag | tta | gca | agg | agt | tac | ggg | att | ccg | ttc | att | gag | acc | tca | gca | aag | 480 |
| Glu | Leu | Ala | Arg | Ser | Tyr | Gly | Ile | Pro | Phe | Ile | Glu | Thr | Ser | Ala | Lys |  |
| 145 |  |  |  | 150 |  |  |  |  | 155 |  |  |  |  | 160 |  |  |

| aca | aga | cag | ggt | gtt | gac | gat | gcc | ttc | tat | aca | tta | gtc | cga | gaa | att | 528 |
| Thr | Arg | Gln | Gly | Val | Asp | Asp | Ala | Phe | Tyr | Thr | Leu | Val | Arg | Glu | Ile |  |
|  |  |  | 165 |  |  |  |  | 170 |  |  |  |  | 175 |  |  |  |

| cga | aaa | tag |  |  |  |  |  |  |  |  |  |  |  |  |  | 537 |
| Arg | Lys |  |  |  |  |  |  |  |  |  |  |  |  |  |  |  |

<210> SEQ ID NO 8
<211> LENGTH: 178
<212> TYPE: PRT
<213> ORGANISM: Artificial
<220> FEATURE:
<223> OTHER INFORMATION: Synthetic Construct

<400> SEQUENCE: 8

Met Val Leu Asp Thr Ala Gly Leu Glu Glu Tyr Ser Ala Met Thr Glu
1               5                   10                  15

-continued

```
Tyr Lys Leu Val Val Val Gly Ala Arg Gly Val Gly Lys Ser Ala Leu
            20              25              30

Thr Ile Gln Leu Ile Gln Asn His Phe Val Asp Glu Tyr Asp Pro Thr
            35              40              45

Ile Glu Asp Ser Tyr Arg Lys Gln Val Val Ile Asp Gly Glu Thr Cys
 50                  55                  60

Leu Leu Asp Ile Leu Asp Thr Ala Gly His Glu Glu Tyr Ser Ala Met
 65              70                  75              80

Arg Asp Gln Tyr Met Arg Thr Gly Glu Gly Phe Leu Cys Val Phe Ala
                85              90                  95

Ile Asn Asn Thr Lys Ser Phe Glu Asp Ile His His Tyr Arg Glu Gln
                100             105             110

Ile Lys Arg Val Lys Asp Ser Glu Asp Val Pro Met Val Leu Val Gly
            115             120             125

Asn Lys Cys Asp Leu Pro Ser Arg Thr Val Asp Thr Lys Gln Ala Gln
    130             135             140

Glu Leu Ala Arg Ser Tyr Gly Ile Pro Phe Ile Glu Thr Ser Ala Lys
145                 150             155                 160

Thr Arg Gln Gly Val Asp Asp Ala Phe Tyr Thr Leu Val Arg Glu Ile
                165             170             175

Arg Lys
```